(12) United States Patent
Yacoubian

(10) Patent No.: US 8,426,933 B2
(45) Date of Patent: Apr. 23, 2013

(54) BROAD SPECTRAL BAND SENSOR

(76) Inventor: Araz Yacoubian, Carlsbad, CA (US)

( * ) Notice: Subject to any disclaimer, the term of this patent is extended or adjusted under 35 U.S.C. 154(b) by 694 days.

(21) Appl. No.: 12/538,026

(22) Filed: Aug. 7, 2009

(65) Prior Publication Data

US 2010/0033710 A1 Feb. 11, 2010

Related U.S. Application Data

(60) Provisional application No. 61/087,593, filed on Aug. 8, 2008.

(51) Int. Cl.
*H01L 29/84* (2006.01)

(52) U.S. Cl.
USPC .............................. 257/416; 73/642; 356/416

(58) Field of Classification Search .................. 310/311, 310/313 R; 257/416; 73/642, 643
See application file for complete search history.

(56) References Cited

U.S. PATENT DOCUMENTS

| | | | | |
|---|---|---|---|---|
| 3,970,778 A * | 7/1976 | Adkins | ........................ | 310/311 |
| 4,025,954 A | 5/1977 | Bert | | |
| 4,041,536 A * | 8/1977 | Melcher et al. | ............... | 348/198 |
| 4,085,348 A * | 4/1978 | Munier | ..................... | 310/313 B |
| 4,099,206 A * | 7/1978 | Desbois et al. | ........... | 310/313 B |
| 4,209,725 A | 6/1980 | Dieulesaint et al. | | |
| 4,281,350 A * | 7/1981 | Maerfeld et al. | .......... | 310/313 B |
| 4,311,938 A | 1/1982 | Ballato et al. | | |
| 4,378,497 A | 3/1983 | Giallorenzi | | |
| 4,524,294 A | 6/1985 | Brody | | |
| 4,847,854 A | 7/1989 | Van Dijk | | |
| 4,893,008 A | 1/1990 | Horikawa | | |
| 5,285,261 A | 2/1994 | Dumoulin | | |
| 5,447,845 A | 9/1995 | Chu et al. | | |
| 6,292,682 B1 | 9/2001 | Kruger | | |
| 6,490,470 B1 | 12/2002 | Kruger | | |
| 6,504,289 B2 | 1/2003 | Toda et al. | | |
| 6,633,774 B2 | 10/2003 | Kruger | | |
| 6,662,040 B1 | 12/2003 | Henrichs et al. | | |
| 6,728,024 B2 | 4/2004 | Ribak | | |
| 6,848,295 B2 | 2/2005 | Auner et al. | | |
| 7,495,369 B2 * | 2/2009 | Yacoubian | .................... | 359/299 |
| 2002/0097962 A1 | 7/2002 | Yoshimura et al. | | |
| 2003/0012478 A1 | 1/2003 | Pokrovski et al. | | |
| 2003/0090664 A1 * | 5/2003 | Amonette et al. | ............ | 356/432 |
| 2004/0220465 A1 | 11/2004 | Cafarella | | |
| 2006/0272419 A1 * | 12/2006 | Maris et al. | ..................... | 73/606 |
| 2012/0217399 A1 * | 8/2012 | Yacoubian | ................. | 250/338.1 |

FOREIGN PATENT DOCUMENTS

| EP | 0576104 A2 | 12/1993 |
|---|---|---|
| EP | 1051536 B1 | 7/2003 |
| WO | WO03/059168 A1 | 7/2003 |

OTHER PUBLICATIONS

PCT International Search Report dated Dec. 28, 2006.

* cited by examiner

*Primary Examiner* — Kara E Geisel
(74) *Attorney, Agent, or Firm* — Ken J. Koestner

(57) ABSTRACT

A sensor and system combine photo-acoustic sensing with elastic wave modulation to obtain one dimensional and two-dimensional broadband images.

26 Claims, 45 Drawing Sheets

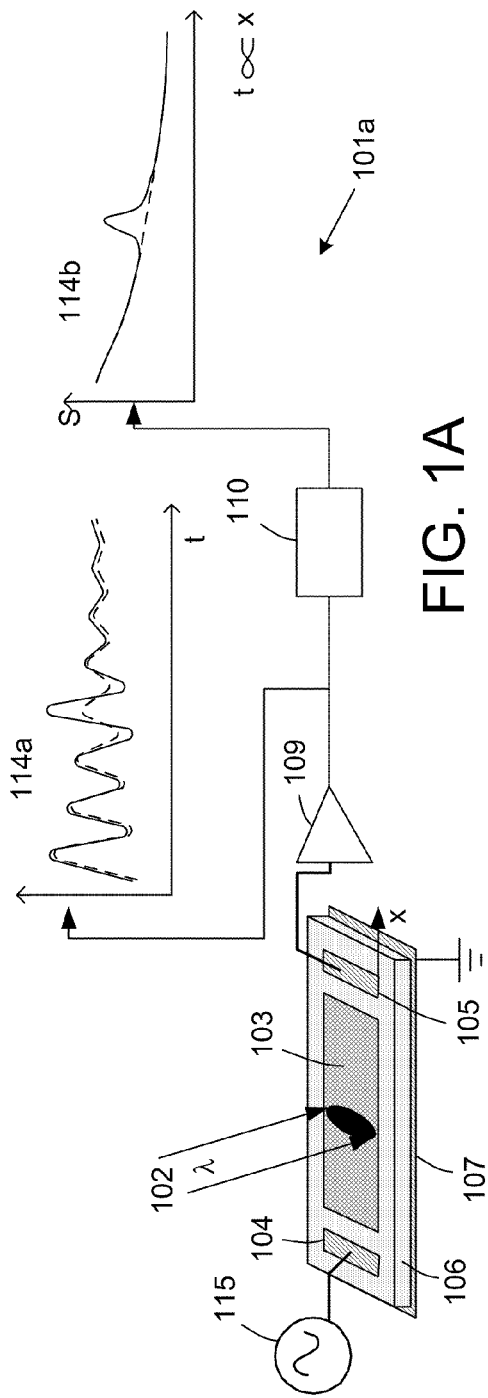
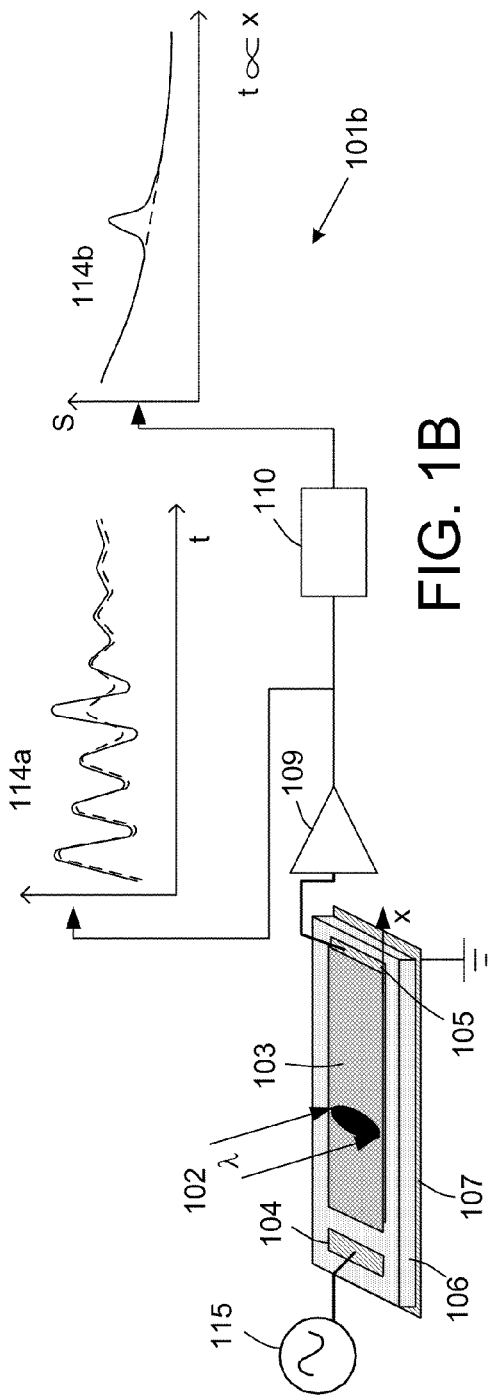

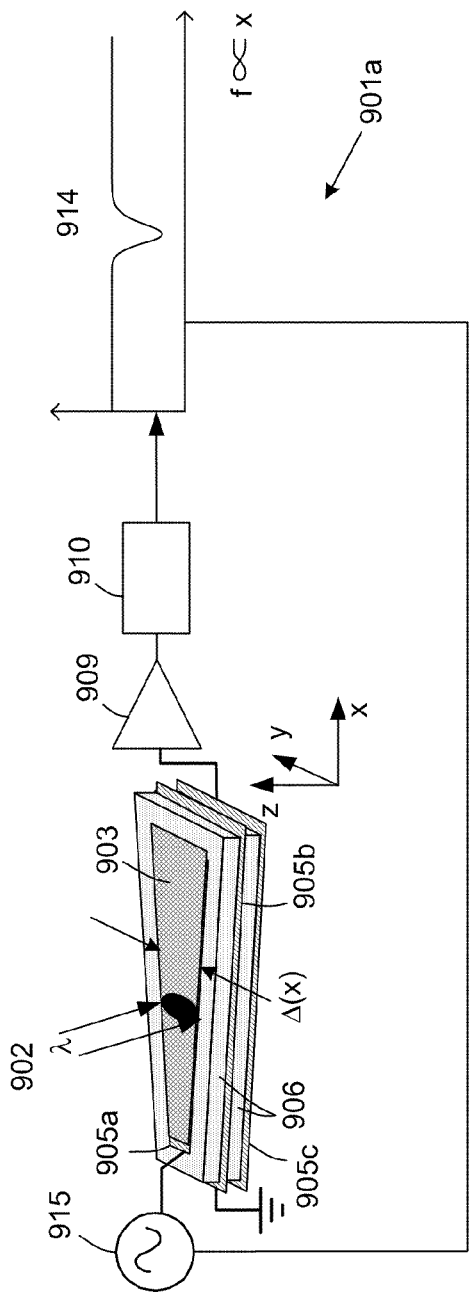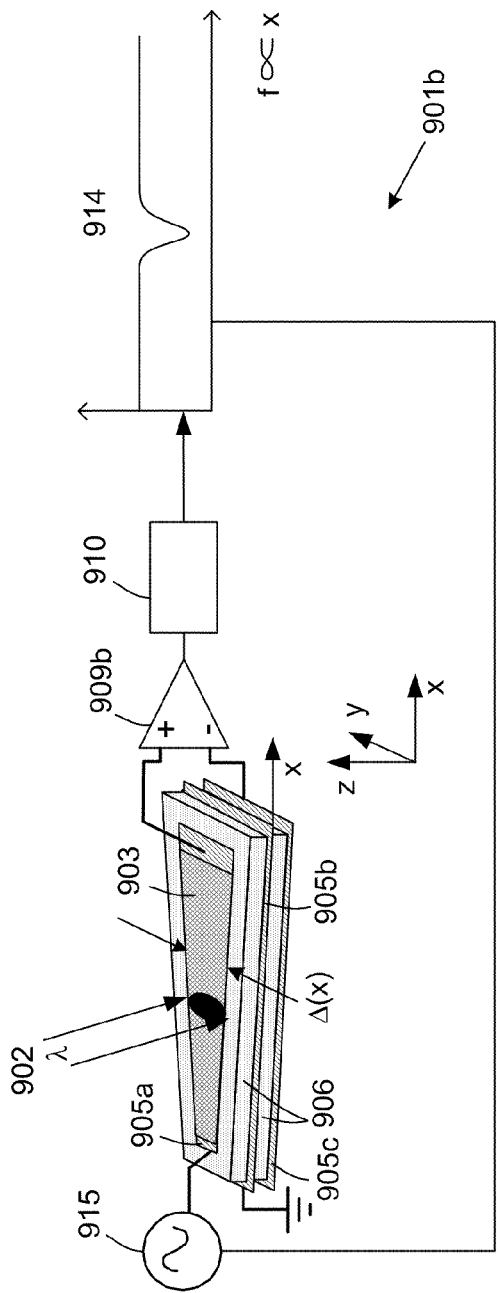

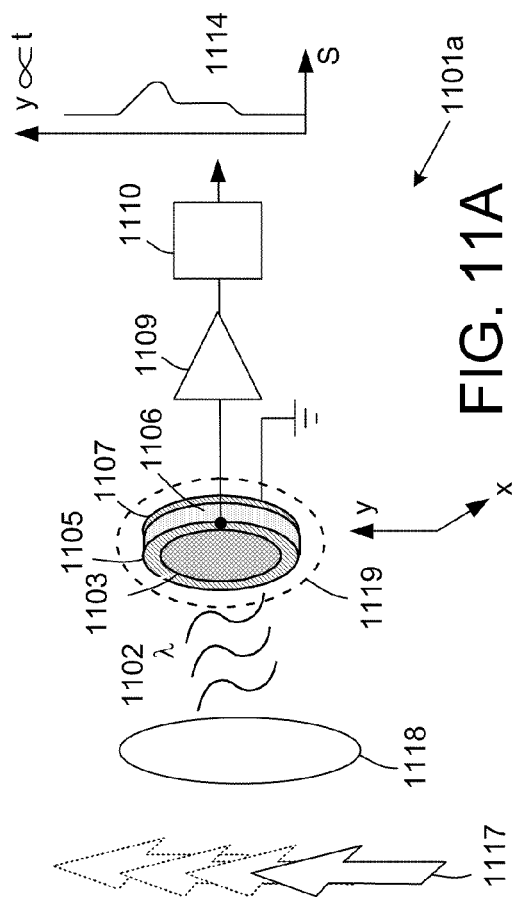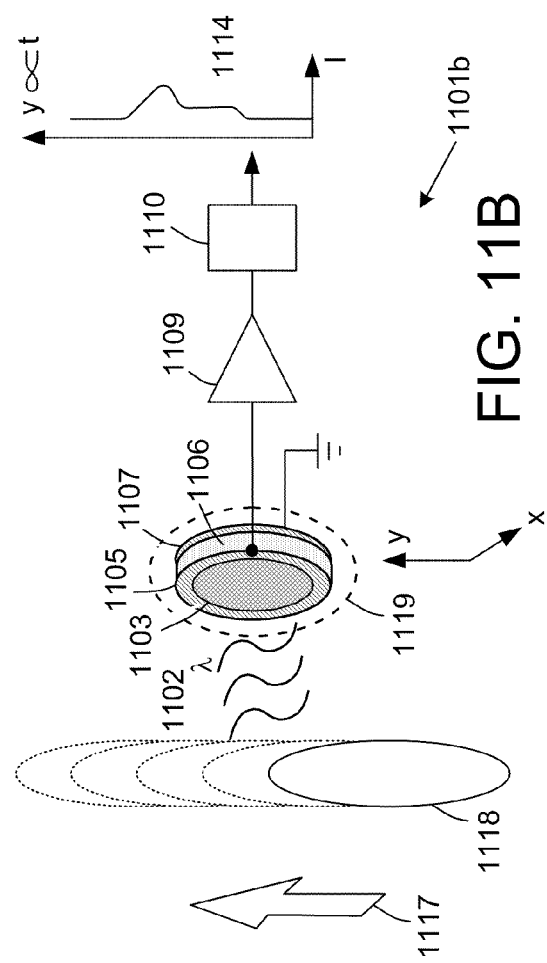

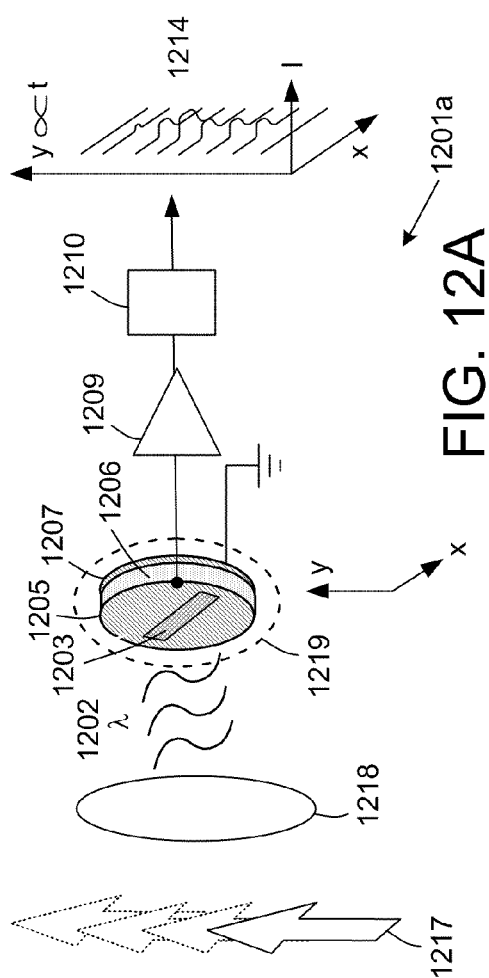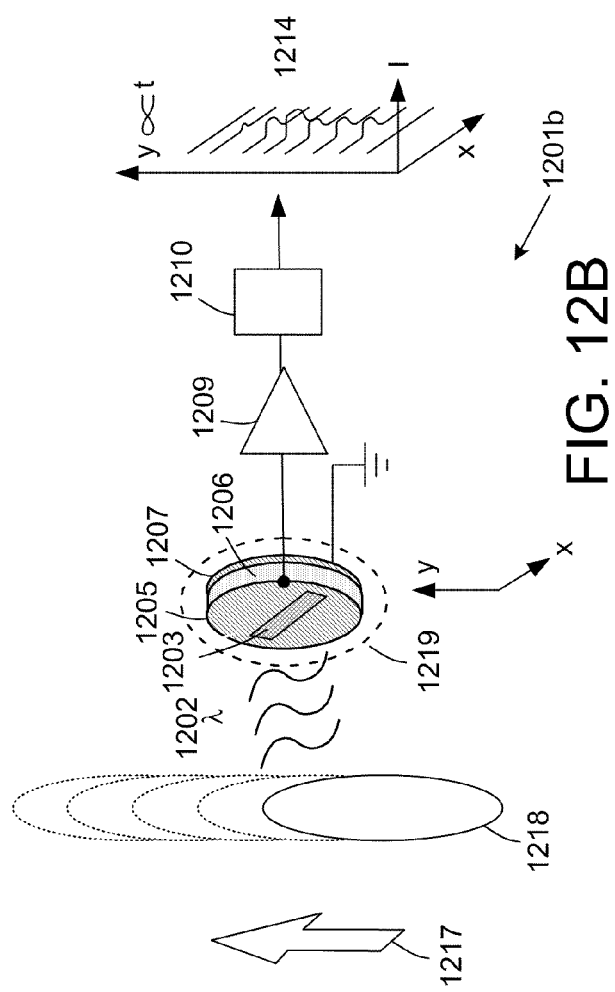

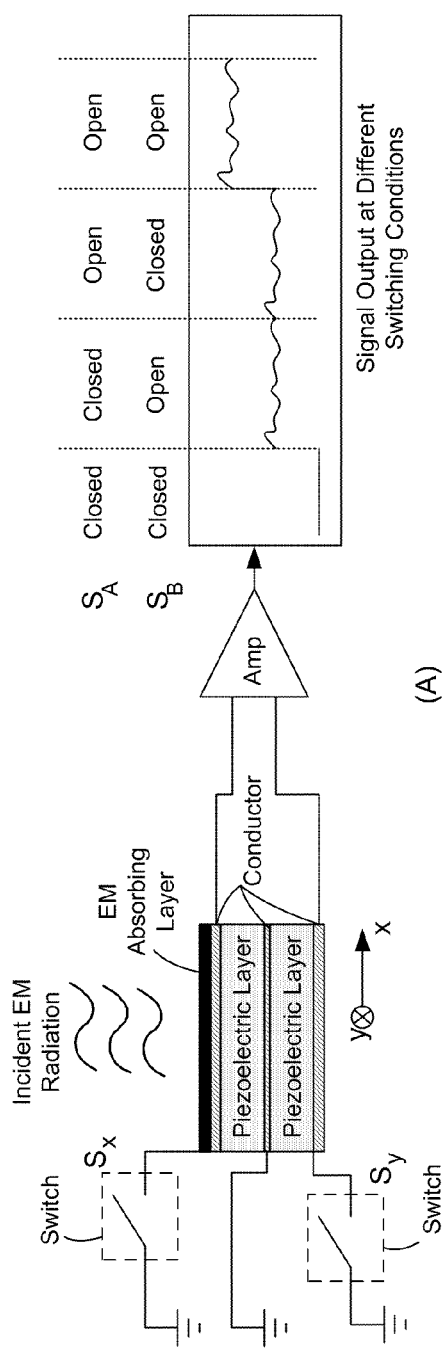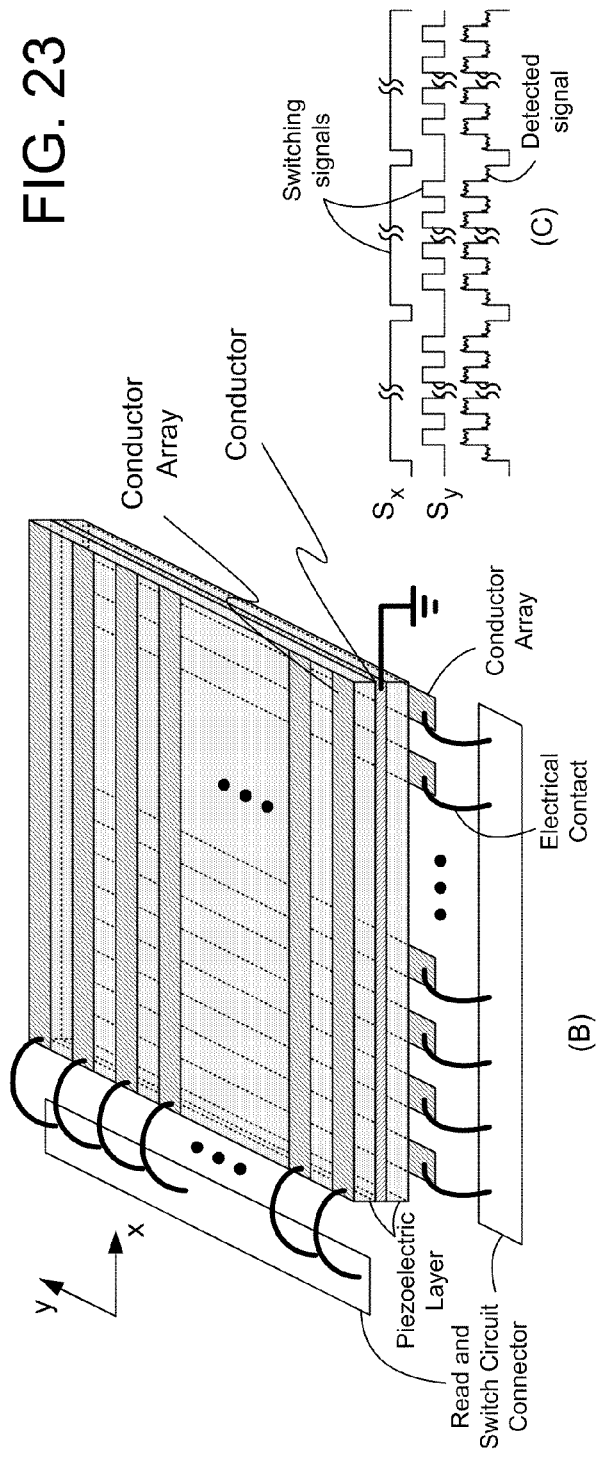
FIG. 23

BROAD SPECTRAL BAND SENSOR

BACKGROUND

Detection of broadband electromagnetic (EM) radiation such as visible, infrared, ultra-violet (UV) radiation, as well as radiation in other parts of the EM spectrum, has great interest in many technology areas. Many current technologies enable detection and imaging only in a narrow part of the EM spectrum, such as visible only, infra-red only, or UV.

Many conventional detection technologies utilize sensing of electronic transition between various states of atoms, excited by the incoming EM radiation, and are therefore limited to a narrow part of the EM spectrum In granted U.S. Pat. No. 7,495,369 B2, Yacoubian describes a method of broadband detection using photo-acoustic approach.

SUMMARY

Embodiments of a sensor and system combine photo-acoustic sensing with elastic wave modulation to obtain one dimensional and two-dimensional broadband images.

BRIEF DESCRIPTION OF THE DRAWINGS

Embodiments of the invention relating to both structure and method of operation may best be understood by referring to the following description and accompanying drawings:

FIGS. 1A, 1B, 2A, and 2B are perspective pictorial and block diagrams illustrating embodiments of sensors configured for one-dimensional photo-acoustic imaging of broadband electromagnetic radiation using traveling elastic waves;

FIGS. 9A through 9D and 10A through 10D are perspective pictorial and block diagrams illustrating embodiments of sensors configured for one-dimensional photo-acoustic imaging of broadband electromagnetic radiation;

FIGS. 11A and 11B are perspective pictorial and block diagrams showing embodiments of sensor configured for one-dimensional photo-acoustic imaging of broadband electromagnetic radiation;

FIGS. 12A and 12B are perspective pictorial and block diagrams depicting embodiments of sensors configured for two-dimensional photo-acoustic imaging of broadband electromagnetic radiation;

FIG. 23 is a pictorial and block diagram of a sensing configuration and a signal waveform which depicts a method of generating two-dimensional image data using multi-layer device;

DETAILED DESCRIPTION

Embodiments of a sensor can use several techniques for imaging using elastic modulation. Three example methods of elastic modulation for imaging may include: a) using traveling elastic waves, b) using thickness change via the piezoelectric effect, and c) using frequency modulation of the elastic waves.

Elastic waves can be modulated and detected either using the same electrode, or using multiple electrodes. In case multiple electrodes are used, the electrodes can be stacked either in a planar configuration or in a multi-layer configuration.

Traveling wave detection is one of the methods of detection and imaging of incident EM radiation, for example using traveling elastic waves. The techniques are depicted in FIGS. 1A, 1B, 2A, and 2B. The method produces one-dimensional line scans or two-dimensional images.

Figure 3:
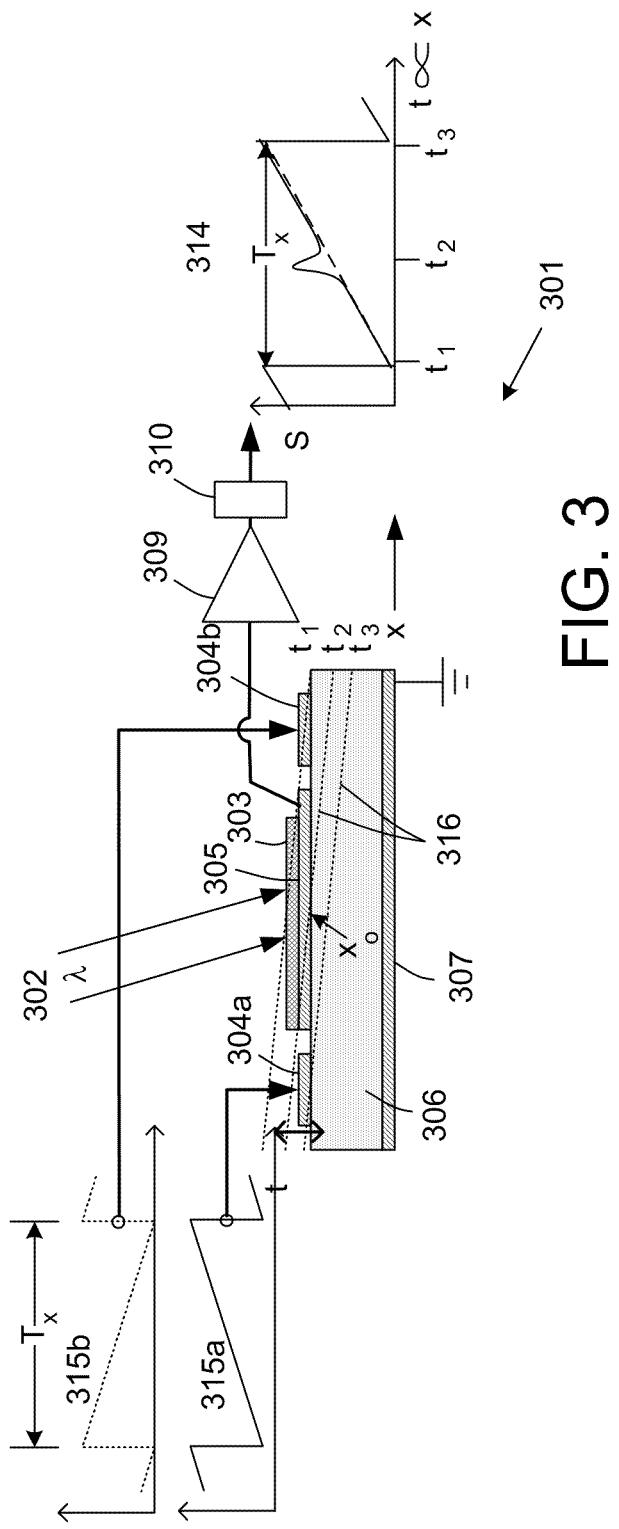
FIG. 3 is a perspective pictorial and block diagram depicting an embodiment of a sensor configured for one-dimensional photo-acoustic imaging of broadband electromagnetic radiation.
Figure 4:
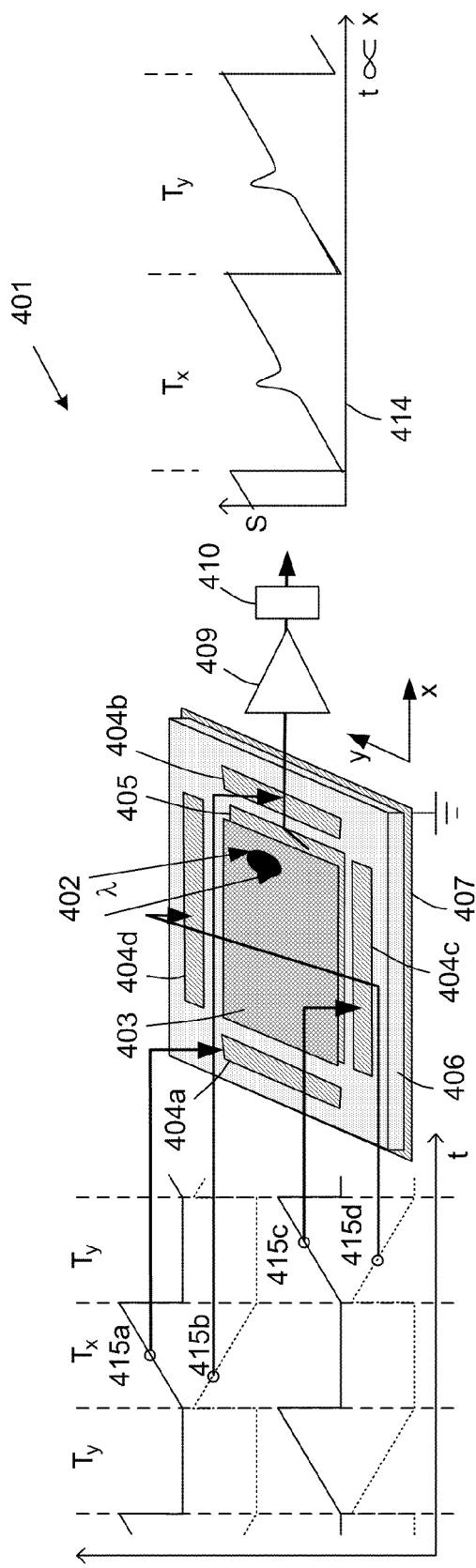
FIG. 4 is a perspective pictorial and block diagram illustrating an embodiment of a sensor configured for two-dimensional photo-acoustic imaging of broadband electromagnetic radiation.

A thickness change detection technique is one of the methods of detection and imaging of incident EM radiation. Electrodes can be used such that the materials change shape due the piezoelectric effect, and the incident alters the shape change. Example techniques and structures are depicted in FIGS. 3 and 4. The method produces one-dimensional line scans or two-dimensional images.

A frequency modulation technique is one of the methods for detection and imaging of incident EM radiation. The technique uses electrodes and absorbing layers of different size and shape that have resonance frequency at different locations. When the electromagnetic (EM) radiation modulation frequency and the sensor resonant frequency match, the presence of the EM radiation has the maximum effect. Since the sensor has different resonance frequencies at different locations, varying the incident source frequency and detecting the signal yields the spatial distribution of the EM radiation. Two various configurations are depicted, one using an electrical modulation, and one where there is no electrical modulation, but only the EM source is modulated. The configurations are depicted in FIGS. 5 and 10 and produce one-dimensional line scans or two-dimensional images, using single or multiple electrodes.

An image scanning technique is one method of obtaining two-dimensional image from a one-dimensional sensor by scanning the object, the optics, and/or the sensor apparatus. Image scanning techniques are depicted in FIGS. 11 and 12. Methods for obtaining two-dimensional image from a single element sensor are depicted in FIGS. 11A and 11B.

Figure 13:
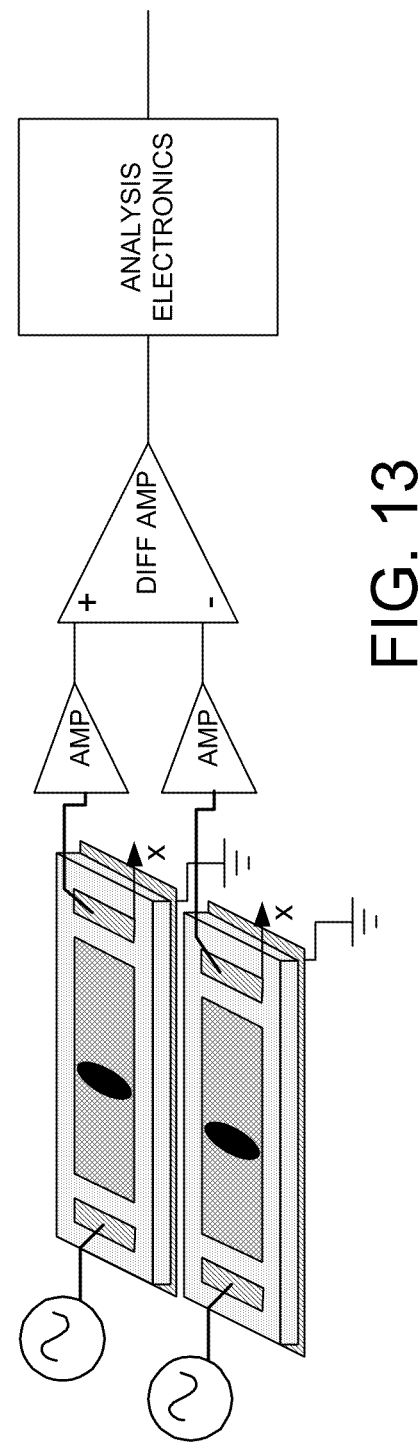
FIG. 13 is a schematic pictorial and block diagram showing a sensor including difference detection.

Difference detection can be used for noise reduction. To reduce noise, two or more identical sensors can be placed in close proximity or on the same substrate. The difference between signals from each sensor can be detected to cancel signal fluctuations and eliminate the noise as depicted in FIG. 13. The illustrative noise reduction technique can be to any multi-electrode design of FIGS. 1 through 12.

Electromagnetic (EM) and acoustic signal detection can be used for noise reduction and signal analysis. The sensors described herein work optimally with alternating current (AC). To achieve optimum performance, either a) the incident EM field varies in time, or b) the device is grounded periodically. The incident EM field may be varying in time naturally (such as if the object is a moving object), or the source that radiates the object may be varying in time. Source modulation can be achieved either electrically, e.g. by using a modulating electrical drive signal or mechanically using a chopper wheel. When the source is modulated, the sensing system can be configured such that noise is reduced by synchronizing the source and detection modulation signals, or by using a lock-in technique, where the source and the detector are locked-in via the modulation signal using standard lock-in amplification method, or using a lock-in amplifier. If the incident EM field is static, the device can be grounded periodically using either electronic method, such as using transistor circuitry, or mechanically, such as using relays. Several methods and apparatus are depicted that can be used to detect both EM and acoustic signature. The signals (e.g. EM, acoustic, or its combination) can be used both as an additional source of information as well as for noise reduction, and both acoustic and EM signals can be correlated (see FIG. 21) for various applications such as for automatic target recognition. The methods and apparatus are depicted in FIGS. 15 to 21 and described herein. The techniques can also be combined with other methods and apparatus depicted and described herein.

Figure 22:
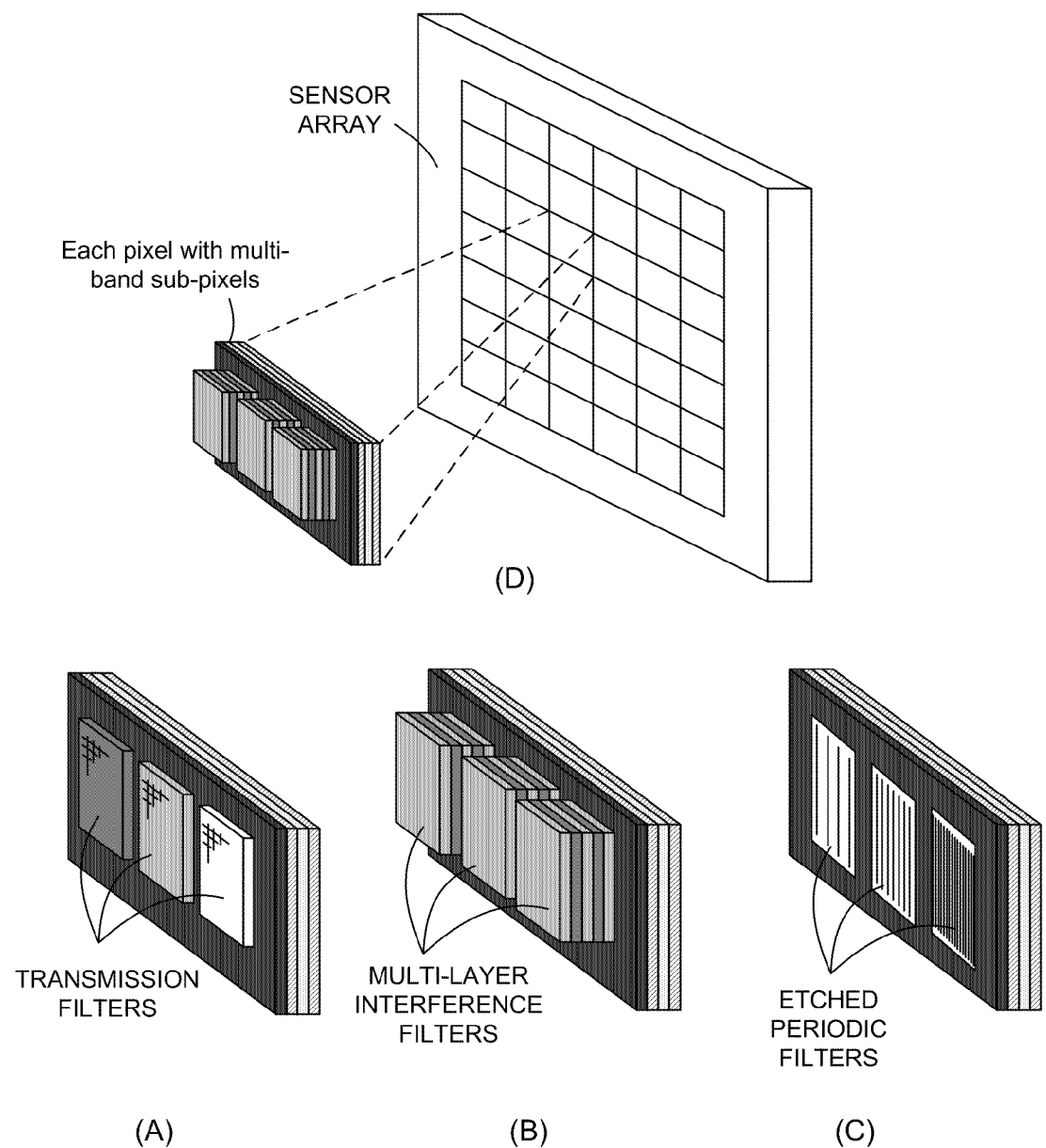
FIG. 22 is a pictorial diagram depicting components that can be used for wavelength filtering.

Wavelength filtering can be used to improve performance. Wavelength filtering schemes are depicted in FIG. 22. The techniques can also be combined with other methods and apparatus depicted and described herein.

Two-dimensional images can be generated using the illustrative techniques disclosed herein. A method and apparatus of forming two-dimensional image of the incident EM, acoustic, or combined EM and acoustic data is depicted in FIG. 23. The method and apparatus can also be combined with other methods and apparatus depicted and described herein.

Figure 25:
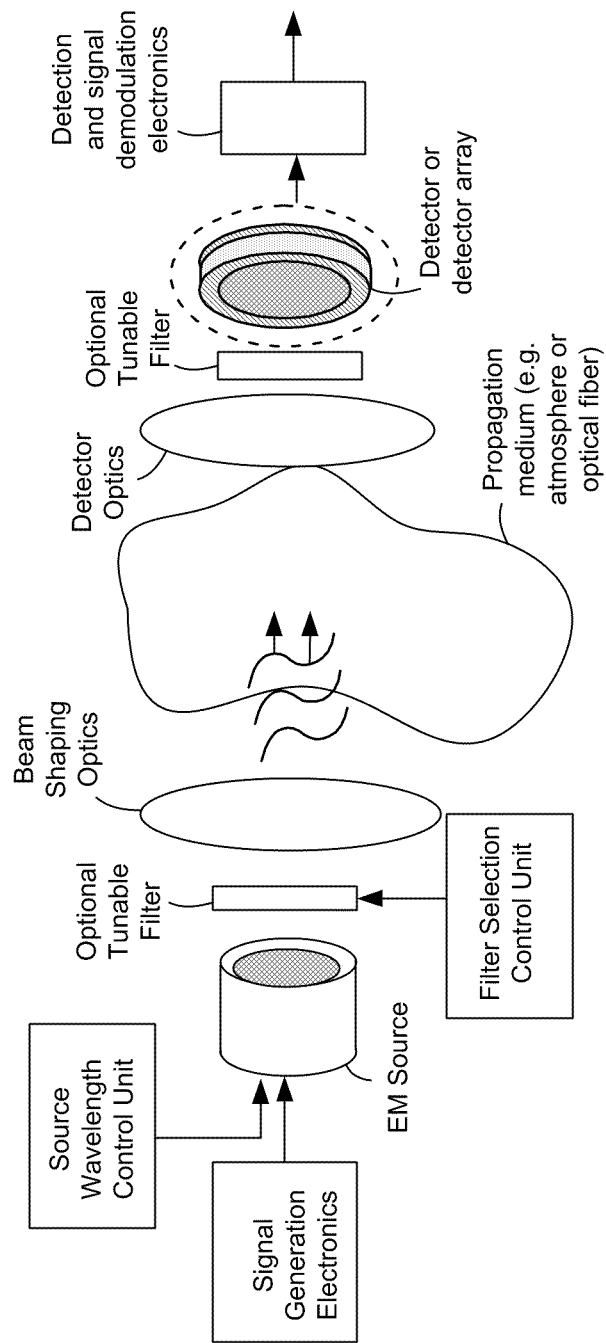
FIG. 25 is a pictorial and block diagram of a sensor and shows application of broadband sensor for communication.

The illustrative broadband sensor can be used for communication. A method and apparatus for using a broadband sensor such as the ones described throughout the disclosure for communication is depicted in FIG. 25.

Figure 27:
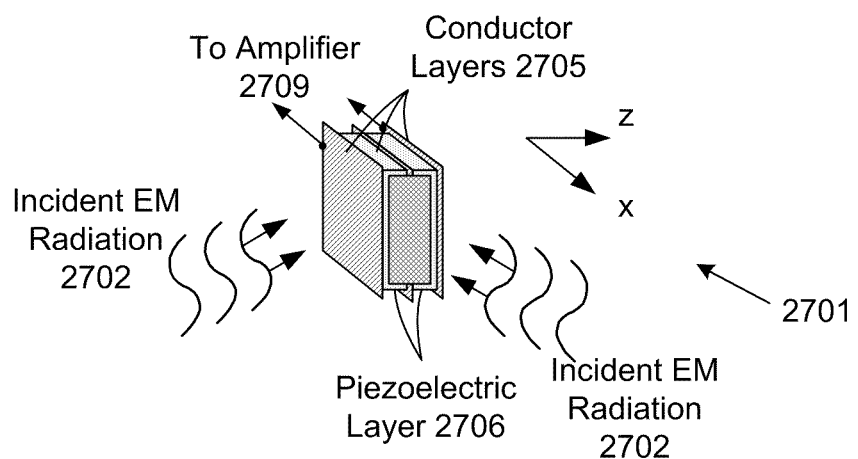
Figure 28:
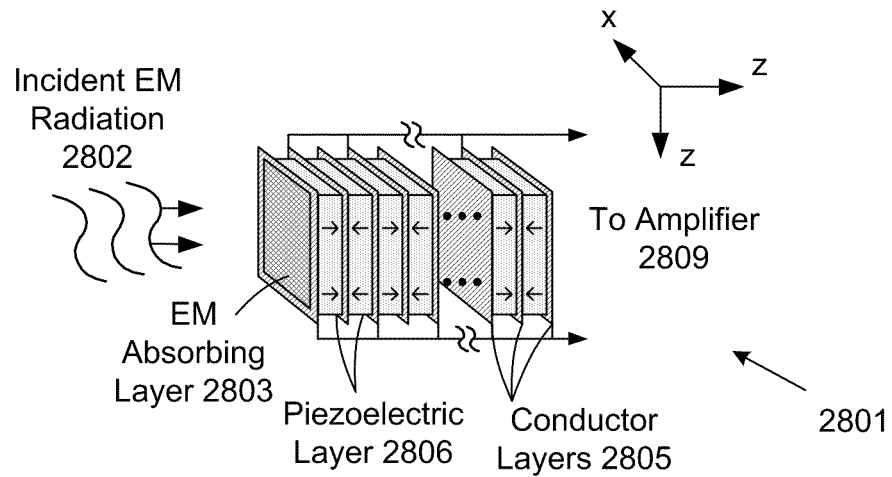
Figure 29:
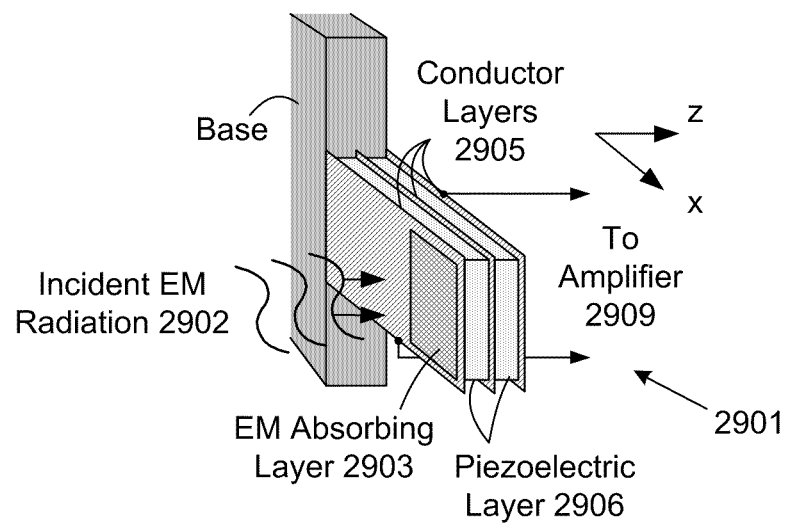

Some sensor embodiments can be implemented in multiple-layer structures. Various methods and apparatus using two or more layers structured broadband sensors are depicted in FIGS. 27 to 29. The multi-layer structures result in higher responsivity compared to a single layer structure.

Some sensor embodiments can be implemented using pixel structures. Various methods and apparatus using pixels to produce one-dimensional and two-dimensional images of the incident EM radiation are described in FIGS. 30 to 32. The disclosed structures and devices enable improved functionality by reducing cross-talk and avoiding resolution loss due to thermal conductivity and acoustic coupling between adjacent pixels. The improvement is achieved by incorporating thermal and acoustic insulating materials in the pixel structures.

Referring to FIG. 1A, a perspective pictorial and block diagram illustrates an embodiment of a sensor configured for one-dimensional photo-acoustic imaging of broadband electromagnetic radiation using traveling elastic waves. The illustrative broadband photo-acoustic detection apparatus 101A is responsive to incident electromagnetic radiation 102 of arbitrary shape and direction, thus arbitrary phase and amplitude, and comprises a darkened surface 103 which absorbs incident electromagnetic (EM) radiation, an excitation electrode 104 and detection electrode 105, a piezoelectric material 106, a conductive layer which may also be used as ground plane 107, and a high-gain, low-noise amplifier 109 and a band-pass filter 110. EM radiation 102 is incident on the darkened surface 103. The excitation and detection electrodes are either a single element electrode, or are inter-digitated electrodes to generate and detect bulk or surface elastic waves. An excitation signal, such as a modulation signal or a pulse is applied to the excitation electrode, which generates elastic waves due to the piezoelectric effect. The wave travels along device, (surface or guided wave), and reaches the detection electrode 105, which generates a signal, again via the piezoelectric effect. Signal from the detection electrode 105 is amplified and displayed 114a. The amplified signal passes through a band-pass or low-pass filter 110, and final signal is displayed 114b. If there is no EM radiation present at the absorbing layer 103, then the signal 114b is a smooth decaying signal. When EM radiation is present at the absorbing layer 103, then the absorbed radiation causes change in the dimension in the absorbed region due to thermal expansion. This then alters the traveling wave amplitude, and thus a change in the signal 114b is visible. The time of occurrence of this change depends on the time of travel of the elastic wave and location and intensity of the incident radiation. The signal 114b therefore indicates amplitude and location of the EM radiation, thus enables one-dimensional imaging of the incident EM radiation.

In another embodiment similar to FIG. 1A, either the excitation electrode of 104 or the detection electrode 105 or both can be inter-digitated electrodes or comb electrodes with either fixed pitch or variable pitch. Inter-digitated electrode width and pitch are designed to match the excitation signal frequency or frequency range to achieve optimum signal excitation and detection efficiency.

In other embodiments, the sensor 101a can be implemented using a capacitive approach. Instead of piezoelectric material, electrode 105 can be replaced with an insulator. Suitable insulators may be a vacuum, air, or other insulators.

When electromagnetic radiation is incident on the absorbing surface or layer 103, the absorbed electromagnetic energy is converted to a mechanical energy via the photo-acoustic effect, and therefore changes the material dimensions, which then interferes with the traveling elastic wave.

Because the detection method uses photo-acoustic effect, the technique can therefore be used to image broadband electromagnetic radiation. The broadband spectrum can include, visible, infrared (IR), ultraviolet (UV) band, X-ray, microwave and higher or lower frequencies, as long as the radiation is absorbed by the absorbing surface of the sensor.

Referring to FIG. 1B, a perspective pictorial and block diagram illustrates an embodiment of a sensor configured for one-dimensional photo-acoustic imaging of broadband electromagnetic radiation using traveling elastic waves. The photo-acoustic imaging sensor 101a apparatus shown in FIG. 1A can be further modified by using an detection electrode 105 that has the same or similar size footprint as the absorbing layer 103, and the absorbing layer is coated over the detection electrode 105.

In another embodiment similar to FIG. 1B either the excitation electrode 104 or the detection electrode 105 or both can be inter-digitated electrodes or comb electrodes with either fixed pitch or variable pitch. Inter-digitated electrode width and pitch should be designed to match the excitation signal frequency or frequency range to achieve optimum signal excitation and detection efficiency.

Figure 2A:
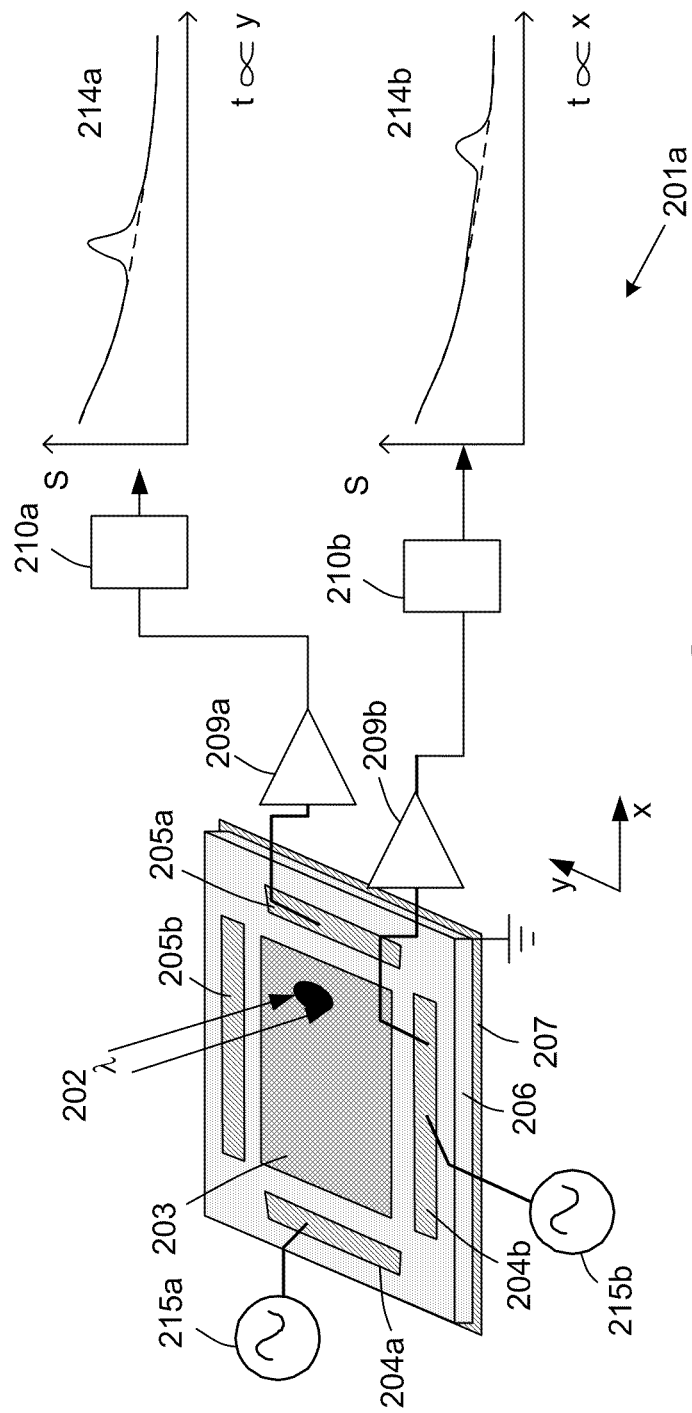

Referring to FIG. 2A, a perspective pictorial and block diagram illustrates an embodiment of a sensor 201a configured for two-dimensional photo-acoustic imaging of broadband electromagnetic radiation using traveling elastic waves. The photo-acoustic sensor 101a apparatus shown in FIG. 1A is further modified to image two-dimensional incident EM radiation. Two excitation electrodes 204a and 204b and two detection electrodes 205a and 205b are used for generation and detection of traveling waves. To differentiate between x and y directions, the x-direction electrodes 204a and the y-direction electrodes 204b are excited with two different frequencies from sources 215a and 215b. The signals from detection electrodes 205a and 205b are sent to amplifiers 209a and 209b. The amplified signals are band-pass filtered 210a and 210b such that only certain frequencies are passed so that the x and y traveling wave signals are separated. The filtered x and y signals 214a and 214b indicate presence of EM radiation incident on the absorbing layer 202. Set 206 and 207 are equivalent to set 106 and 107.

In another embodiment similar to FIG. 2A either one or both of the excitation electrodes 204a and 204b or one or both of the detection electrodes 105a and 205b or all the electrodes or any combination thereof are inter-digitated electrodes or comb electrode with either fixed pitch or variable pitch. Inter-digitated electrode width and pitch should be designed to match the excitation signal frequency or frequency range to achieve optimum signal excitation and detection efficiency.

Figure 2B:
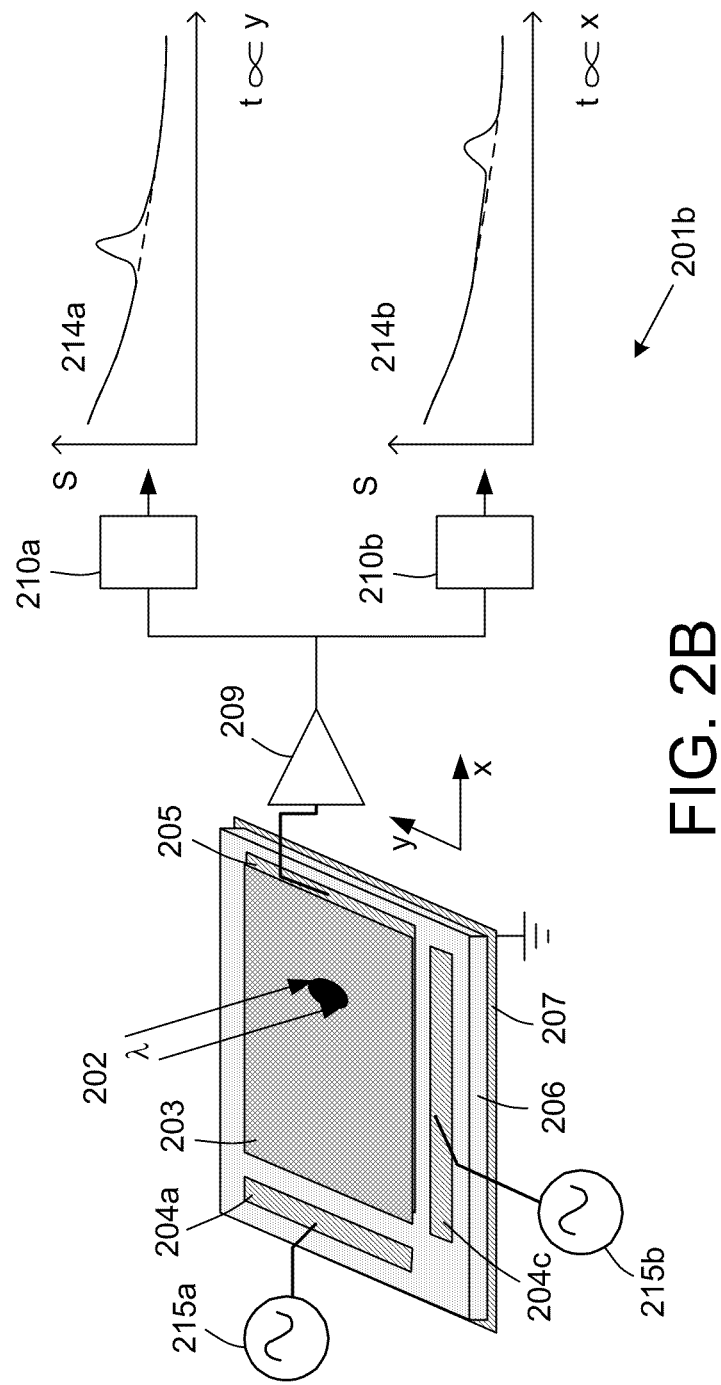

Referring to FIG. 2B, a perspective pictorial and block diagram illustrates an embodiment of a sensor 201b configured for two-dimensional photo-acoustic imaging of broadband electromagnetic radiation using traveling elastic waves. The photo-acoustic imaging sensor 201a apparatus shown in FIG. 2A is further modified by using a single detection electrode 205 that has the same or similar size footprint as the absorbing layer 203, and the absorbing layer is coated over the detection electrode 205. Two excitation electrodes 204a and 204b are used to generate traveling wave signal generated from signal generators 215a and 215b. To differentiate between x and y directions, the x-direction electrodes 204a and the y-direction electrodes 204b are excited with two different frequencies from signal sources 215a and 215b. The signal from detection electrodes 205 is sent to amplifiers 209. The amplified signal is split into two and sent to two band-pass filters 210a and 210b such that only certain frequencies are passed so that the x and y traveling wave signals are separated. The filtered x and y signals 214a and 214b indicate presence and intensity distribution of EM radiation 202 incident on the absorbing layer 203. Set 206 and 207 are equivalent to set 106 and 107.

In another embodiment similar to FIG. 2B either one or both of the excitation electrodes 204a and 204b or the detection electrode 105 or all the electrodes or any combination thereof, are inter-digitated electrodes or comb electrode with either fixed pitch or variable pitch. Inter-digitated electrode width and pitch should be designed to match the excitation signal frequency or frequency range to achieve optimum signal excitation and detection efficiency.

Referring to FIG. 3, a perspective pictorial and block diagram illustrates an embodiment of a sensor configured for one-dimensional photo-acoustic imaging of broadband electromagnetic radiation. By applying a saw-tooth or a triangular modulated electrical signal 315a and 315b to excitation electrodes 304a and 304b, the material will expand or contract due to piezoelectric effect as shown in the dotted line 316. The detection electrode 305 is coated with an absorbing layer 303 to absorb the incident radiation 302. The signal from the detection elected 305 is fed to a high-gain, low-noise amplifier 309 and an optional band-pass filter 310. The output signal 314 from the amplifier/filter is also modulated due to the excitation signal. When EM radiation is present at the absorbing layer 303, the absorbed radiation causes change in the dimension in the absorbed region due to thermal expansion. This change alters the output signal due the piezoelectric effect. EM radiation has maximum effect when the material is at is rest condition, namely, when change in dimension is minimum due to excitation effect. In this figure, at time $t_2$, point $x_o$ is equivalent to the rest position with no applied field. When the EM radiation 302 is incident at this spot, it has the maximum effect, and a change in the output signal 314 appears. Therefore, position of the change in the signal indicates the presence of EM field. Furthermore, the amplitude of this change is proportional to the incident radiation intensity. Therefore, the temporal position of the change indicates the x position, and the amplitude of the signal change indicates the intensity of the incident radiation, thus acting as a line scanner in the x direction. Set 306 and 307 are equivalent to set 106 and 107.

Referring to FIG. 4, a perspective pictorial and block diagram illustrates an embodiment of a sensor configured for two-dimensional photo-acoustic imaging of broadband electromagnetic radiation. The sensor design is based on the same concept as used in FIG. 3, but modified for two-dimensional imaging. Four excitation electrodes 404a, 404b, 404c, and 404d are excited with four saw-tooth or a triangular modulated electrical signal 415a, 415b, 415c and 415d. In a similar method as for the apparatus shown in FIG. 3, the output signal 414 depicts presence of incident radiation. The excitation signal modulation is time such that x and y dimensions are scanned serially in intervals $T_x$, $T_y$. Therefore the output signal 415 indicates incident EM radiation intensity and spatial distribution in x and y directions. Items 402, 406, 407, 409, 410 are equivalent to corresponding set 102, 106, 107, 109, 110.

Figure 5A:
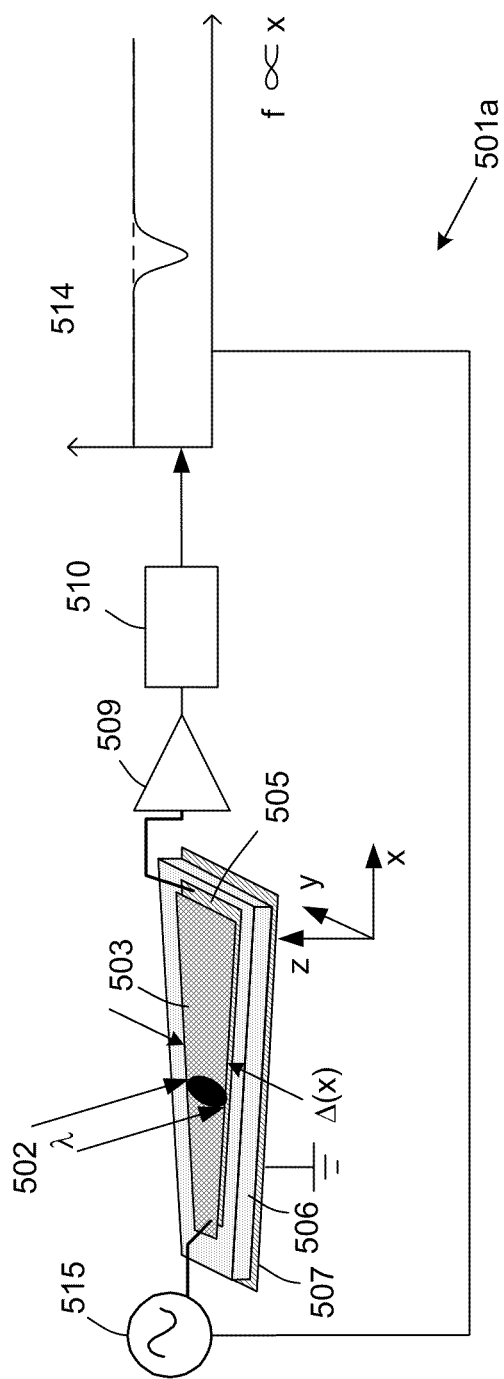
FIGS. 5A and 5B are perspective pictorial and block diagrams showing embodiments of sensors configured for one-dimensional photo-acoustic imaging of broadband electromagnetic radiation.

Referring to FIG. 5A, a perspective pictorial and block diagram illustrates an embodiment of a sensor configured for one-dimensional photo-acoustic imaging of broadband electromagnetic radiation. A piezoelectric layer 506 is sandwiched between an electrode 505 and a ground plane 507. The electrode is coated with a wide-band EM absorbing layer 503, such as a carbon coating or a black paint. A modulation signal 515 is applied to the electrode 505. The signal is scanned from low to high frequencies. The electrode 505 is tapered to a narrow width on one side, widening to the other side. When a modulation frequency 515 is applied to the electrode 505, the device oscillates due to the piezoelectric effect. A high-gain, low-noise amplifier 509 is connected to the electrode 505, followed by a band-pass filter 510. The maximum expansion and contraction of the layers in z direction occur where the electrode width $\Delta(x)$ equals the half wave frequency of the acoustic wave generated by the oscillating signal 515. When the frequency is scanned, then the resonant spot is shifted. At the presence of an incident EM radiation 502, the amplitude as well as frequency of vibration is altered. The maximum change occurs when radiation is incident on the resonant spot. This change yields change in amplitude in the signal 514, thus indicating the spatial distribution of the resonant incident radiation. The change in amplitude is dependent on the incident radiation intensity and location, and therefore the signal 514 yields both intensity and spatial distribution of the incident radiation.

In another embodiment, the band-pass filter 510 in FIG. 5A can be replaced with a frequency detecting electronic circuit and the signal 514 yields change in modulation frequency due to presence of incident radiation, and yields the spatial and amplitude distribution of the incident EM radiation.

In another embodiment, the band-pass filter 510 in FIG. 5A can be replaced with a phase detecting electronic circuit and the signal 514 yields change in phase of the modulation signal due to presence of incident radiation, and yields the spatial and amplitude distribution of the incident EM radiation.

Yet in another embodiment the tapered electrode 505 in FIG. 5A, the overlaying absorptive coating 503, the piezoelectric layer 506 and the ground plane 507 can be of any arbitrary shape that will span any range of frequencies to yield spatial distribution of the incident radiation. The specific shape parameters are application-specific, and are chosen considering image size, resolution.

Figure 5B:
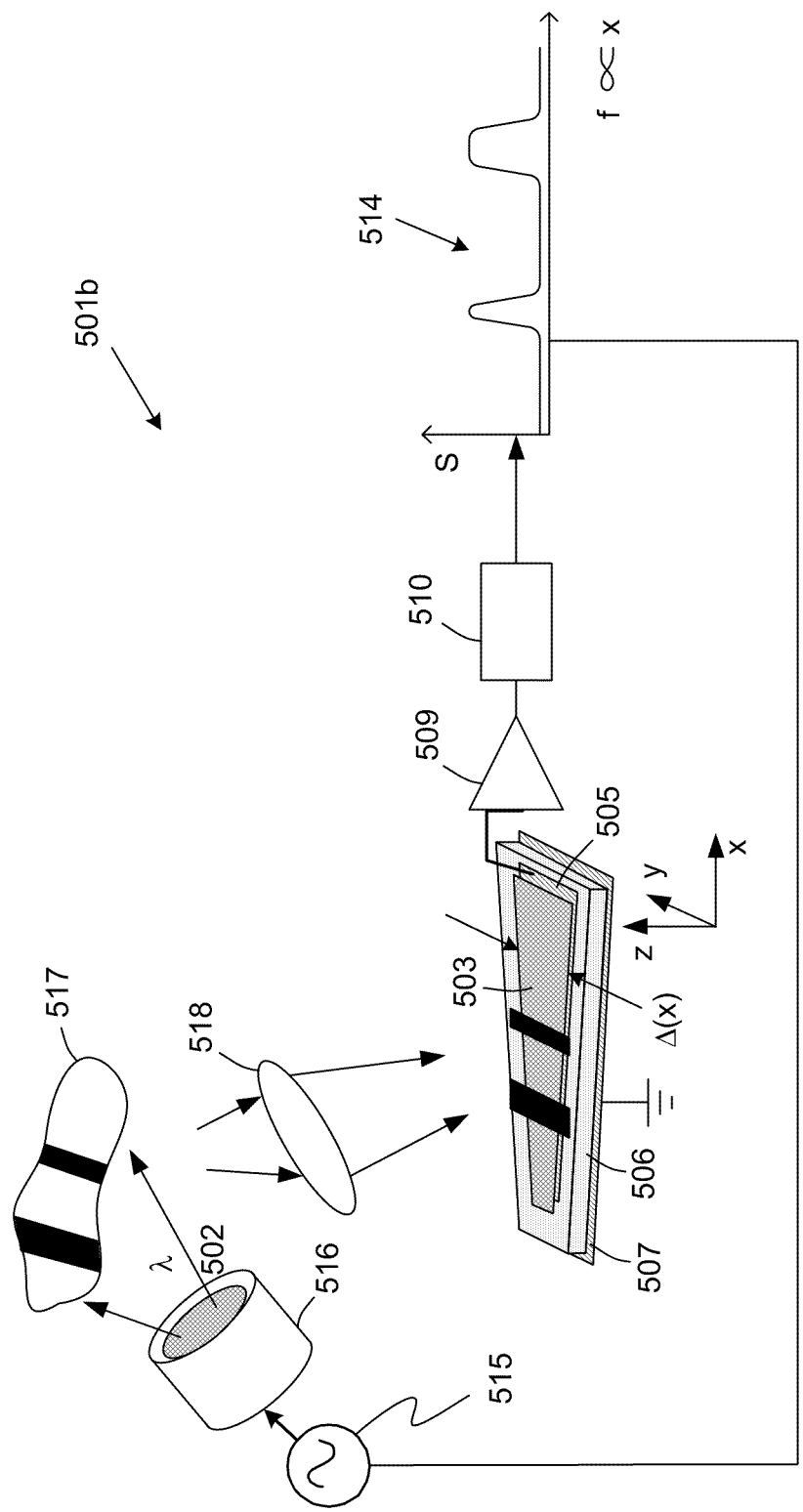

Referring to FIG. 5B, a perspective pictorial and block diagram illustrates an embodiment of a sensor configured for one-dimensional photo-acoustic imaging of broadband electromagnetic radiation. The methodology is similar to that of FIG. 5A, however instead of applying the modulation signal to the electrode 505, the EM source 516 which illuminates an object 517 is modulated. The modulated EM radiation reflects from the surface of objects, carrying spatial information about the object. An optional lens 518 or imaging optics is used to focus the reflected or scattered EM radiation from the object 517 onto the sensor absorbing surface 503. The electrode 505 is connected to a high-gain, low-noise amplifier 509 and to an optional band-pass filter to filter out unwanted noise. The detected signal 514 is displayed in a frequency plot. The signal has highest modulation amplitude when the source modulation frequency matches the resonant frequency of the spot in x direction, which is controlled by the width $\Delta(x)$ of the tapered electrode 505. Therefore scanning the frequency yields the spatial and amplitude distribution of the incident radiation, namely object reflection.

In another embodiment, the band-pass filter 510 in FIG. 5B can be replaced with a frequency detecting electronic circuit and the signal 514 yields change in modulation frequency due to presence of incident radiation, and yields the spatial and amplitude distribution of the incident EM radiation.

Yet in another embodiment, the band-pass filter 510 in FIG. 5B can be replaced with a phase detecting electronic circuit and the signal 514 yields change in phase of the modulation signal due to presence of incident radiation, and yields the spatial and amplitude distribution of the incident EM radiation.

In another embodiment, the EM source 516 is placed such that it illuminates the object 517 from the back, thus the detected signal 514 reveals the optical transmission characteristics of the object 517.

Yet in another embodiment the tapered electrode 505 in FIG. 5B, the overlaying absorptive coating 503, the piezoelectric layer 506 and the ground plane 507 can be of any arbitrary shape that will span any range of frequencies to yield spatial distribution of the incident radiation. Specific shape parameters are application-specific, and are chosen considering image size, resolution.

Figure 6A:
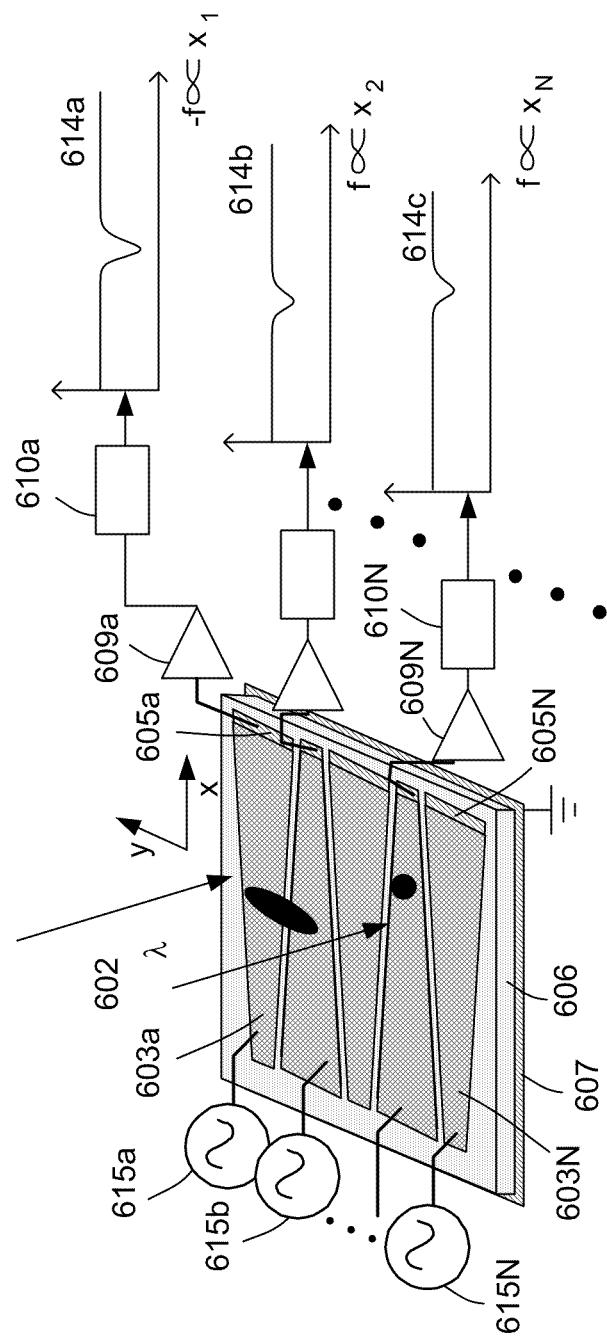
FIGS. 6A, 6B, 7A, 7B, 8A, and 8B are perspective pictorial and block diagrams depicting embodiments of sensors configured for two-dimensional photo-acoustic imaging of broadband electromagnetic radiation.

Referring to FIG. 6A, a perspective pictorial and block diagram illustrates an embodiment of a sensor configured for two-dimensional photo-acoustic imaging of broadband electromagnetic radiation. The sensor is based on the same concept as shown in FIG. 5A, however is repeated for two-dimensions. In this case, N number of tapered excitation electrodes 604a to 604N coated with absorptive layers 603a to 603N are excited with N saw-tooth or a triangular modulated electrical signal 615a to 615N. In a similar method as for FIG. 5A apparatus, the output signal 614a to 614N yields the spatial amplitude distribution in x direction of incident EM radiation. N electrode outputs indicate the y-coordinate of the incident EM radiation spatial and amplitude distribution. The electrodes 605a to 605N are tapered either in the same x direction, or in an opposite direction, as depicted. If of alternating taper direction, then the signal output is displayed accordingly, specifically, 614a to 614N have to be displayed in f and −f directions.

In another embodiment, the band-pass filters 610a to 610b in FIG. 6A are replaced with frequency detecting electronic circuits and the signals 614a to 614b yield change in modulation frequency due to presence of incident radiation, and yields the spatial and amplitude distribution of the incident EM radiation.

In another embodiment, the band-pass filters 610a to 610b in FIG. 6A are replaced with phase detecting electronic circuits and the signals 614a to 614b yield change in modulation frequency due to presence of incident radiation, and yields the spatial and amplitude distribution of the incident EM radiation.

Yet in another embodiment the tapered electrodes 605a to 605N in FIG. 6A, the overlaying absorptive coatings 603a to 603N, the piezoelectric layer 606 and the ground plane 607 can be of any arbitrary shape that will span any range of frequencies to yield spatial distribution of the incident radiation. The specific shape parameters are application-specific, and are chosen considering image size, resolution.

Figure 6B:
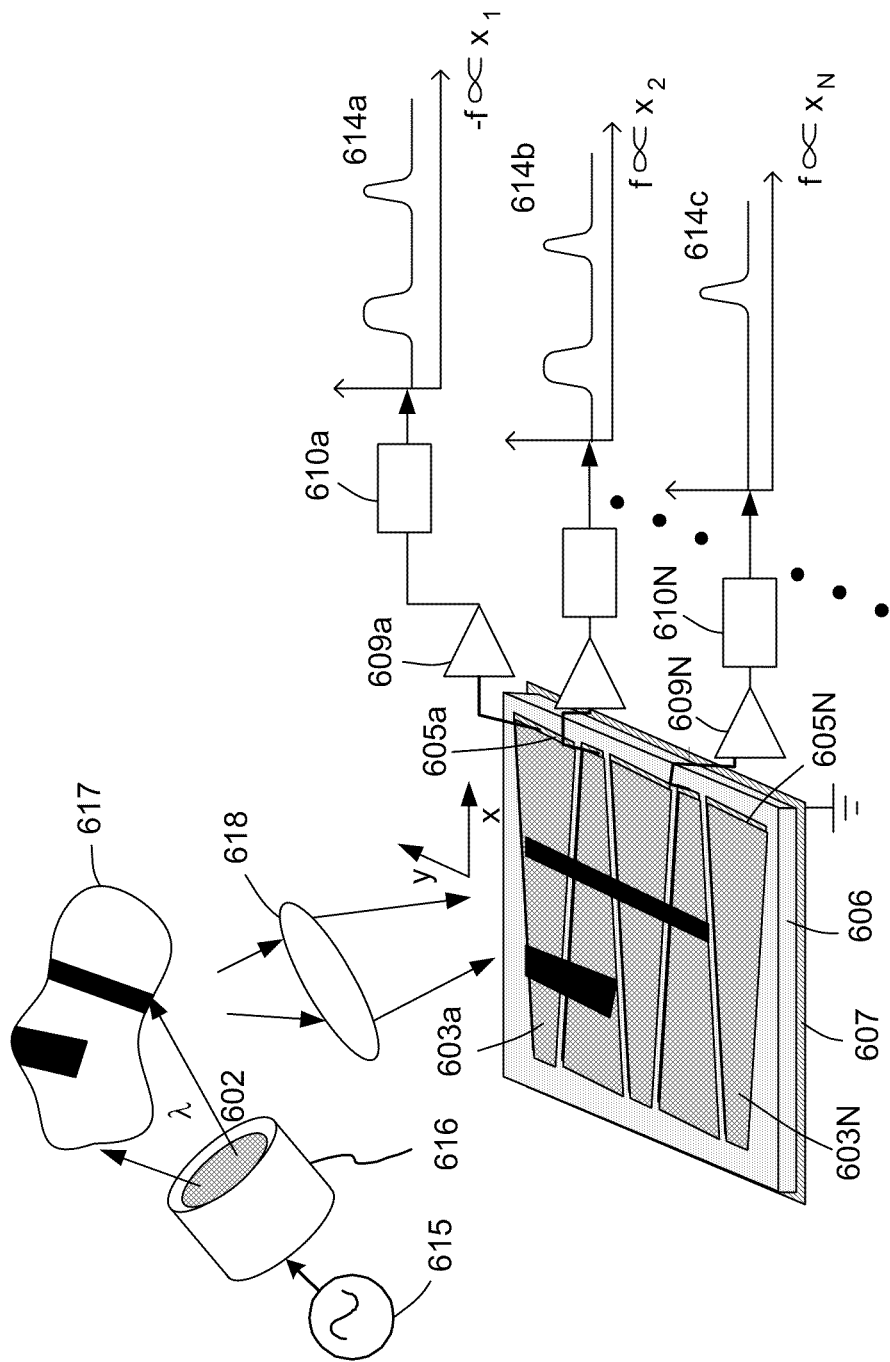

Referring to FIG. 6B, a perspective pictorial and block diagram illustrates an embodiment of a sensor configured for two-dimensional photo-acoustic imaging of broadband electromagnetic radiation. The methodology is similar to that of FIG. 6A, however instead of applying the modulation signal to the electrodes 605a to 605N, the EM source 616 which illuminates an object 617 is modulated. The modulated EM radiation reflects from the surface of objects, carrying spatial information about the object reflection. An optional lens 618 or imaging optics is used to focus the reflected or scattered EM radiation from the object 617 onto the sensor absorbing surface 603a to 604N. The electrodes 505a to 505N are connected to a high-gain, low-noise amplifiers 609a to 609N and to an optional band-pass filters 610a to 610N to filter out unwanted noise. The detected signals 614a to 614N are displayed in a frequency plot. The signal has highest modulation amplitude when the source modulation frequency matches the resonant frequency of the spot in x direction, which is controlled by the width Δ(x) of the tapered electrode 605a to 605N. Therefore scanning the frequency yields the spatial and amplitude distribution of the incident radiation, namely object reflection. The electrodes 605a to 605N are tapered either in the same x direction, or in an opposite direction, as depicted. If they are of alternating taper direction, then the signal output has to be displayed accordingly, specifically, 614a to 614N are displayed in f and –f directions.

In another embodiment, the band-pass filters 610a to 610b in FIG. 6B are replaced with frequency detecting electronic circuits and the signals 614a to 614b yield change in modulation frequency due to presence of incident radiation, and yields the spatial and amplitude distribution of the incident EM radiation.

In another embodiment, the band-pass filters 610a to 610b in FIG. 6B are replaced with phase detecting electronic circuits and the signals 614a to 614b yield change in modulation frequency due to presence of incident radiation, and yields the spatial and amplitude distribution of the incident EM radiation.

Yet in another embodiment the tapered electrodes 605a to 605N in FIG. 6B, the overlaying absorptive coatings 603a to 603N, the piezoelectric layer 606 and the ground plane 607 can be of any arbitrary shape that will span any range of frequencies to yield spatial distribution of the incident radiation. Specific shape parameters are application-specific, and are chosen considering image size, resolution.

Figure 7A:
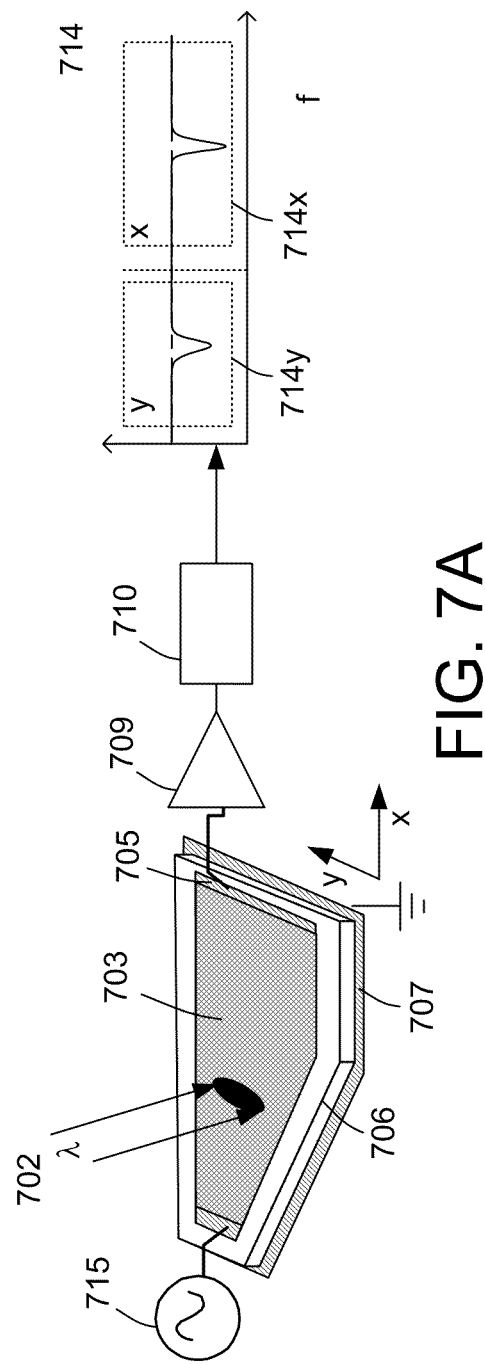

FIG. 7A, a perspective pictorial and block diagram illustrates an embodiment of a sensor configured for two-dimensional photo-acoustic imaging of broadband electromagnetic radiation. A piezoelectric layer 706 is sandwiched between an electrode 705 and a ground plane 707. The electrode is coated with a wide-band EM absorbing layer 703, such as a carbon coating or a black paint. A modulation signal 715 is applied to the electrode 705. The signal is scanned from low to high frequencies. The electrode 705 is tapered both in x- and y-directions such that it is narrow on one side, and wider on the other. When a modulation frequency 715 is applied to the electrode 705, the device oscillates due to the piezoelectric effect. A high-gain, low-noise amplifier 709 is connected to the electrode 705, followed by a band-pass filter 710. The maximum expansion and contraction of the layers in z direction occur where the electrode width Δ(x) or Δ(y) equals the half wave frequency of the acoustic wave generated by the oscillating signal 715. When the oscillator signal 715 scanned from low to high-frequencies, the resonant spot is shifted. The x- and y-tapers are such that the resonant frequency range in each direction does not overlap each other. At the presence of an incident EM radiation 702, the amplitude as well as frequency of vibration is altered. The maximum change occurs when radiation is incident on the resonant spot. This change yields change in amplitude in the signal 714, thus indicating the spatial distribution of the resonant incident radiation. The change in amplitude is dependent on the incident radiation intensity and location, and therefore the signal 714 yields both intensity and spatial distribution of the incident radiation. Each region in the frequency plot is proportional to the x- and y-directions (marked as 714x and 714y), thus their combination yields two-dimensional spatial EM radiation distribution.

In another embodiment, the band-pass filter 710 in FIG. 7A can be replaced with a frequency detecting electronic circuit and the signal 714 yields change in modulation frequency due to presence of incident radiation, and yields the spatial and amplitude distribution of the incident EM radiation.

In another embodiment, the band-pass filter 710 in FIG. 7A can be replaced with a phase detecting electronic circuit and the signal 714 yields change in phase of the modulation signal due to presence of incident radiation, and yields the spatial and amplitude distribution of the incident EM radiation.

Yet in another embodiment the tapered electrode 705 in FIG. 7A, the overlaying absorptive coating 703, the piezoelectric layer 706 and the ground plane 707 can be of any arbitrary shape that span any range of frequencies to yield spatial distribution of the incident radiation. Specific shape parameters are application-specific, and are chosen considering image size, resolution.

Figure 7B:
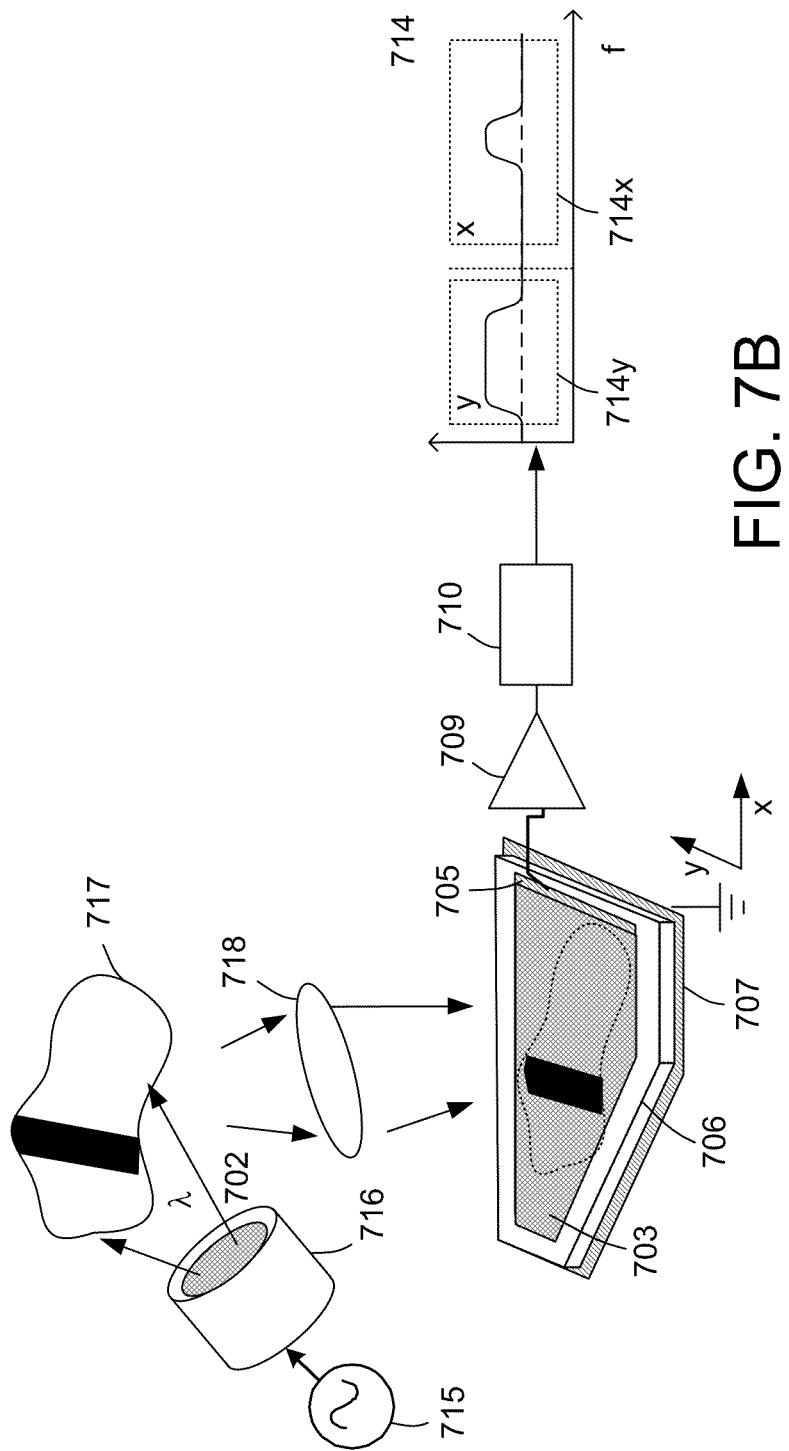

Referring to FIG. 7B, a perspective pictorial and block diagram illustrates an embodiment of a sensor configured for two-dimensional photo-acoustic imaging of broadband electromagnetic radiation. A piezoelectric layer 706 is sandwiched between an electrode 705 and a ground plane 707. The electrode is coated with a wide-band EM absorbing layer 703, such as a carbon coating or a black paint. The methodology is similar to that of FIG. 7A, however instead of applying the modulation signal to the electrodes 705, the EM source 716 which illuminates an object 717 is modulated. The modulated EM radiation reflects from the surface of objects, carrying spatial information about the object reflection. An optional lens 718 or imaging optics is used to focus the reflected or scattered EM radiation from the object 717 onto the sensor absorbing surface 703. The electrode 705 is connected to a high-gain, low-noise amplifier 709 and to an optional band-pass filter 710 to filter out unwanted noise. The detected signal 714 is displayed in a frequency plot. The signal has highest modulation amplitude when the source modulation frequency matches the resonant frequency of the spot in x or y direction, which is controlled by the width Δ(x) and Δ(y). The maximum expansion and contraction of the layers in z direction occur where the electrode width Δ(x) or Δ(y) equals the half wave frequency of the acoustic wave generated by the oscillating signal 715. When the oscillator signal 715 scanned from low to high-frequencies, the resonant spot is shifted. The x- and y-tapers are such that the resonant frequency range in each direction does not overlap each other. Therefore scanning the EM source modulation frequency yields two-dimensional spatial distribution of the incident EM radiation.

In another embodiment, the band-pass filter 710 in FIG. 7B can be replaced with a frequency detecting electronic circuit and the signal 714 yields change in modulation frequency due to presence of incident radiation, and yields the spatial and amplitude distribution of the incident EM radiation.

In another embodiment, the band-pass filter 710 in FIG. 7B can be replaced with a phase detecting electronic circuit and the signal 714 yields change in phase of the modulation signal due to presence of incident radiation, and yields the spatial and amplitude distribution of the incident EM radiation.

Yet in another embodiment the tapered electrode 705 in FIG. 7B, the overlaying absorptive coating 703, the piezoelectric layer 706 and the ground plane 707 can be of any arbitrary shape that span any range of frequencies to yield spatial distribution of the incident radiation. Specific shape parameters are application-specific, and are chosen considering image size, resolution.

Figure 8A:
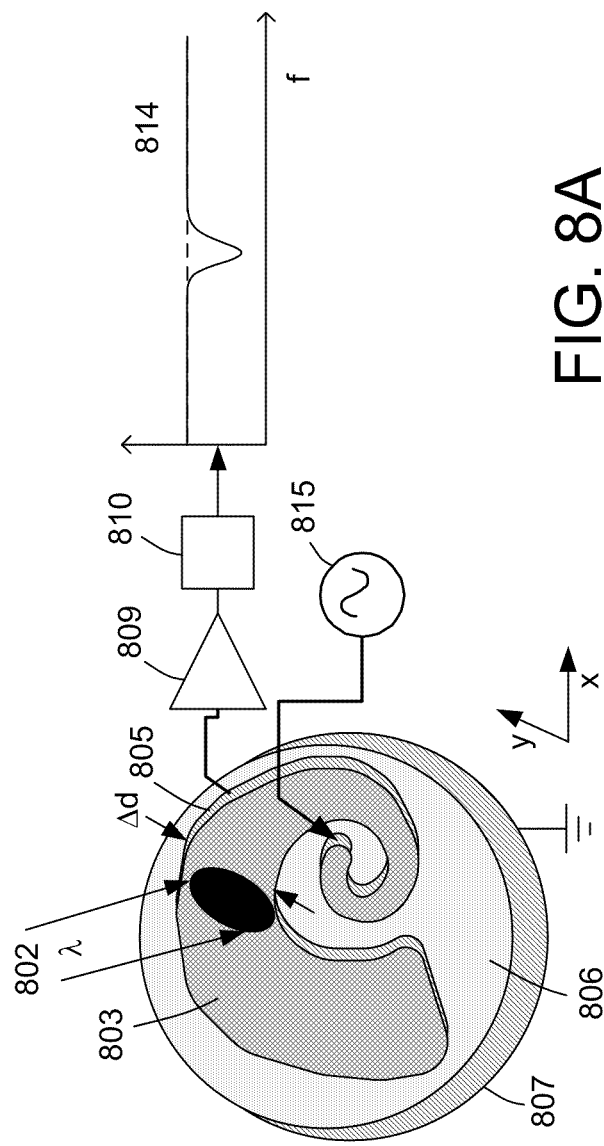

Referring to FIG. 8A, a perspective pictorial and block diagram illustrates an embodiment of a sensor configured for two-dimensional photo-acoustic imaging of broadband electromagnetic radiation. A piezoelectric layer 806 is sandwiched between an electrode 805 and a ground plane 807. The electrode is coated with a wide-band EM absorbing layer 803, such as a carbon coating or a black paint. A modulation signal 815 is applied to the electrode 805. The signal is scanned from low to high frequencies. The spiral electrode 805 is formed to be narrow on one side, and wider on the other. When a modulation frequency 815 is applied to the electrode 805, the device oscillates due to the piezoelectric effect. A high-gain, low-noise amplifier 809 is connected to the electrode 805, followed by a band-pass filter 810. The maximum expansion and contraction of the layers in z direction occur where the electrode width d equals the half wave frequency of the acoustic wave generated by the oscillating signal 815. When the oscillator signal 815 scanned from low to high-frequencies, the resonant spot is shifted. At the presence of an incident EM radiation 802, the amplitude as well as frequency of vibration is altered. The maximum change occurs when radiation is incident on the resonant spot, resulting in change in amplitude in the signal 814, thus indicating the spatial distribution of the resonant incident radiation. The change in amplitude is dependent on the incident radiation intensity and location, and therefore the signal 814 yields both intensity and spatial distribution of the incident radiation.

In another embodiment, the band-pass filter 810 in FIG. 8A can be replaced with a frequency detecting electronic circuit and the signal 814 yields change in modulation frequency due to presence of incident radiation, and yields the spatial and amplitude distribution of the incident EM radiation.

In another embodiment, the band-pass filter 810 in FIG. 8A can be replaced with a phase detecting electronic circuit and the signal 814 yields change in phase of the modulation signal due to presence of incident radiation, and yields the spatial and amplitude distribution of the incident EM radiation.

Yet in another embodiment the tapered electrode 805 in FIG. 8A, the overlaying absorptive coating 803, the piezoelectric layer 806 and the ground plane 807 can be of any arbitrary shape that span any range of frequencies to yield spatial distribution of the incident radiation. Specific shape parameters are application-specific, and are chosen considering image size, resolution.

Figure 8B:
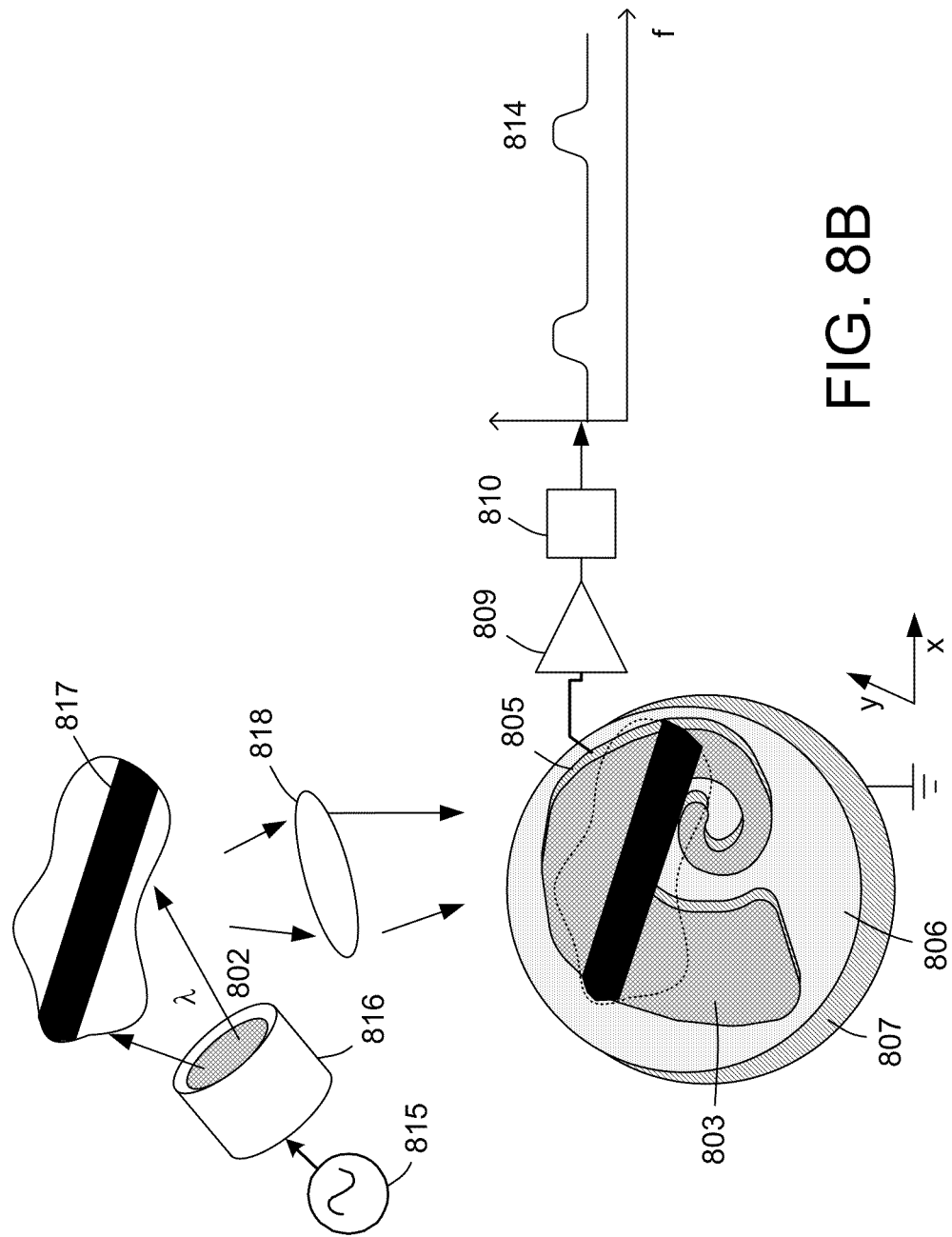

Referring to FIG. 8B, a perspective pictorial and block diagram illustrates an embodiment of a sensor configured for two-dimensional photo-acoustic imaging of broadband electromagnetic radiation. A piezoelectric layer 806 is sandwiched between an electrode 805 and a ground plane 807. The electrode is coated with a wide-band EM absorbing layer 803, such as a carbon coating or a black paint. The methodology is similar to that of FIG. 7A, however instead of applying the modulation signal to the electrodes 805, the EM source 816 which illuminates an object 817 is modulated. The modulated EM radiation reflects from the surface of objects, carrying spatial information about the object reflection. An optional lens 818 or imaging optics is used to focus the reflected or scattered EM radiation from the object 817 onto the sensor absorbing surface 803. The electrode 805 is connected to a high-gain, low-noise amplifier 809 and to an optional band-pass filter 810 to filter out unwanted noise. The detected signal 814 is displayed in a frequency plot. The signal has highest modulation amplitude when the source modulation frequency matches the resonant frequency of sensor at a particular location, which is controlled by the width d. The maximum expansion and contraction of the layers in z direction occur where the electrode width d equals the half wave frequency of the acoustic wave generated by the oscillating signal 815. When the oscillator signal 815 scanned from low to high-frequencies, the resonant spot is shifted. The spiral electrode tapers such that the resonant frequency range in each direction does not overlap each other. Therefore scanning the EM source modulation frequency yields two-dimensional spatial distribution of the incident EM radiation.

In another embodiment, the band-pass filter 810 in FIG. 8B can be replaced with a frequency detecting electronic circuit and the signal 814 yields change in modulation frequency due to presence of incident radiation, and yields the spatial and amplitude distribution of the incident EM radiation.

In another embodiment, the band-pass filter 810 in FIG. 8B can be replaced with a phase detecting electronic circuit and the signal 814 yields change in phase of the modulation signal due to presence of incident radiation, and yields the spatial and amplitude distribution of the incident EM radiation.

In another embodiment the tapered electrode 805 in FIG. 8B, the overlaying absorptive coating 803, the piezoelectric layer 806 and the ground plane 807 can be of any arbitrary shape that will span any range of frequencies to yield spatial distribution of the incident radiation. Specific shape parameters are application-specific, and are chosen considering image size, resolution.

Referring to FIG. 9A, a perspective pictorial and block diagram illustrates an embodiment of a sensor configured for one-dimensional photo-acoustic imaging of broadband electromagnetic radiation. Two piezoelectric layers 906 are sandwiched between three electrodes 905a, 905b and 905c. The electrode is coated with a wide-band EM absorbing layer 903, such as a carbon coating or a black paint. A modulation signal 915 is applied to one of the electrodes 905a. The signal is scanned from low to high frequencies. One or more of the electrode 905a, 905-b, and 905c is tapered such that it is narrow on one side and wider on the other. When a modulation frequency 915 is applied to the electrode 905a, the device oscillates due to the piezoelectric effect. A high-gain, low-noise amplifier 909 is connected to electrode 905c, followed by a band-pass filter 910. The maximum expansion and contraction of the layers in z direction occur where the electrode width $\Delta(x)$ equals the half wave frequency of the acoustic wave generated by the oscillating signal 915. When the frequency is scanned, the resonant spot is shifted. At the presence of an incident EM radiation 902, the amplitude as well as frequency of vibration is altered. The maximum change occurs when radiation is incident on the resonant spot. This yields change in amplitude in the signal 914, thus indicating the spatial distribution of the resonant incident radiation. The change in amplitude is dependent on the incident radiation intensity and location, and therefore the signal 914 yields both intensity and spatial distribution of the incident radiation. Electrode 905a, 905b and 905c, and the signal 915 connection and amplifier 909 can be connected at any order.

In another embodiment, the band-pass filter 910 in FIG. 9A can be replaced with a frequency detecting electronic circuit and the signal 914 yields change in modulation frequency due to presence of incident radiation, and yields the spatial and amplitude distribution of the incident EM radiation.

In another embodiment, the band-pass filter 910 in FIG. 9A can be replaced with a phase detecting electronic circuit and the signal 914 yields change in phase of the modulation signal due to presence of incident radiation, and yields the spatial and amplitude distribution of the incident EM radiation.

Yet in another embodiment the tapered electrode 905 in FIG. 9A, the overlaying absorptive coating 903, the piezoelectric layer 906 and the ground plane 907 can be of any arbitrary shape that will span any range of frequencies to yield spatial distribution of the incident radiation. Specific shape parameters are application-specific, and are chosen considering image size, resolution.

Referring to FIG. 9B, a perspective pictorial and block diagram illustrates an embodiment of a sensor configured for one-dimensional photo-acoustic imaging of broadband electromagnetic radiation. The sensor is similar to the FIG. 9A configuration, however the amplifier 909 can be replaced with a differential amplifier 909b. The differential amplifier serves several purposes including subtracting the signal due to modulation combined with illumination caused change in amplitude and frequency. The differential amplifier 909b also subtracts background noise due to external vibrations. Two piezoelectric layers 906 are sandwiched between three electrodes 905a, 905b and 905c. The electrode is coated with a wide-band EM absorbing layer 903, such as a carbon coating or a black paint. A modulation signal 915 is applied to one of the electrodes 905a. The signal is scanned from low to high frequencies. One or more of the electrode 905a, 905-b, and 905c is tapered such that it is narrow on one side and wider on the other. When a modulation frequency 915 is applied to the electrode 905a, the device oscillates due to the piezoelectric effect. A high-gain, low-noise amplifier 909b is connected to two electrode 905a and 905c, followed by a band-pass filter 910. The maximum expansion and contraction of the layers in z direction occur where the electrode width $\Delta(x)$ equals the half wave frequency of the acoustic wave generated by the oscillating signal 915. When the frequency is scanned, the resonant spot is shifted. At the presence of an incident EM radiation 902, the amplitude as well as frequency of vibration is altered. The maximum change occurs when radiation is incident on the resonant spot, yielding change in amplitude in the signal 914, thus indicating the spatial distribution of the resonant incident radiation. The change in amplitude is dependent on the incident radiation intensity and location, and therefore the signal 914 yields both intensity and spatial distribution of the incident radiation. Electrode 905a, 905b and 905c, and the signal 915 connection and amplifier 909a can be connected at any order.

In another embodiment, the band-pass filter 910 in FIG. 9B can be replaced with a frequency detecting electronic circuit and the signal 914 yields change in modulation frequency due to presence of incident radiation, and yields the spatial and amplitude distribution of the incident EM radiation.

In another embodiment, the band-pass filter 910 in FIG. 9B can be replaced with a phase detecting electronic circuit and the signal 914 yields change in phase of the modulation signal due to presence of incident radiation, and yields the spatial and amplitude distribution of the incident EM radiation.

Yet in another embodiment the tapered electrode 905 in FIG. 9B, the overlaying absorptive coating 903, the piezoelectric layer 906 and the ground plane 907 can be of any arbitrary shape that will span any range of frequencies to yield spatial distribution of the incident radiation. Specific shape parameters are application-specific, and are chosen considering image size, resolution.

Figure 9C:
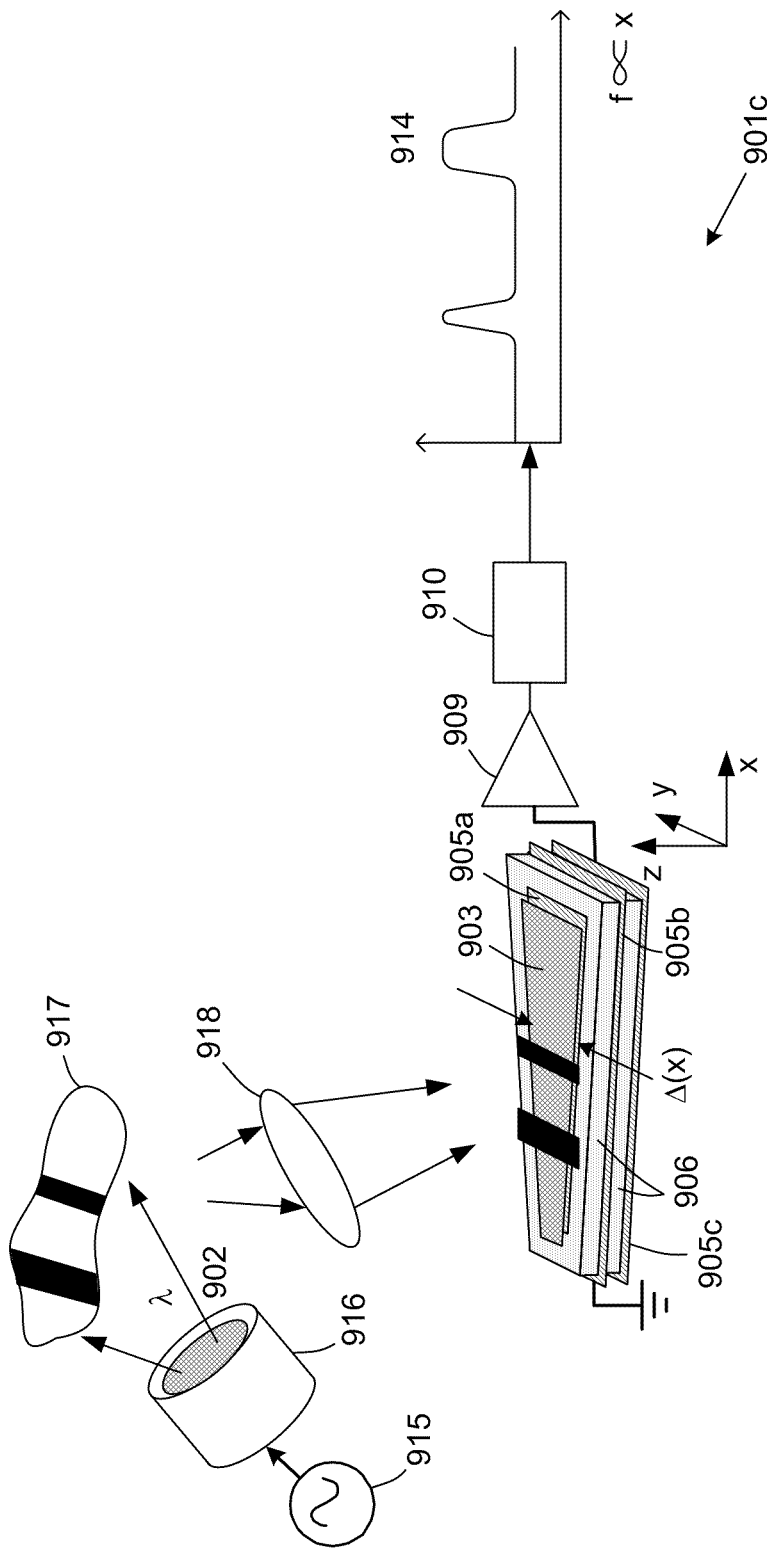

Referring to FIG. 9C, a perspective pictorial and block diagram illustrates an embodiment of a sensor configured for one-dimensional photo-acoustic imaging of broadband electromagnetic radiation. The methodology is similar to that described with respect to FIG. 9A, however, instead of applying the modulation signal to the electrode 905a, the EM source 916 which illuminates an object 917 is modulated. The modulated EM radiation reflects from the surface of objects, carrying spatial information about the object. An optional lens 918 or imaging optics is used to focus the reflected or scattered EM radiation from the object 917 onto the sensor absorbing surface 903. The electrodes 905b and 905c are connected to a high-gain, low-noise differential amplifier 909 and to an optional band-pass filter to filter out unwanted noise. The detected signal 914 is displayed in a frequency plot. The signal has highest modulation amplitude when the source modulation frequency matches the resonant frequency of the spot in x direction, which is controlled by the width $\Delta(x)$ of the tapered electrode 905a. Therefore scanning the frequency yields the spatial and amplitude distribution of the incident radiation, namely object reflection. Electrode 905a, 905b and 905c, and the signal 915 connection and amplifier 909a can be connected at any order.

In another embodiment, the band-pass filter 910 in FIG. 9C can be replaced with a frequency detecting electronic circuit and the signal 914 yields change in modulation frequency due to presence of incident radiation, and yields the spatial and amplitude distribution of the incident EM radiation.

In another embodiment, the band-pass filter 910 in FIG. 9C can be replaced with a phase detecting electronic circuit and the signal 914 yields change in phase of the modulation signal due to presence of incident radiation, and yields the spatial and amplitude distribution of the incident EM radiation.

Yet in another embodiment the tapered electrode 905 in FIG. 9C, the overlaying absorptive coating 903, the piezoelectric layer 906 and the ground plane 907 can be of any arbitrary shape that will span any range of frequencies to yield spatial distribution of the incident radiation. Specific shape parameters are application-specific, and are chosen considering image size, resolution.

Figure 9D:
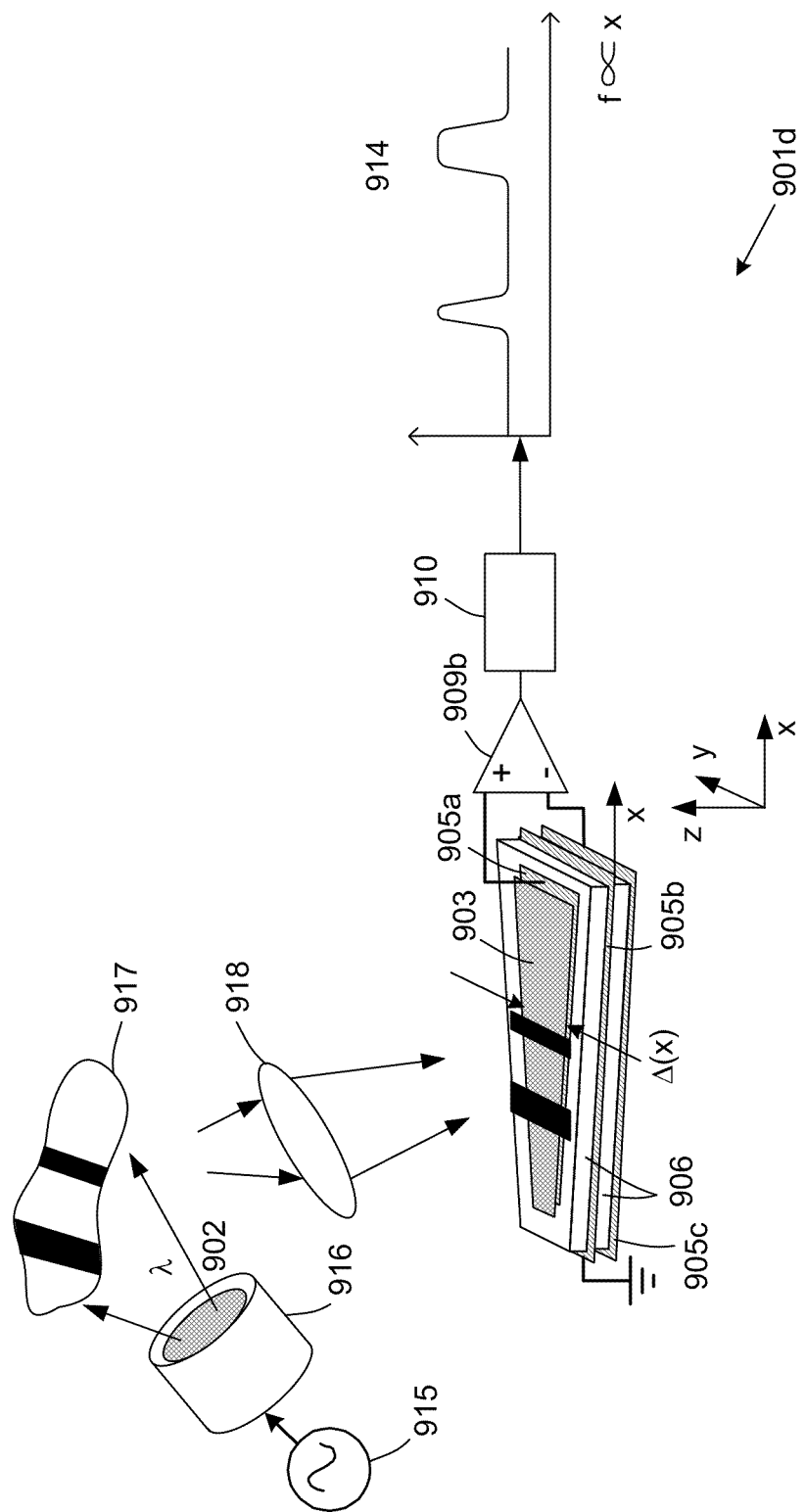

Referring to FIG. 9D, a perspective pictorial and block diagram illustrates an embodiment of a sensor configured for one-dimensional photo-acoustic imaging of broadband electromagnetic radiation. The methodology is similar to that with respect to FIG. 9B, however, instead of applying the modulation signal to the electrode 905a, the EM source 916 which illuminates an object 917 is modulated. The modulated EM radiation reflects from the surface of objects, carrying spatial information about the object. An optional lens 918 or imaging optics is used to focus the reflected or scattered EM radiation from the object 917 onto the sensor absorbing surface 903. The electrodes 905b and 905c are connected to a high-gain, low-noise differential amplifier 909b and to an optional band-pass filter to filter out unwanted noise. The detected signal 914 is displayed in a frequency plot. The signal has highest modulation amplitude when the source modulation frequency matches the resonant frequency of the spot in x direction, which is controlled by the width $\Delta(x)$ of the tapered electrode 905a. Therefore scanning the frequency yields the spatial and amplitude distribution of the incident radiation, namely object reflection. Electrode 905a, 905b and 905c, and the signal 915 connection and amplifier 909a can be connected at any order.

In another embodiment, the band-pass filter 910 in FIG. 9D can be replaced with a frequency detecting electronic circuit and the signal 914 yields change in modulation frequency due to presence of incident radiation, and yields the spatial and amplitude distribution of the incident EM radiation.

In another embodiment, the band-pass filter 910 in FIG. 9D can be replaced with a phase detecting electronic circuit and the signal 914 yields change in phase of the modulation signal due to presence of incident radiation, and yields the spatial and amplitude distribution of the incident EM radiation.

Yet in another embodiment the tapered electrode 905 in FIG. 9D, the overlaying absorptive coating 903, the piezoelectric layer 906 and the ground plane 907 can be of any arbitrary shape that will span any range of frequencies to yield spatial distribution of the incident radiation. Specific shape parameters are application-specific, and are chosen considering image size, resolution.

Figure 10A:
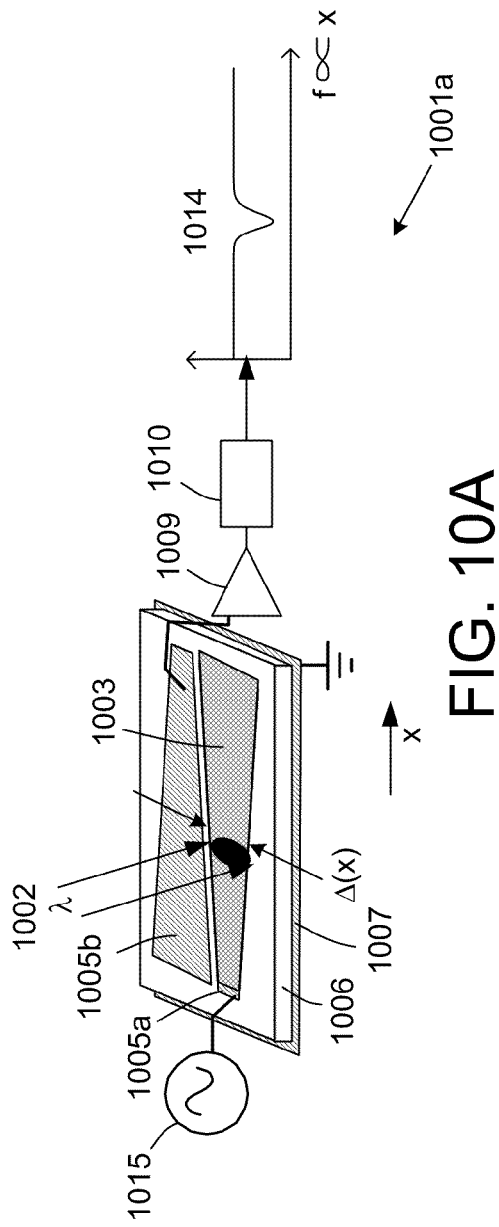

Referring to FIG. 10A, a perspective pictorial and block diagram illustrates an embodiment of a sensor configured for one-dimensional photo-acoustic imaging of broadband electromagnetic radiation. A piezoelectric layer 1006 is sandwiched between two top electrodes 1005*a*, and 1005*b* and a ground plane 1007. One of the electrodes 1005*a* is coated with a wide-band EM absorbing layer 1003, such as a carbon coating or a black paint. A modulation signal 1015 is applied to one of the electrodes 1005*a*. The signal is scanned from low to high frequencies. One or more of the electrode 1005*a* and 1005*b* is tapered such that it is narrow on one side and wider on the other. When a modulation frequency 1015 is applied to the electrode 1005*a*, the device oscillates due to the piezoelectric effect. A high-gain, low-noise amplifier 1009 is connected to electrode 1005*b*, followed by a band-pass filter 1010. The maximum expansion and contraction of the layers in z direction occur where the electrode width Δ(x) equals the half wave frequency of the acoustic wave generated by the oscillating signal 1015. When the frequency is scanned, the resonant spot is shifted. At the presence of an incident EM radiation 1002, the amplitude as well as frequency of vibration is altered. The maximum change occurs when radiation is incident on the resonant spot, yielding a change in amplitude in the signal 1014, thus indicating the spatial distribution of the resonant incident radiation. The change in amplitude is dependent on the incident radiation intensity and location, and therefore the signal 1014 yields both intensity and spatial distribution of the incident radiation. Electrode 1005*a*, 1005*b* and 1005*c*, and the signal 1015 connection and amplifier 1009 can be connected at any order.

In another embodiment, the band-pass filter 1010 in FIG. 10A can be replaced with a frequency detecting electronic circuit and the signal 1014 yields change in modulation frequency due to presence of incident radiation, and yields the spatial and amplitude distribution of the incident EM radiation.

In another embodiment, the band-pass filter 1010 in FIG. 10A can be replaced with a phase detecting electronic circuit and the signal 1014 yields change in phase of the modulation signal due to presence of incident radiation, and yields the spatial and amplitude distribution of the incident EM radiation.

Yet in another embodiment the tapered electrode 1005*a* and 1005*b* in FIG. 10A, the overlaying absorptive coating 1003, the piezoelectric layer 1006 and the ground plane 1007 can be of any arbitrary shape that will span any range of frequencies to yield spatial distribution of the incident radiation. Specific shape parameters are application-specific, and are chosen considering image size, resolution.

Figure 10B:
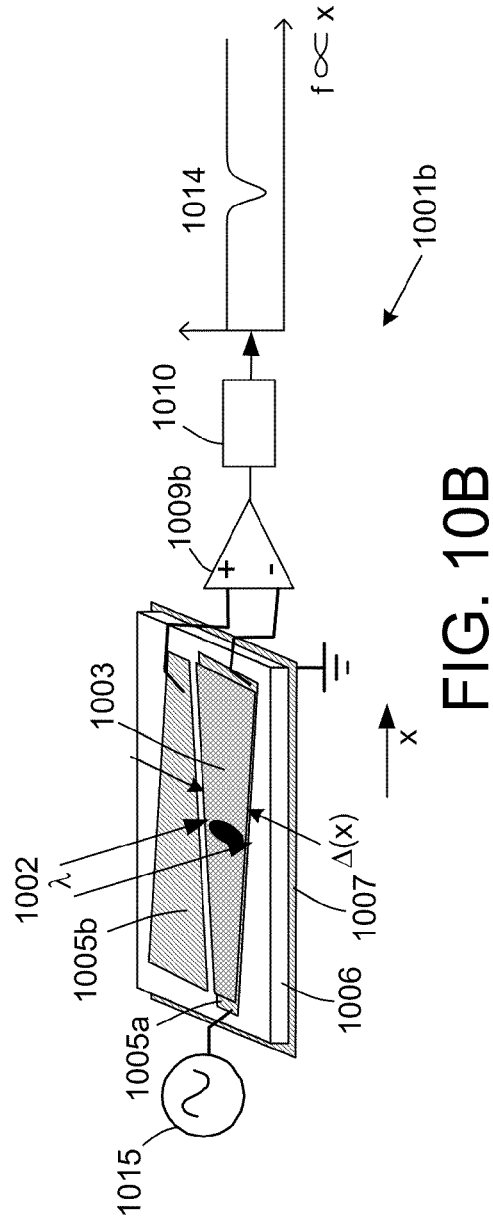

Referring to FIG. 10B, a perspective pictorial and block diagram illustrates an embodiment of a sensor configured for one-dimensional photo-acoustic imaging of broadband electromagnetic radiation. The sensor is similar to FIG. 10A configuration, however the amplifier 1009 can be replaced with a differential amplifier 1009*b*. The differential amplifier serves several purposes including subtracting the signal due to modulation combined with illumination caused change in amplitude and frequency, and also subtracting background noise due to external vibrations. A piezoelectric layer 1006 is sandwiched between two top electrodes 1005*a*, and 1005*b* and a ground plane 1007. One of the electrodes 1005*a* is coated with a wide-band EM absorbing layer 1003, such as a carbon coating or a black paint. A modulation signal 1015 is applied to one of the electrodes 1005*a*. The signal is scanned from low to high frequencies. One or more of the electrode 1005*a* and 1005*b* is tapered such that it is narrow on one side and wider on the other. When a modulation frequency 1015 is applied to the electrode 1005*a*, the device oscillates due to the piezoelectric effect. A high-gain, low-noise amplifier 1009 is connected to electrode 1005*b*, followed by a band-pass filter 1010. The maximum expansion and contraction of the layers in z direction occur where the electrode width Δ(x) equals the half wave frequency of the acoustic wave generated by the oscillating signal 1015. When the frequency is scanned, the resonant spot is shifted. At the presence of an incident EM radiation 1002, the amplitude as well as frequency of vibration is altered. The maximum change occurs when radiation is incident on the resonant spot. This yields change in amplitude in the signal 1014, thus indicating the spatial distribution of the resonant incident radiation. The change in amplitude is dependent on the incident radiation intensity and location, and therefore the signal 1014 yields both intensity and spatial distribution of the incident radiation. Electrode 1005*a*, 1005*b* and 1005*c*, and the signal 1015 connection and amplifier 1009 can be connected at any order.

In another embodiment, the band-pass filter 1010 in FIG. 10B can be replaced with a frequency detecting electronic circuit and the signal 1014 yields change in modulation frequency due to presence of incident radiation, and yields the spatial and amplitude distribution of the incident EM radiation.

In another embodiment, the band-pass filter 1010 in FIG. 10B can be replaced with a phase detecting electronic circuit and the signal 1014 yields change in phase of the modulation signal due to presence of incident radiation, and yields the spatial and amplitude distribution of the incident EM radiation.

Yet in another embodiment the tapered electrode 1005*a* and 1005*b* in FIG. 10B, the overlaying absorptive coating 1003, the piezoelectric layer 1006 and the ground plane 1007 can be of any arbitrary shape that will span any range of frequencies to yield spatial distribution of the incident radiation. Specific shape parameters are application-specific, and are chosen considering image size, resolution.

Figure 10C:
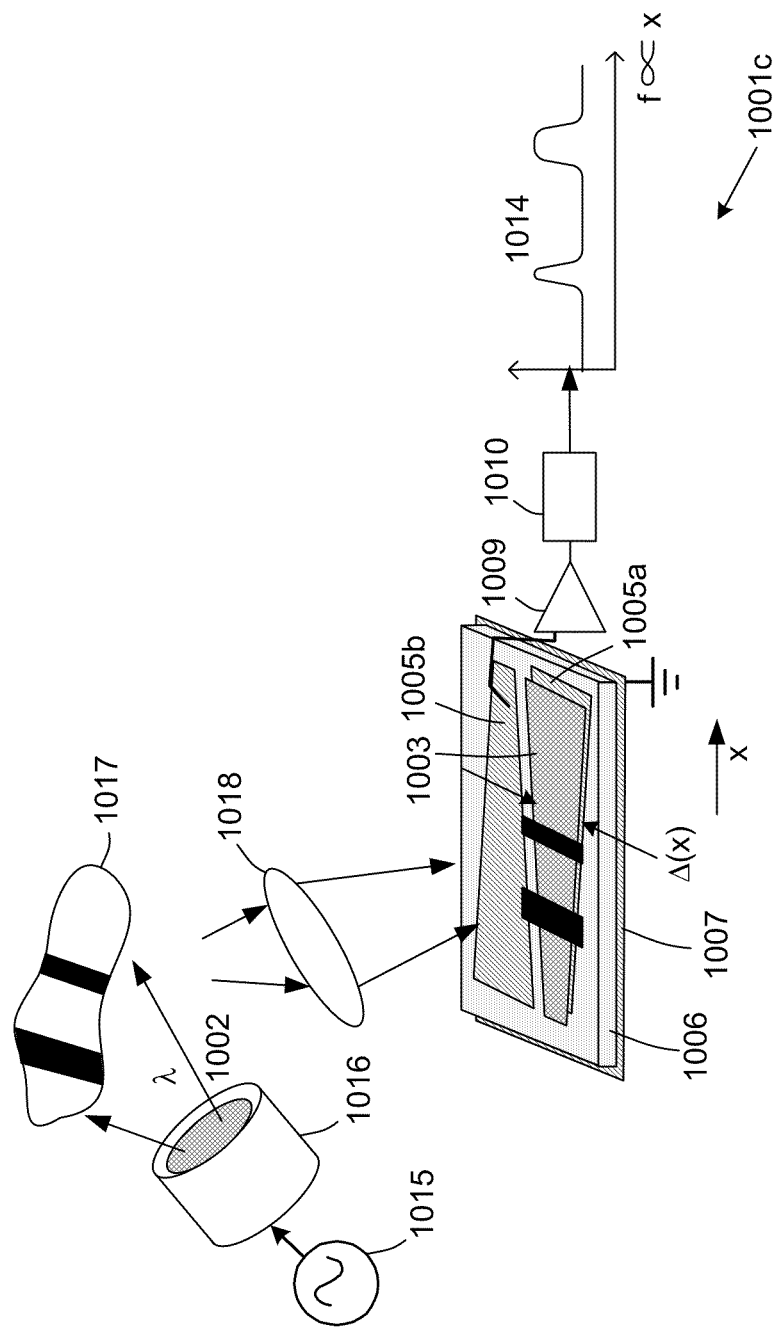

Referring to FIG. 10C, a perspective pictorial and block diagram illustrates an embodiment of a sensor configured for one-dimensional photo-acoustic imaging of broadband electromagnetic radiation. The methodology is similar to that of FIG. 10A, however, instead of applying the modulation signal to the electrode 1005*a*, the EM source 1016 which illuminates an object 1017 is modulated. The modulated EM radiation reflects from the surface of objects, carrying spatial information about the object. An optional lens 1018 or imaging optics is used to focus the reflected or scattered EM radiation from the object 1017 onto the sensor absorbing surface 9-3. A piezoelectric layer 1006 is sandwiched between two top electrodes 1005*a*, and 1005*b* and a ground plane 1007. One of the electrodes 1005*a* is coated with a wide-band EM absorbing layer 1003, such as a carbon coating or a black paint. A modulation signal 1015 is applied to one of the electrodes 1005*a*. The signal is scanned from low to high frequencies. One or more of the electrode 1005*a* and 1005-*b* is tapered such that it is narrow on one side and wider on the other. When a modulation frequency 1015 is applied to the electrode 1005*a*, the device oscillates due to the piezoelectric effect. A high-gain, low-noise amplifier 1009 is connected to electrode 1005*b*, followed by a band-pass filter 1010. The maximum expansion and contraction of the layers in z direction occur where the electrode width Δ(x) equals the half wave frequency of the acoustic wave generated by the oscillating signal 1015. When the frequency is scanned, the resonant spot is shifted. At the presence of an incident EM radiation 1002, the amplitude as well as frequency of vibration is altered. The maximum change occurs when radiation is incident on the resonant spot. This yields change in amplitude in the signal 1014, thus indicating the spatial distribution of the resonant incident radiation. The change in amplitude is dependent on the incident radiation intensity and location, and therefore the signal 1014 yields both intensity and spatial distribution of the incident radiation. Electrode 1005a, 1005b and 1005c, and the signal 1015 connection and amplifier 1009 can be connected at any order.

In another embodiment, the band-pass filter 1010 in FIG. 10C can be replaced with a frequency detecting electronic circuit and the signal 1014 yields change in modulation frequency due to presence of incident radiation, and yields the spatial and amplitude distribution of the incident EM radiation.

In another embodiment, the band-pass filter 1010 in FIG. 10C can be replaced with a phase detecting electronic circuit and the signal 1014 yields change in phase of the modulation signal due to presence of incident radiation, and yields the spatial and amplitude distribution of the incident EM radiation.

Yet in another embodiment the tapered electrode 1005a and 1005b in FIG. 10C, the overlaying absorptive coating 1003, the piezoelectric layer 1006 and the ground plane 1007 can be of any arbitrary shape that will span any range of frequencies to yield spatial distribution of the incident radiation. Specific shape parameters are application-specific, and are chosen considering image size, resolution.

Figure 10D:
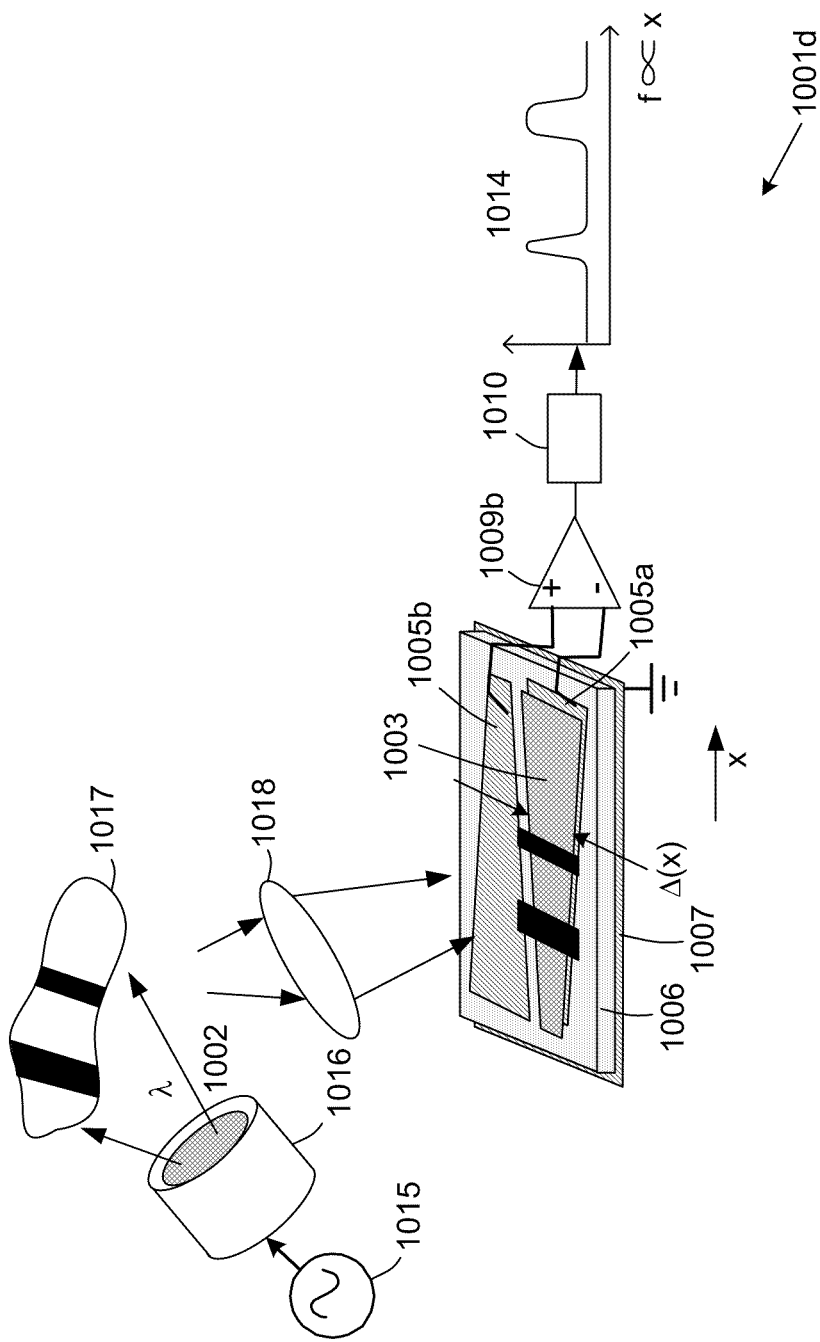

Referring to FIG. 10D, a perspective pictorial and block diagram illustrates an embodiment of a sensor configured for one-dimensional photo-acoustic imaging of broadband electromagnetic radiation. The methodology is similar to that with respect to FIG. 10B, however, instead of applying the modulation signal to the electrode 1005a, the EM source 1016 which illuminates an object 1017 is modulated. The modulated EM radiation reflects from the surface of objects, carrying spatial information about the object. An optional lens 1018 or imaging optics is used to focus the reflected or scattered EM radiation from the object 1017 onto the sensor absorbing surface 1003. The differential amplifier 1009b serves several purposes. It subtracts the signal due to modulation combined with illumination caused change in amplitude and frequency. It also subtracts background noise due to external vibrations. A piezoelectric layer 1006 is sandwiched between two top electrodes 1005a, and 1005b and a ground plane 1007. One of the electrodes 1005a is coated with a wide-band EM absorbing layer 1003, such as a carbon coating or a black paint. A modulation signal 1015 is applied to one of the electrodes 1005a. The signal is scanned from low to high frequencies. One or more of the electrode 1005a and 1005b is tapered such that it is narrow on one side and wider on the other. When a modulation frequency 1015 is applied to the electrode 1005a, the device oscillates due to the piezoelectric effect. A high-gain, low-noise amplifier 1009 is connected to electrode 1005b, followed by a band-pass filter 1010. The maximum expansion and contraction of the layers in z direction occur where the electrode width $\Delta(x)$ equals the half wave frequency of the acoustic wave generated by the oscillating signal 1015. When the frequency is scanned, the resonant spot is shifted. At the presence of an incident EM radiation 1002, the amplitude as well as frequency of vibration is altered. The maximum change occurs when radiation is incident on the resonant spot. This yields change in amplitude in the signal 1014, thus indicating the spatial distribution of the resonant incident radiation. The change in amplitude is dependent on the incident radiation intensity and location, and therefore the signal 1014 yields both intensity and spatial distribution of the incident radiation. Electrode 1005a, 1005b and 1005c, and the signal 1015 connection and amplifier 1009 can be connected at any order.

In another embodiment, the band-pass filter 1010 in FIG. 10D can be replaced with a frequency detecting electronic circuit and the signal 1014 yields change in modulation frequency due to presence of incident radiation, and yields the spatial and amplitude distribution of the incident EM radiation.

In another embodiment, the band-pass filter 1010 in FIG. 10D can be replaced with a phase detecting electronic circuit and the signal 1014 yields change in phase of the modulation signal due to presence of incident radiation, and yields the spatial and amplitude distribution of the incident EM radiation.

Yet in another embodiment the tapered electrode 1005a and 1005b in FIG. 10D, the overlaying absorptive coating 1003, the piezoelectric layer 1006 and the ground plane 1007 can be of any arbitrary shape that will span any range of frequencies to yield spatial distribution of the incident radiation. Specific shape parameters are application-specific, and are chosen considering image size, resolution.

Referring to FIG. 11A, a perspective pictorial and block diagram illustrates an embodiment of a sensor configured for one-dimensional photo-acoustic imaging of broadband electromagnetic radiation. A piezoelectric layer 1106 is sandwiched between an electrode 1105 and a ground plane 1107. The electrode is coated with a wide-band EM absorbing layer 1103, such as a carbon coating or a black paint. The single element sensor head 1119 is connected to an amplifier 1109 and an optional low-pass or band-pass filter 1110 to remove unwanted noise. One dimensional scanning is achieved by moving the object 1117 with respect to the sensor head 1119. An optional lens 1118 or imaging optics can be used, which is also stationary with respect to the moving object 1117. Scanning the object 1117 yields a signal 1114 that varies in time due to movement of the object 1117.

Referring to FIG. 11B, a perspective pictorial and block diagram illustrates an embodiment of a sensor configured for one-dimensional photo-acoustic imaging of broadband electromagnetic radiation. A piezoelectric layer 1106 is sandwiched between an electrode 1105 and a ground plane 1107. The electrode is coated with a wide-band EM absorbing layer 1103, such as a carbon coating or a black paint. The single element sensor head 1119 is connected to an amplifier 1109 and an optional low-pass or band-pass filter 1110 to remove unwanted noise. One dimensional scanning is achieved by moving or scanning the imaging optics 11-18 with respect to the object. Scanning can be achieved either by linear translation of the imaging optics, such as a lens, or by tilting a mirror that illuminates the object. Scanning the imaging optics 1118, or object illumination optics (not shown), or any combination thereof yields a signal 1114 that varies in time due to movement of the object 1117.

In other embodiments the object 1117 of FIGS. 11A and 11B may be the source of the EM radiation 1102, or the radiation 1102 can be illuminated by an external EM source. The source can be placed such that the object is illuminated for transmission imaging or reflection imaging.

Referring to FIG. 12A, a perspective pictorial and block diagram illustrates an embodiment of a sensor configured for two-dimensional photo-acoustic imaging of broadband electromagnetic radiation. The sensor is similar to the FIG. 11A embodiment and functionality, however the single element sensor head 1119 can be replaced with a one-dimensional sensor element 1219 with the corresponding sensing scheme depicted in FIGS. 1A, 1B, 3, 5A, 5B, 9A, 9B, 9C, 9D, 10A, 10B, 10C, and 10D and in the corresponding text. The one-dimensional sensor head 1219 can be placed in a direction either orthogonal or at any desired angle to the direction of the object scan, and two-dimensional image is obtained. Line scans at various position of the object 1217 are combined to yield the two dimensional image. In an example embodiment image formation is achieved using digital electronics to store the data of each line scan. However, analog scans are also possible in situations where analog electronics is more preferred than using digital electronics.

Referring to FIG. 12B, a perspective pictorial and block diagram illustrates an embodiment of a sensor configured for two-dimensional photo-acoustic imaging of broadband electromagnetic radiation. The sensor is similar to FIG. 11B embodiment and functionality, however the single element sensor head 1119 can be replaced with a one-dimensional sensor element 1219 with the corresponding sensing scheme depicted in FIGS. 1A, 1B, 3, 5A, 5B, 9A, 9B, 9C, 9D, 10A, 10B, 10C, and 10D and in the corresponding text. The one-dimensional sensor head 1219 can be placed in a direction either orthogonal or at any desired angle to the direction of the object scan, and two-dimensional image is obtained. Line scans at various position of the imaging optics 1218, or object illumination optics (not shown), or any combination thereof, are combined to yield a two dimensional image. In a sample embodiment image formation can be achieved using digital electronics to store the data of each line scan. However, analog scans are also possible in situations where analog electronics is more preferred than using digital electronics.

In other embodiments the object 12-17 of FIGS. 12A and 12B may be the source of the EM radiation 12-2, or the radiation can be illuminated by an external EM source. The source can be placed such that the object is illuminated for transmission imaging or reflection imaging.

Figure 14A:
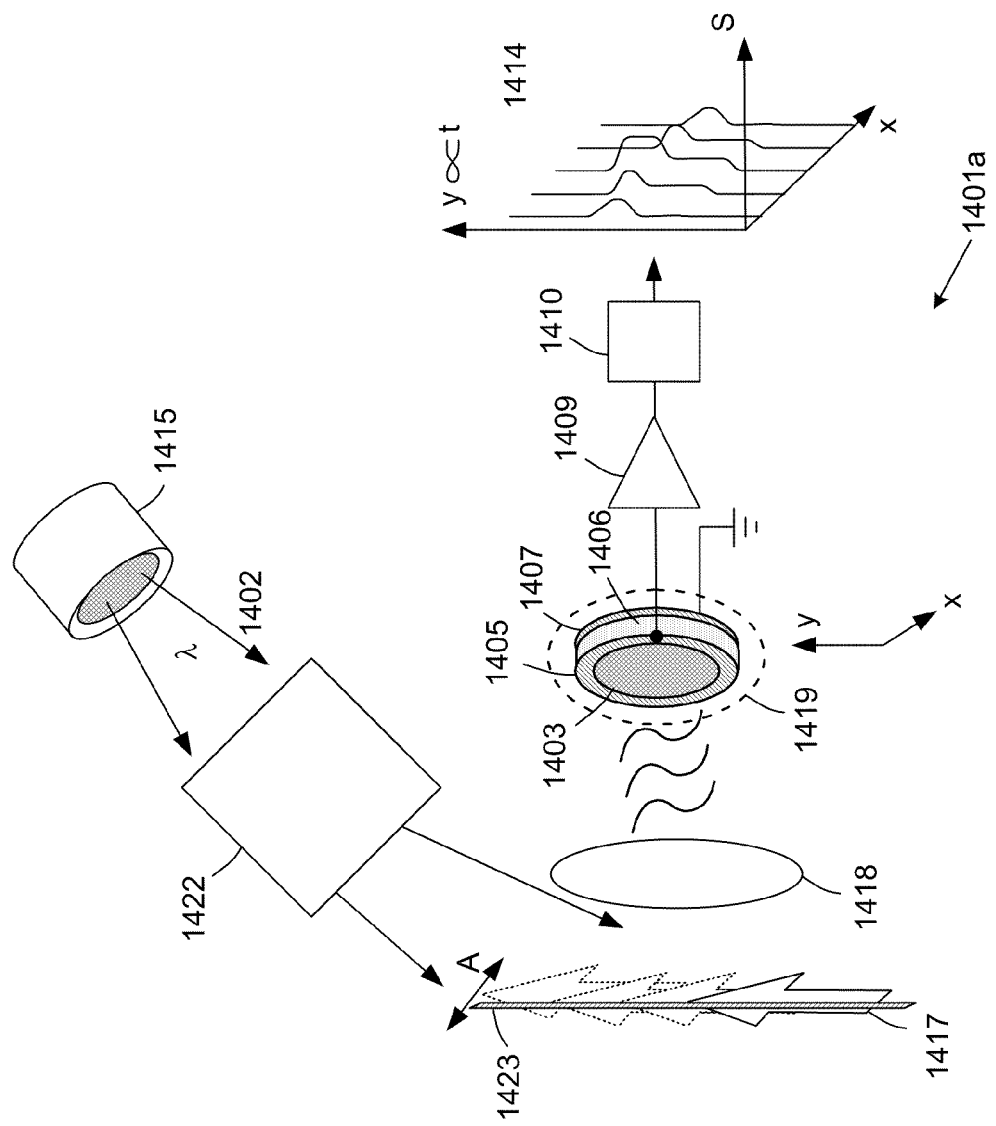
FIGS. 14A through 14C are perspective pictorial and block diagrams illustrating embodiments of sensors configured for two-dimensional photo-acoustic imaging of broadband electromagnetic radiation.

Referring to FIG. 14A, a perspective pictorial and block diagram illustrates an embodiment of a sensor configured for two-dimensional photo-acoustic imaging of broadband electromagnetic radiation. A piezoelectric layer 1406 is sandwiched between an electrode 1405 and a ground plane 1407. The electrode is coated with a wide-band EM absorbing layer 1403, such as a carbon coating or a black paint. The single element sensor head 1419 is connected to an amplifier 1409 and an optional low-pass or band-pass filter 1410 to remove unwanted noise. A line generating apparatus 1422 generates a line illumination 1423 that illuminates the object 1417. The position of the line 1423 can be shifted in direction x as indicated by arrow A by mechanical or electrical control or a combination thereof of the components of the apparatus 1423. At each x-position of the line 1423 a y-scan is performed as described in FIG. 11a, namely by moving the object 1417 in the y-direction. By shifting the x-position of the line 1423, and performing a y-scan by moving the object 1417, a two-dimensional image is scanned. The apparatus 1422 can be composed of diffractive, refractive or reflective optics, and any combination thereof. Line generation from a source can be achieved using such optics. For example in a particular embodiment, a line can be generated from a point source by using a cylindrical lens and an optional spherical lens. For example in a particular embodiment, a line can be generated from laser source or a collimated source by using a cylindrical lens. Other examples of line generating methods include use of curved mirrors such as cylindrical curved mirrors, or mirrors of different curvature in each x and y axis. Scanning of the position of the line 1423 can be achieved in variety of methods, such as using scanning mirrors, by moving the optical components, by moving or tilting the source, or by using electrically controlled components, such as liquid crystal light valves.

In other embodiments digital electronics are used to store the scanned data and display the data once all the scans are complete.

Figure 14B:
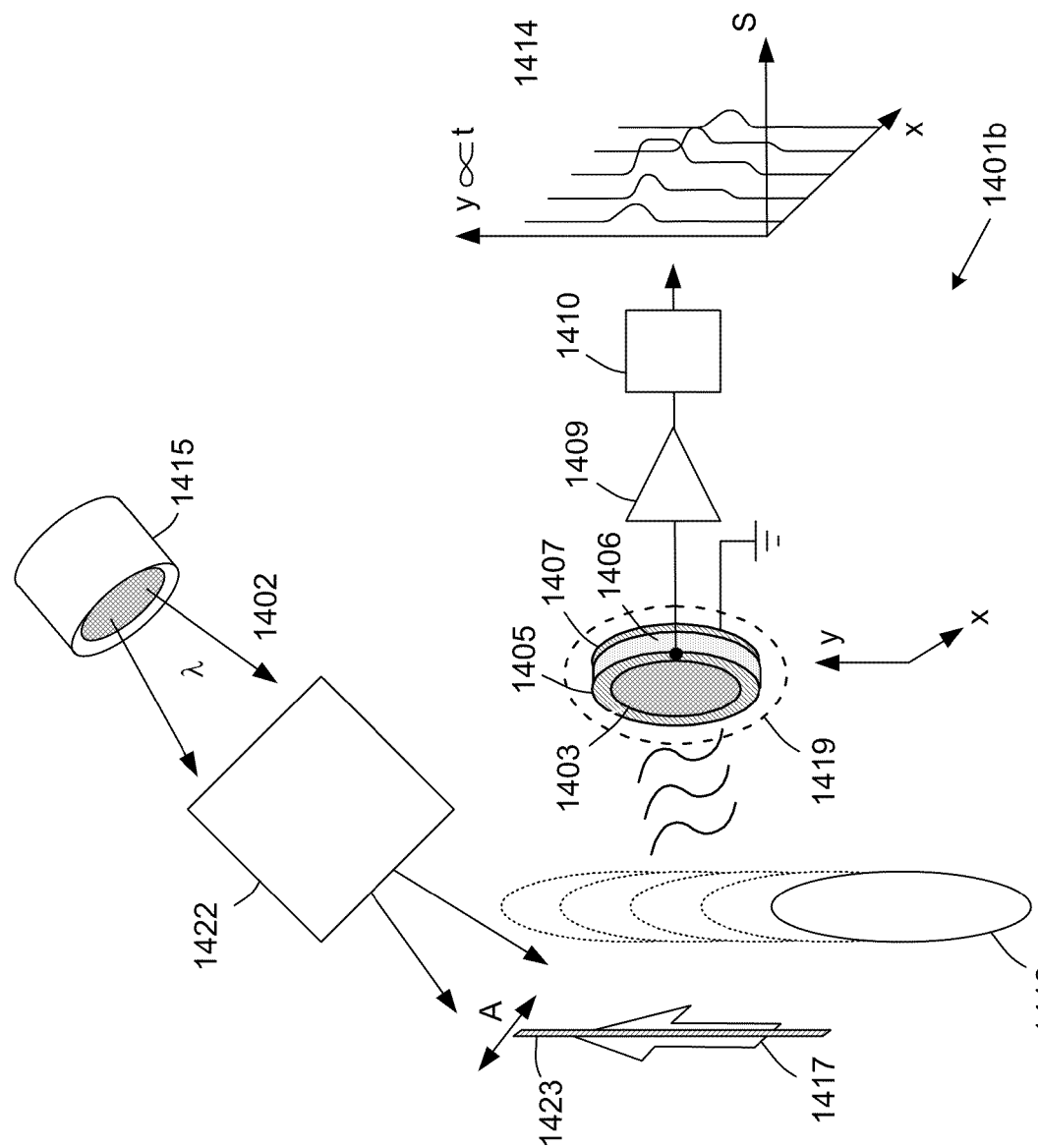

Referring to FIG. 14B, a perspective pictorial and block diagram illustrates an embodiment of a sensor configured for two-dimensional photo-acoustic imaging of broadband electromagnetic radiation. A piezoelectric layer 1406 is sandwiched between an electrode 1405 and a ground plane 1407. The electrode is coated with a wide-band EM absorbing layer 1403, such as a carbon coating or a black paint. This single element sensor head 1419 is connected to an amplifier 1409 and an optional low-pass or band-pass filter 1410 to remove unwanted noise. A line generating apparatus 1422 generates a line illumination 1423 that illuminates the object 1417. The position of the line 1423 can be shifted in direction x as indicated by arrow A by mechanical or electrical control or a combination thereof of the components of the apparatus 1423. At each x-position of the line 1423 a y-scan is performed as described in FIG. 11A, specifically by moving the imaging optics 1418 in the y-direction. By shifting the x-position of the line 1423, and performing a y-scan by moving the object 1417, a two-dimensional image is scanned. The apparatus 1422 can be composed of diffractive, refractive or reflective optics, and any combination thereof. Line generation from a source can be achieved using such optics. For example in a particular embodiment, a line can be generated from a point source by using a cylindrical lens and an optional spherical lens. For example in a particular embodiment, a line can be generated from laser source or a collimated source by using a cylindrical lens. Other examples of line generating methods include use of curved mirrors such as cylindrical curved mirrors, or mirrors of different curvature in each x and y axis. Scanning of the position of the line 1423 can be achieved in variety of methods, such as using scanning mirrors, by moving the optical components, by moving or tilting the source, or by using electrically controlled components, such as liquid crystal light valves.

In other embodiments digital electronics are used to store the scanned data and display the data once all the scans are complete.

Figure 14C:
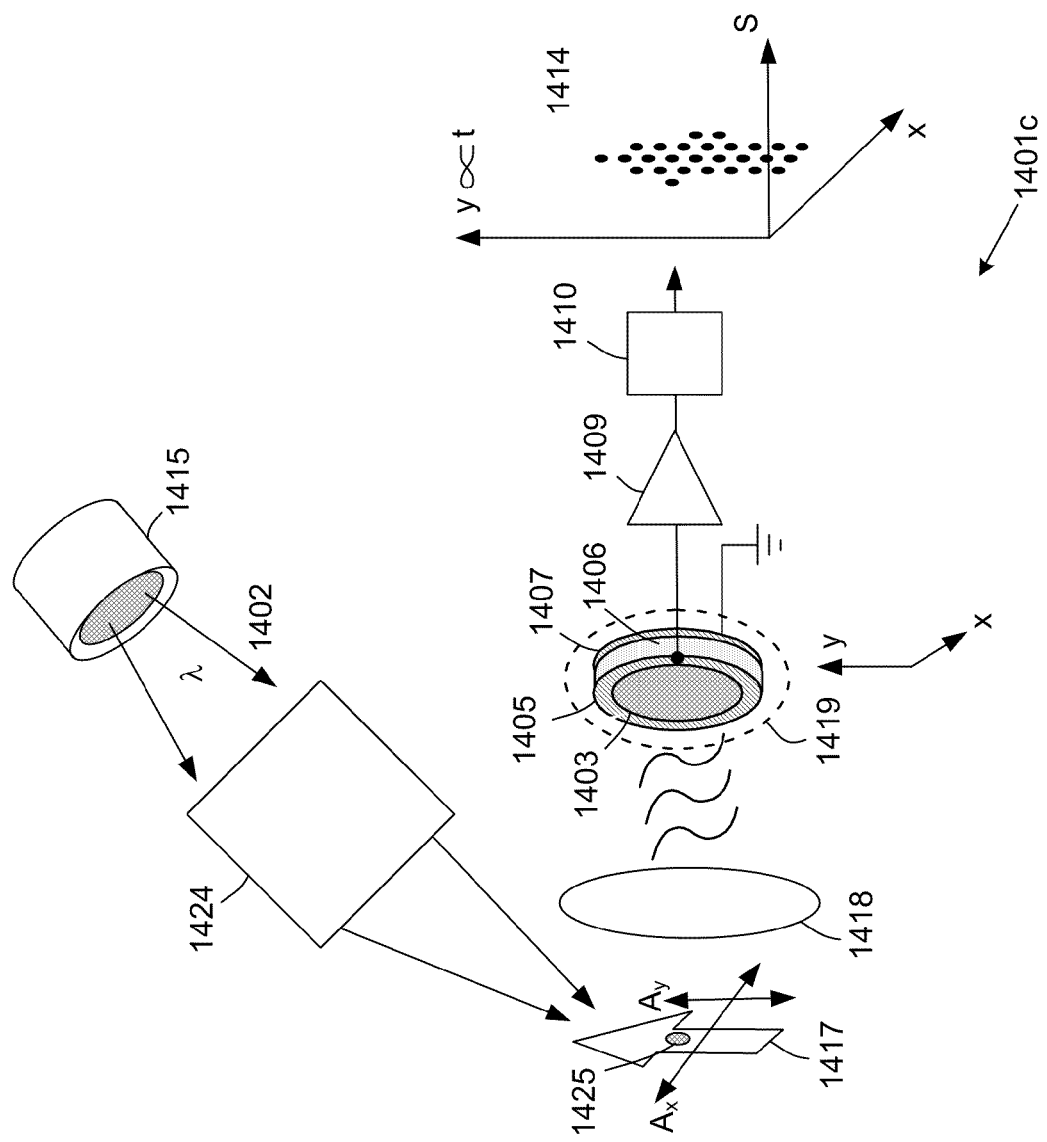

Referring to FIG. 14C, a perspective pictorial and block diagram illustrates an embodiment of a sensor configured for two-dimensional photo-acoustic imaging of broadband electromagnetic radiation. A piezoelectric layer 1406 is sandwiched between an electrode 1405 and a ground plane 1407. The electrode is coated with a wide-band EM absorbing layer 1403, such as a carbon coating or a black paint. This single element sensor head 1419 is connected to an amplifier 1409 and an optional low-pass or band-pass filter 1410 to remove unwanted noise. A scanning spot generating optical apparatus 1424 illuminates the object 1417 with a single spot 1425. The position of the spot 1425 can be shifted in x and y directions as indicated by arrows $A_x$ and $A_y$, respectively by mechanical or electrical control or a combination thereof of the components of the apparatus 1424. At each x- and y-position of the spot 1425 data is collected. The apparatus 1424 can be composed of diffractive, refractive or reflective optics, and any combination thereof. Spot generation from a source can be achieved using such optics. For example in a particular embodiment, a spot can be generated from a point source by using a spherical lens or a spherical mirror. A direct laser source can be used as a spot generator. Scanning of the position of the spot 1425 can be achieved in variety of methods, such as using scanning mirrors, by moving the optical components, by moving or tilting the source, or by using electrically controlled components, such as liquid crystal light valves.

In other embodiments digital electronics are used to store the scanned data and display the data once all the scans are complete.

Figure 15:
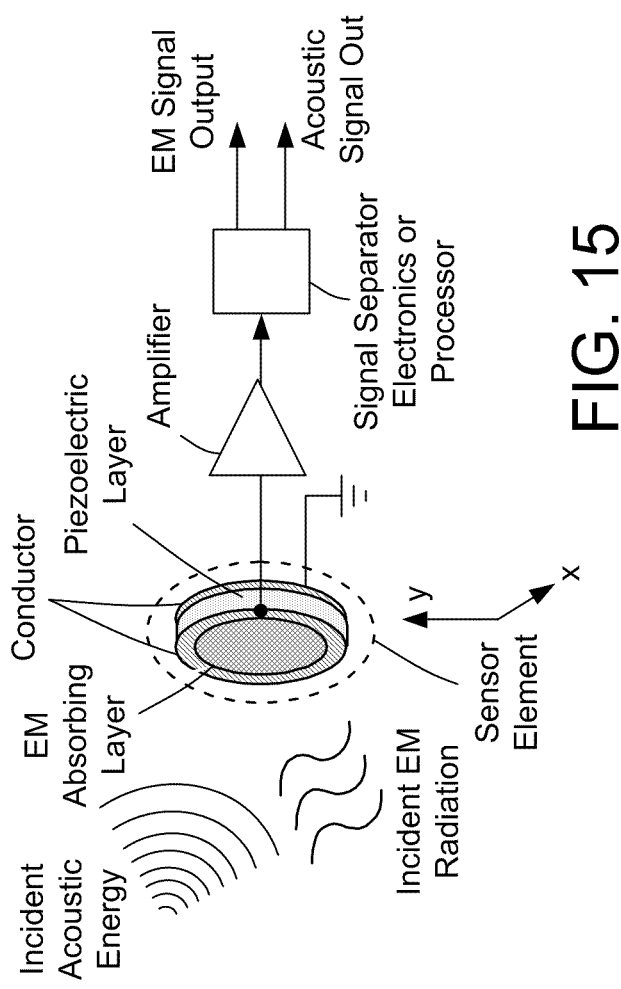
FIG. 15 is a perspective pictorial and block diagram depicting a combined electromagnetic (EM) and acoustic sensor.

FIG. 15 depicts a combined EM and acoustic sensor. A signal separator can be composed of either analog or digital circuit or processor or a combination of both. The separator separates the EM signature from the acoustic signature by band-pass, low-pass or high-pass filtering the data in a given range. If the EM source is modulated, then the processor is looks for signature within the modulation frequency to select the EM signal.

Figure 16A:
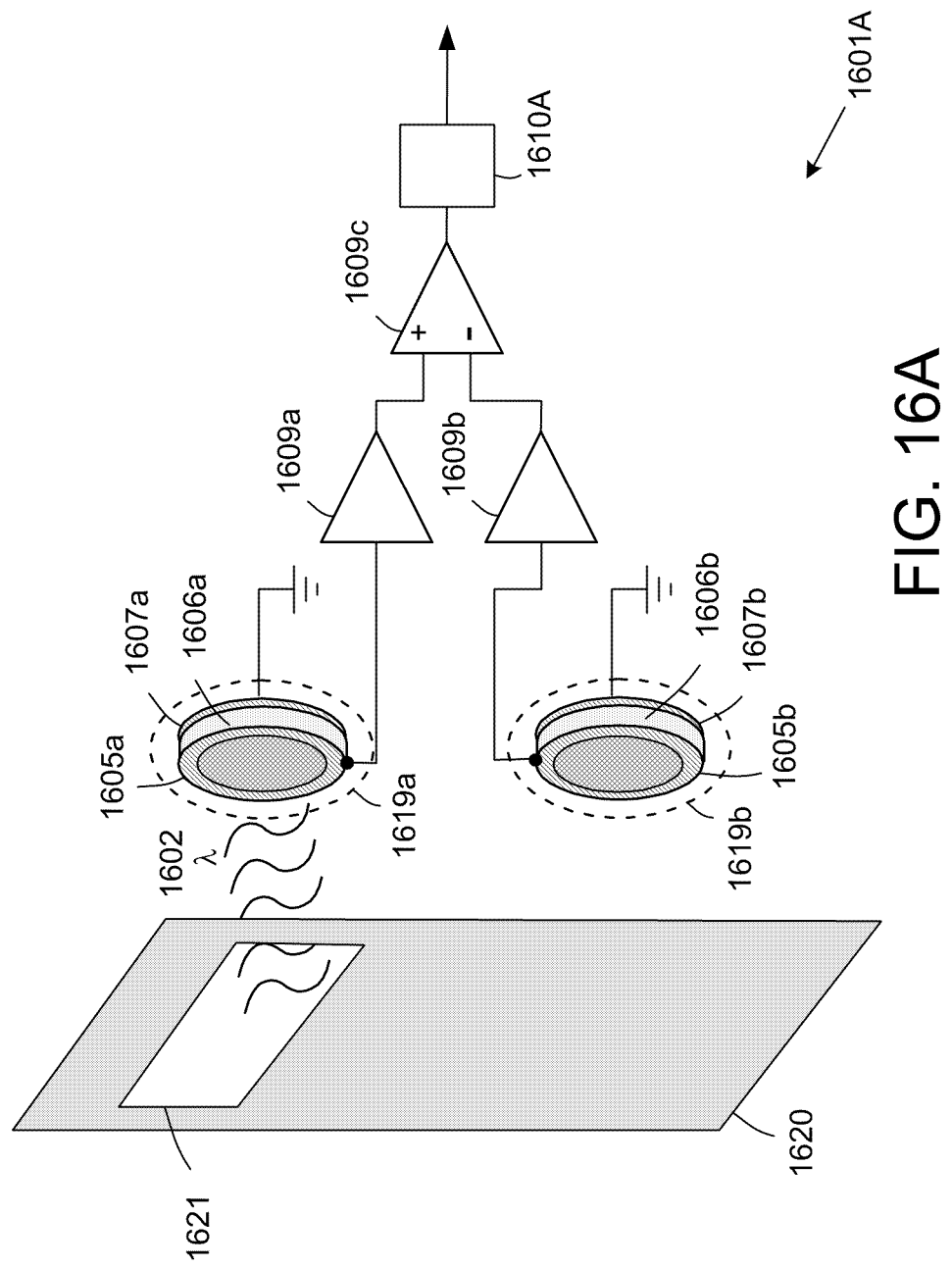
FIGS. 16A through 16D are perspective pictorial and block diagrams showing embodiments of sensors configured for single element, one-dimensional or two-dimensional photo-acoustic imaging of broadband electromagnetic radiation.

Referring to FIG. 16A, a perspective pictorial and block diagram illustrates an embodiment of a sensor configured for single element, one-dimensional or two-dimensional photo-acoustic imaging of broadband electromagnetic radiation. The sensor elements described throughout the disclosure can be used such that two identical sensors are placed at close proximity, or on the same substrate. EM radiation illuminates one of the elements 1619A-a, while the reference element 1619A-b is blocked from the incident radiation. Illumination of the sensor elements 1619A-a and 1619A-b is achieved by any known techniques such as using irises 1621A and radiation blocking material 1620A, or using imaging optics to focus only on one of the sensor heads 1619A-(a,b). The output of each sensor is amplified using amplifiers 1609A-a and 1609A-b, filtered if necessary using a low-pass, band-pass or high-pass filters, and fed into a differential amplifier 1609A-c. Because of their close proximity, each sensor head 1619A-a and 1619A-b experience the same (or similar) acoustic, mechanical, thermal or electrical noise, whereas only one sensor 1619A-a responds to the incident radiation 1602A. Subtracting the signal from each amplifier reduces or eliminates acoustic, mechanical, thermal or electrical noise or any other noise that is common to both sensor heads 1609A-a and 1609A-b. The function of the differential amplifier 1609A-c can be also achieved using digital electronics, where the signal either directly from the sensor heads 1609A-a and 1609A-b, or the amplified signals 1609A-a and 1609A-b are converted to a digital signal using analog-to-digital converter or a data acquisition system and the signal is subtracted either using digital electronics or using computer software if the digital data is fed into a computer.

The differential detection method to remove noise depicted in FIG. 16A can be used with any of the sensors and sensing techniques described throughout the disclosure, by using two identical or near identical sensors are used in close proximity or created on the same substrate.

In another embodiment similar to FIG. 16A, the apparatus may contain signal separator electronics as depicted in FIG. 15 to yield both optical and acoustic signals.

Figure 16B:
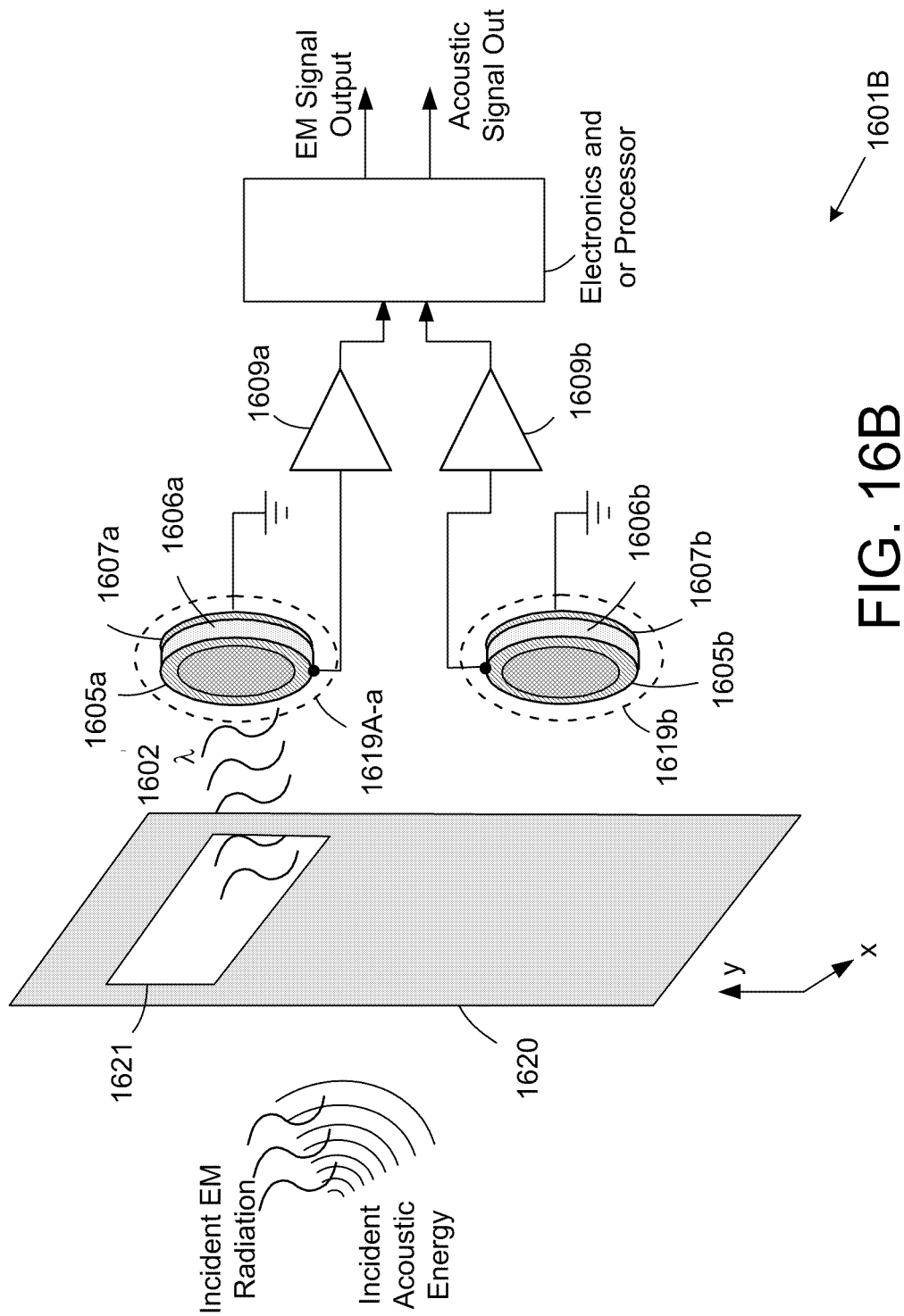

Referring to FIG. 16B, a perspective pictorial and block diagram illustrates an embodiment of a sensor configured for single element, one-dimensional or two-dimensional photo-acoustic imaging of broadband electromagnetic radiation. The sensor elements described throughout the disclosure can be used such that two identical sensors are placed at close proximity, or on the same substrate. The apparatus is similar to FIG. 16A, with two major differences. First, the differential amplifier and filter are combined all in the Electronics and Processor. This is done either in analog domain, or after the data is digitized and processing is done in the digital domain, or a combination of both are performed in a combined electronics and system, such a computer system with data acquisition system. The electronic processor filters the data, phase shifts if necessary to match the phase of the two signals from each sensor, and adds or subtracts the two signals, and further filters the final signal to yield a clean EM signal as well as the acoustic signal.

In another embodiment similar to FIG. 16B, the processing electronics may contain signal separator electronics as depicted in FIG. 15 to yield both optical and acoustic signals.

In another embodiment similar to FIG. 16B, a modulated acoustic source is intentionally present to the apparatus 1601B. Using a known source of a known modulation will help filter out the noise.

Yet in another embodiment similar to FIG. 16B, a modulated acoustic source is intentionally present to the apparatus 1601B, and in this the source modulates the sensor such that the sensor will react to static EM fields, thus allowing the sensor to detect static (DC) EM fields. An example of a static EM field is light source with a constant intensity level that does not vary in time.

This sensor arrangement 1601B depicted in FIG. 16B is used for at least three purposes: a) To filter out background acoustic noise to yield a clean, and b) to generate combination of acoustic and EM signals, and c) to enable the sensing apparatus to detect static EM fields.

Figure 16C:
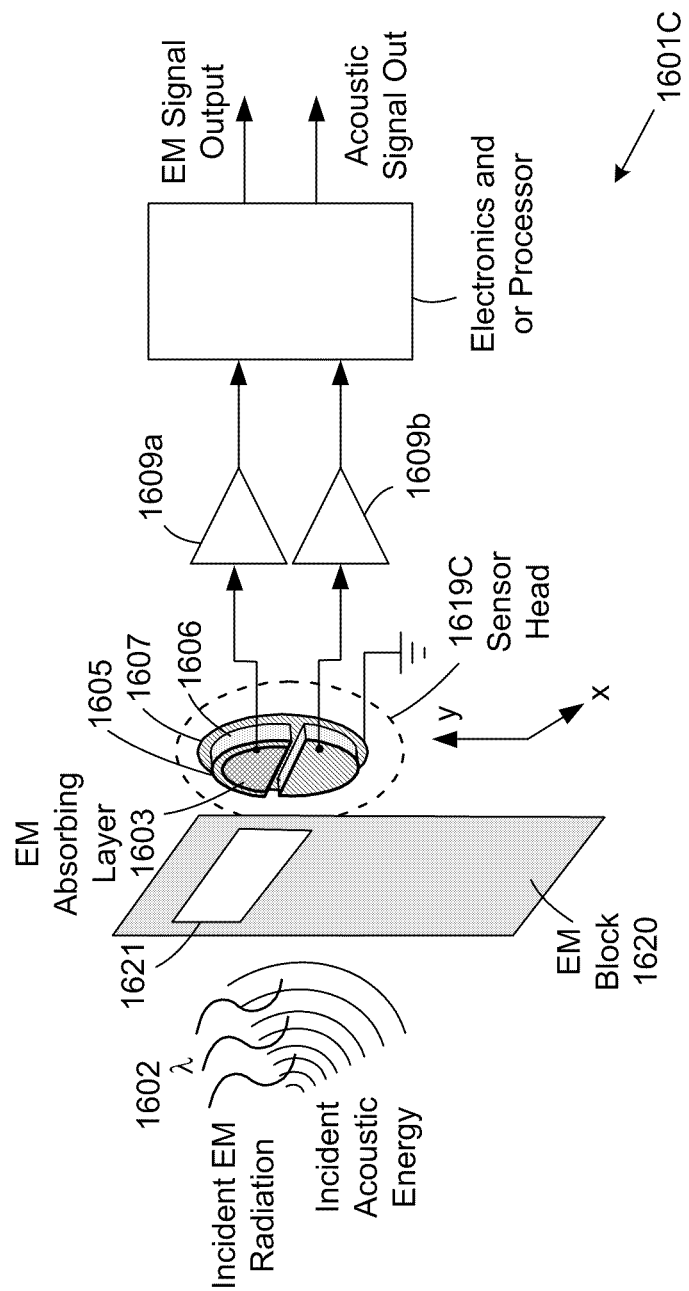

Referring to FIG. 16C, a perspective pictorial and block diagram illustrates an embodiment of a sensor 1601C configured for single element, one-dimensional or two-dimensional photo-acoustic imaging of broadband electromagnetic radiation. The sensor elements described throughout the disclosure can be used such that two identical sensors are placed at close proximity, or on the same substrate. The apparatus is similar to FIG. 16A and FIG. 16B, but the two sensor heads are replaced with a single sensor element 1619C. The functionality and the purpose of FIG. 16C apparatus are similar to FIG. 16A and FIG. 16B. The two sensing elements of the sensor head 1619C either utilize the same common conductor as shown in FIG. 16C, or each can have a separate conductor.

Figure 16D:
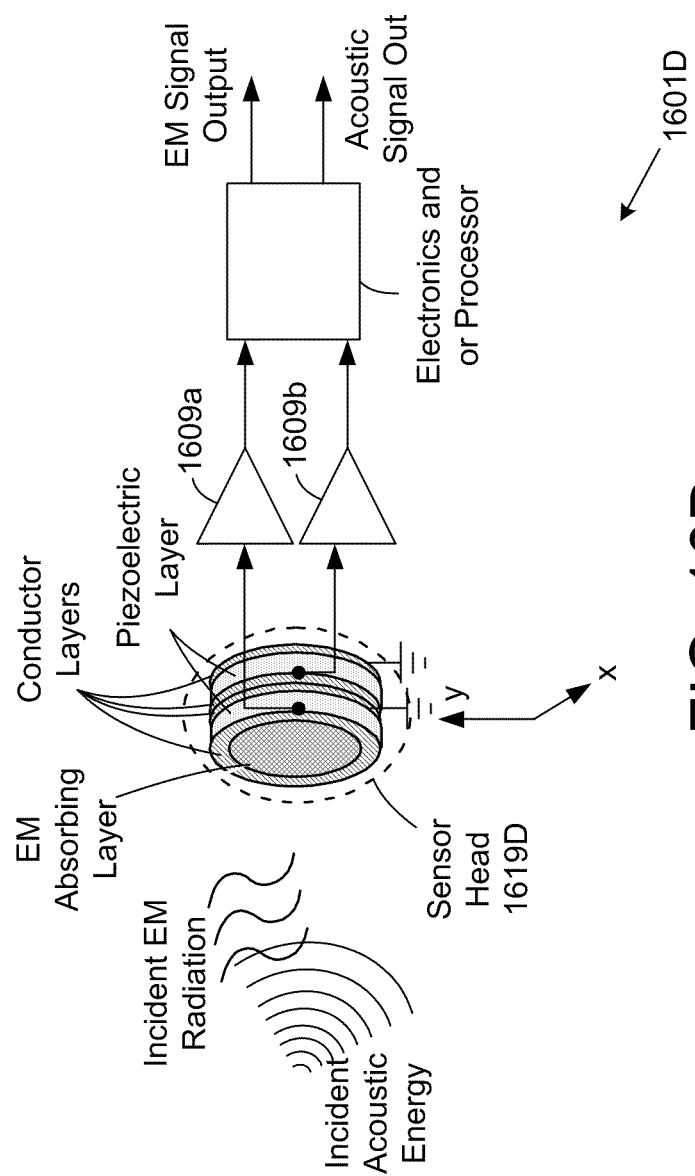

Referring to FIG. 16D, a perspective pictorial and block diagram illustrates an embodiment of a sensor 1601D configured for single element, one-dimensional or two-dimensional photo-acoustic imaging of broadband electromagnetic radiation. The sensor elements described throughout the disclosure can be used such that two identical sensors are placed at close proximity, or on the same substrate. The apparatus is similar to FIG. 16A and FIG. 16B, but the two sensor heads are replaced with a single sensor element 1619D. The functionality and the purpose of FIG. 16D apparatus are similar to FIG. 16A and FIG. 16B. The two sensing elements of the sensor head 1619D9 either utilize the same common conductor as shown in FIG. 16C, or each can have a separate conductor.

Figure 17:
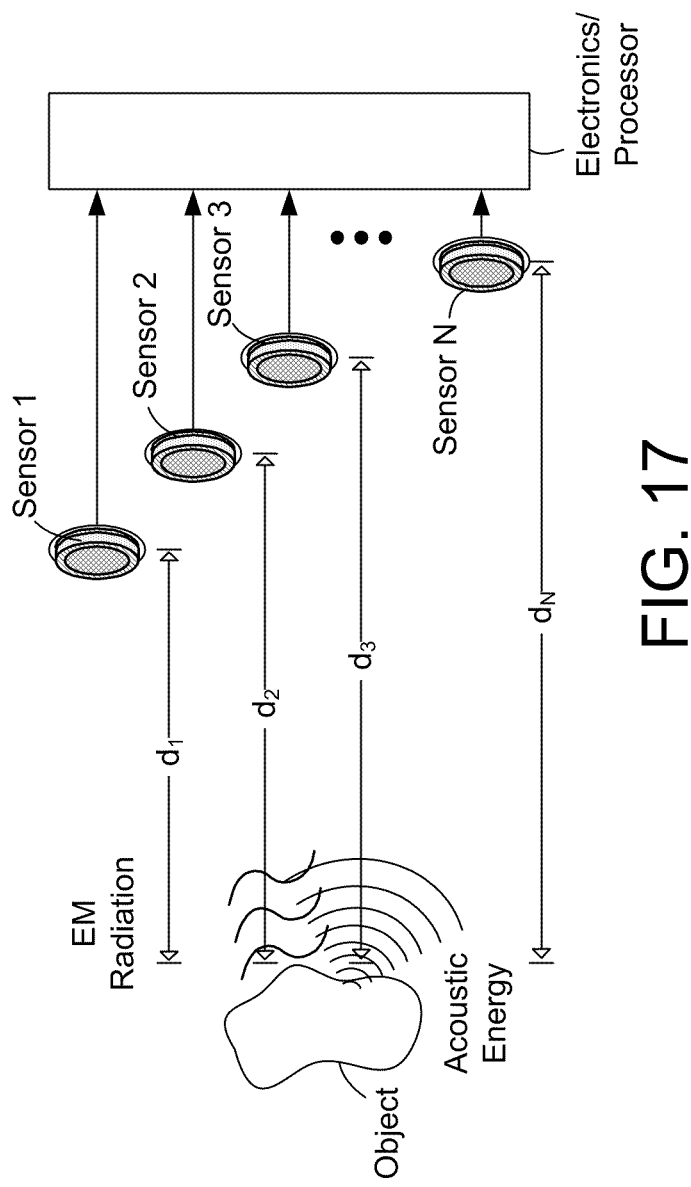
FIG. 17 is a pictorial and block diagram depicting a combined EM and acoustic sensor arrangement using multiple sensors arranged in different spatial distances from a source or object.

FIG. 17 depicts a combined EM and acoustic sensor arrangement using multiple sensors (Sensor 1 to Sensor N) arranged in different spatial distance ($d_1$ to $d_N$) from source or the object that reflects, transmits or scatters acoustic and/or EM radiation to distinguish between optical and acoustic signals. The acoustic signal travels much slower than the EM wave, therefore time delay between various acoustic signals allows distinction between acoustic signal and EM signal.

In another embodiment similar to FIG. 17, the sensors are arranged such that the acoustic signals arriving at different times to different sensors are used for triangulation of the target to determine the location of the source.

Figure 18A:
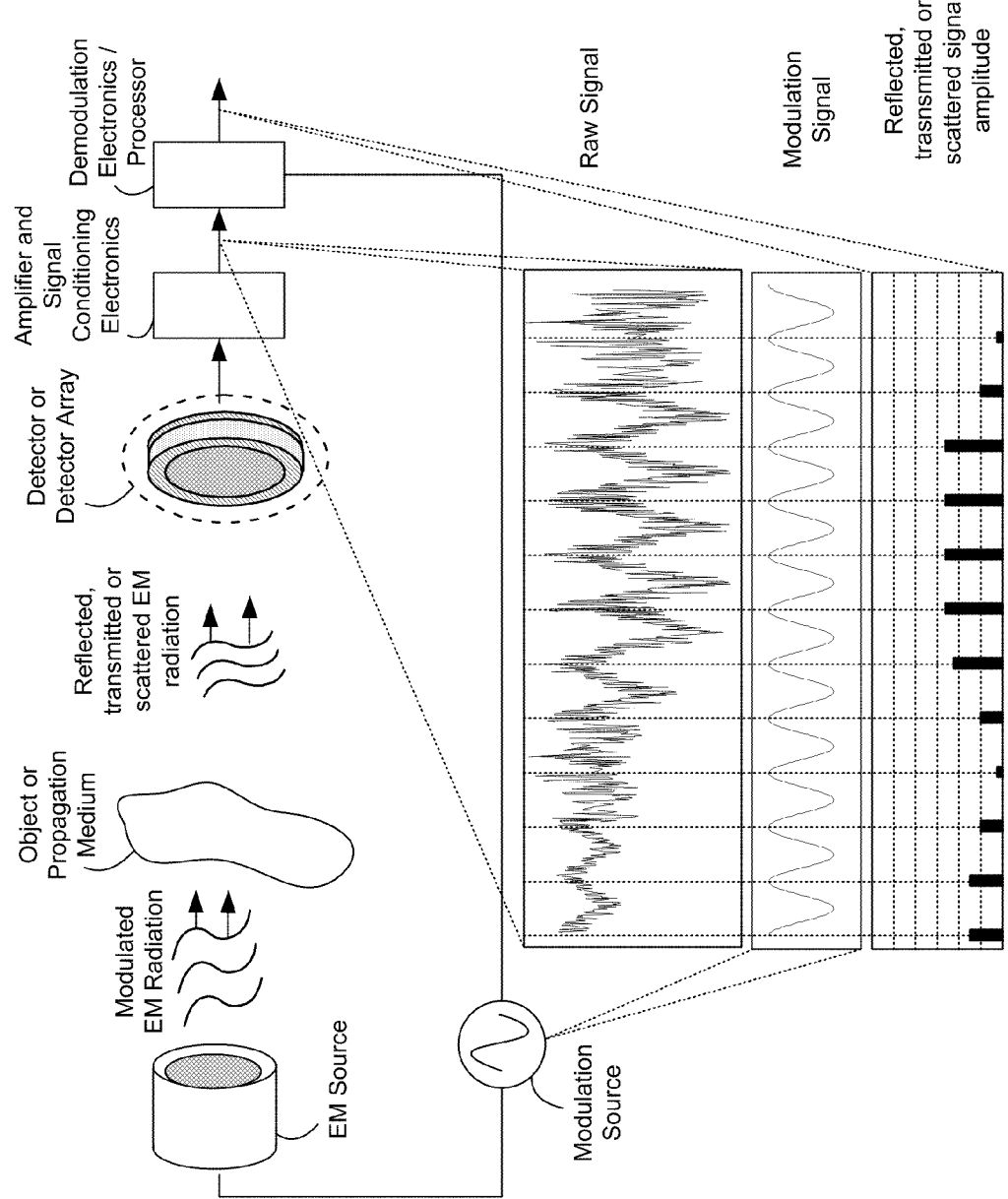
FIGS. 18A and 18B are a pictorial and block diagram of a sensing configuration and resulting signal waveforms showing electromagnetic (EM) source modulation using a wide spectral band sensor illustrating signal to noise ratio (SNR) reduction by modulating the EM source and by synchronous detection.

FIG. 18A depicts EM source modulation to a) achieve optimum performance by modulating the source, b) reduce noise level using by synchronized clocking of light modulation and detection signals, and c) avoid any detection error due to sensor drift. Signals are combined by the combined EM/acoustic sensor.

In another similar embodiment, instead of modulating the source, a mechanical modulation is employed, such as using a chopper wheel, modulating the light emitted from the source.

Figure 18B:
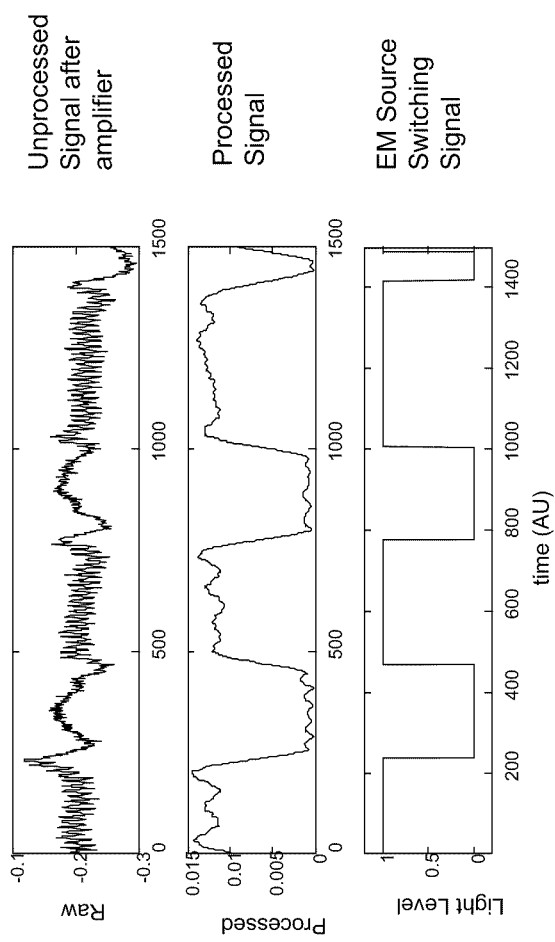

FIG. 18B illustrates an example using a wide spectral band sensor illustrating signal to noise ratio (SNR) reduction by modulating the EM source and by synchronous detection. Bottom curve is the light source switching signal. Top curve is the unprocessed signal. Middle curve includes synchronized and filtered signals.

Figure 19:
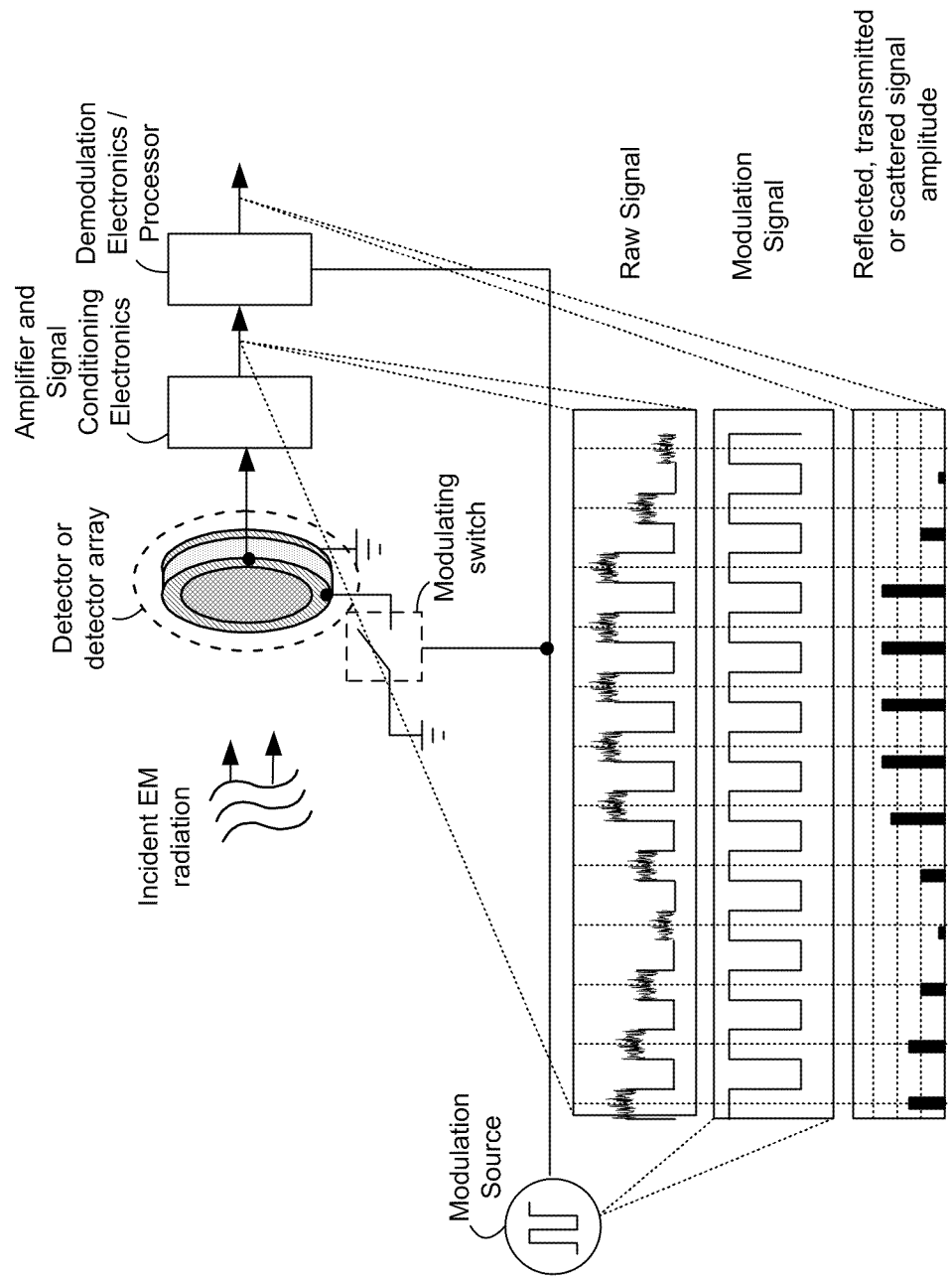
FIG. 19 is a pictorial and block diagram of a sensing configuration and a signal waveform diagram which depicts sensor switching by source modulation.

FIG. 19 depicts sensor switching by source modulation to a) achieve optimum performance by modulating the source, b) reduce noise level using by synchronized clocking of light modulation and detection signals, and c) getting rid of any detection error due to sensor drift. Signals are combined by the combined EM/acoustic sensor. Switching is achieved using a transistor circuit, by field-effect transistors and associated circuitry, by other means of electronic switching using either analog or digital electronic circuitry, opto-electronic switching, or by mechanical switching such as using relays.

In another embodiment similar to FIG. 19, instead of using an electrical switch, mechanic modulation is employed, such as using a chopper wheel in front of the detector.

Figure 20:
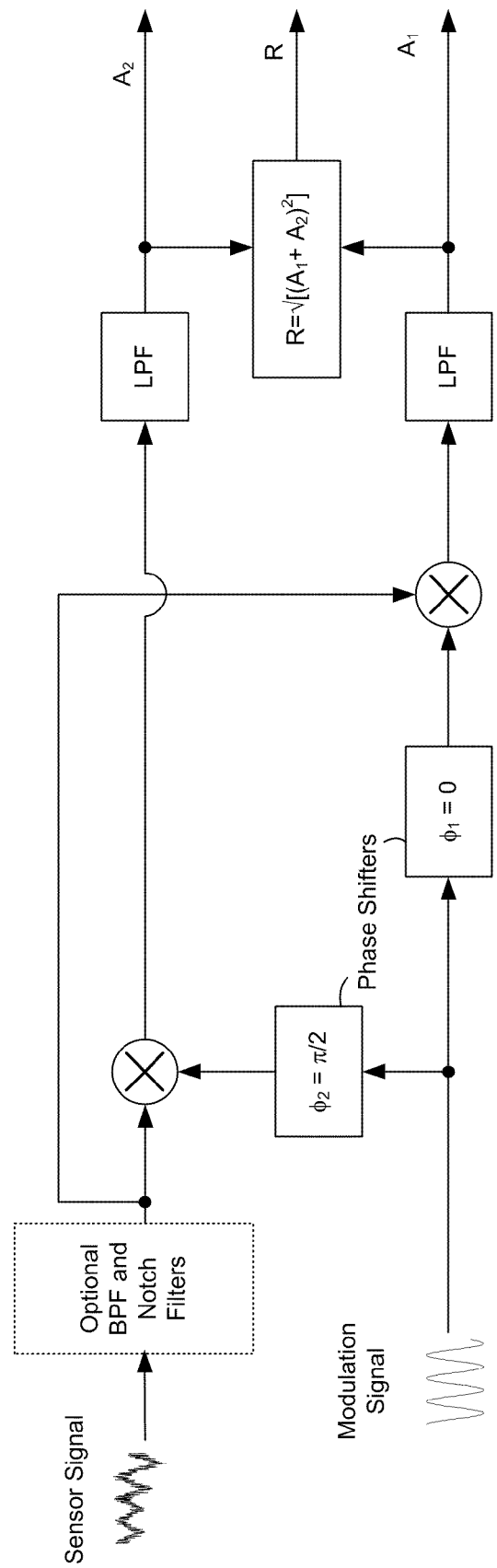
FIG. 20 is a schematic block diagram depicting a lock-in detection system used with a modulated source or modulated detection.

FIG. 20 depicts lock-in detection system used with a modulated source or modulated detection, such as depicted in FIGS. 18A, 18B, and 19, or using mechanical modulation such as using chopper wheels, or by using relays. LPF: Low-pass filter. $A_1$ and $A_2$ are the in-phase and out-of phase signals. The choice of $A_1$, $A_2$, or R for detection and analysis depends on the design of the sensing system. An optional band-pass filter (BPF) can be used to pre-clean the incoming signal. Additional filters can also be used to further reduce noise, such as using a 60 Hz notch filter to remove line noise.

Figure 21:
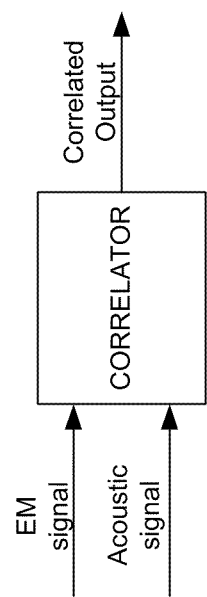
FIG. 21 is a schematic block diagram depicting a structure for correlating the EM and acoustic signals.

FIG. 21 depicts a method for correlating the EM and acoustic signals.

In a particular embodiment the correlated output of FIG. 21 can be used for automatic target recognition.

FIG. 22 depicts wavelength filtering using a) transmission filters, b) multi-layer interference filters using multi-layer alternating materials of different refractive index, and c) using etched periodic gratings of a particular period, such that they diffract certain wavelength bands. d) Filters attached on a sensor array, with each filtered element yielding a signal in a particular wavelength band. Sub-band selection is achieved using any of the filter arrangements shown in (a), (b) or (c), or any combination thereof.

In another embodiment similar to FIG. 22 wavelength tuning can be achieved using a single element sensor using one- or two-dimensional scanning using any other methods FIGS. 1 to 15, while the sensor is covered with various filters at different locations.

FIG. 23 depicts a method of generating two-dimensional image data using multi-layer device. A) Cross section of a single element and signal switch and detection details. B) Device with multiple pixels. C) Switching and detection signals with a multiple pixel device. Sx and Sy refer to x and y switches in (A) and the corresponding drive signals. Sensor system parameters, namely the piezoelectric layer poling direction, the amplifier polarity, the ground plane for each layer and any subsequent phase shifters used after each line are configured such that x and y switches are on, will get the highest signal.

Figure 24A:
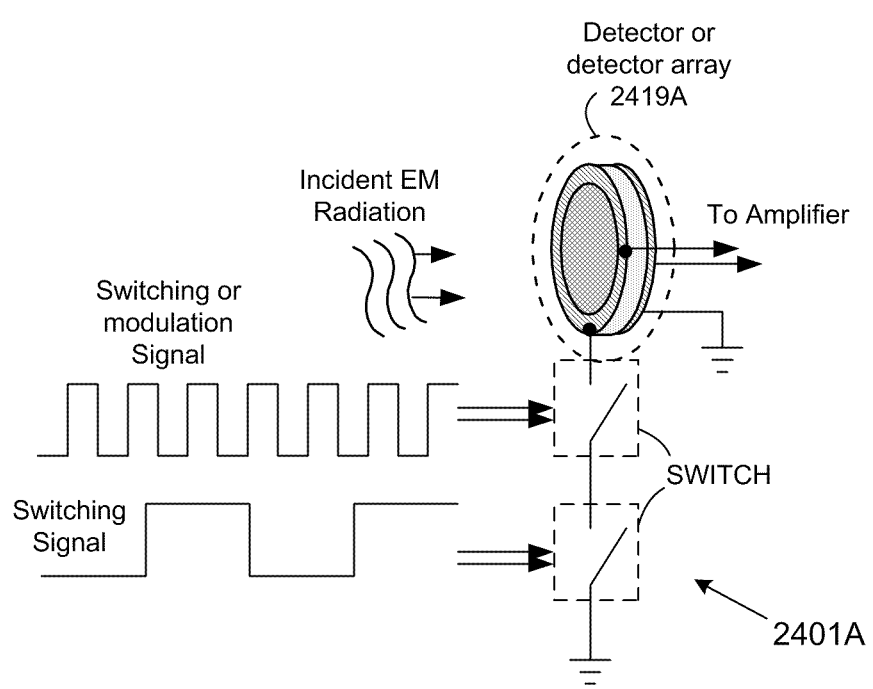
FIGS. 24A and 24B are pictorial and block diagrams of sensing configurations and associated signal waveforms showing double switching devices to be used with the broadband sensors.

FIG. 24A depicts a double switching apparatus to be used with the broadband sensors depicted throughout. One of the switches is used for modulating the signal to reduce the background noise and, and the other switch is used to either the scan the sensor for 1-dimensional and 2-dimensional images.

In other embodiments similar to FIG. 24A, the detector head 2419A can be replaced with any of the 1-dimensional or 2-dimensional sensor heads depicted throughout the disclosure.

In other embodiments, either or all the switching and modulating signals can be digital signals. In still other embodiments, either or all the switching and modulating signals can be analog signals. In further embodiments, either or all the switching and modulating signals can be digital signals, analog signals, a combination of digital and analog signals, or any arbitrary shaped signal.

Figure 24B:
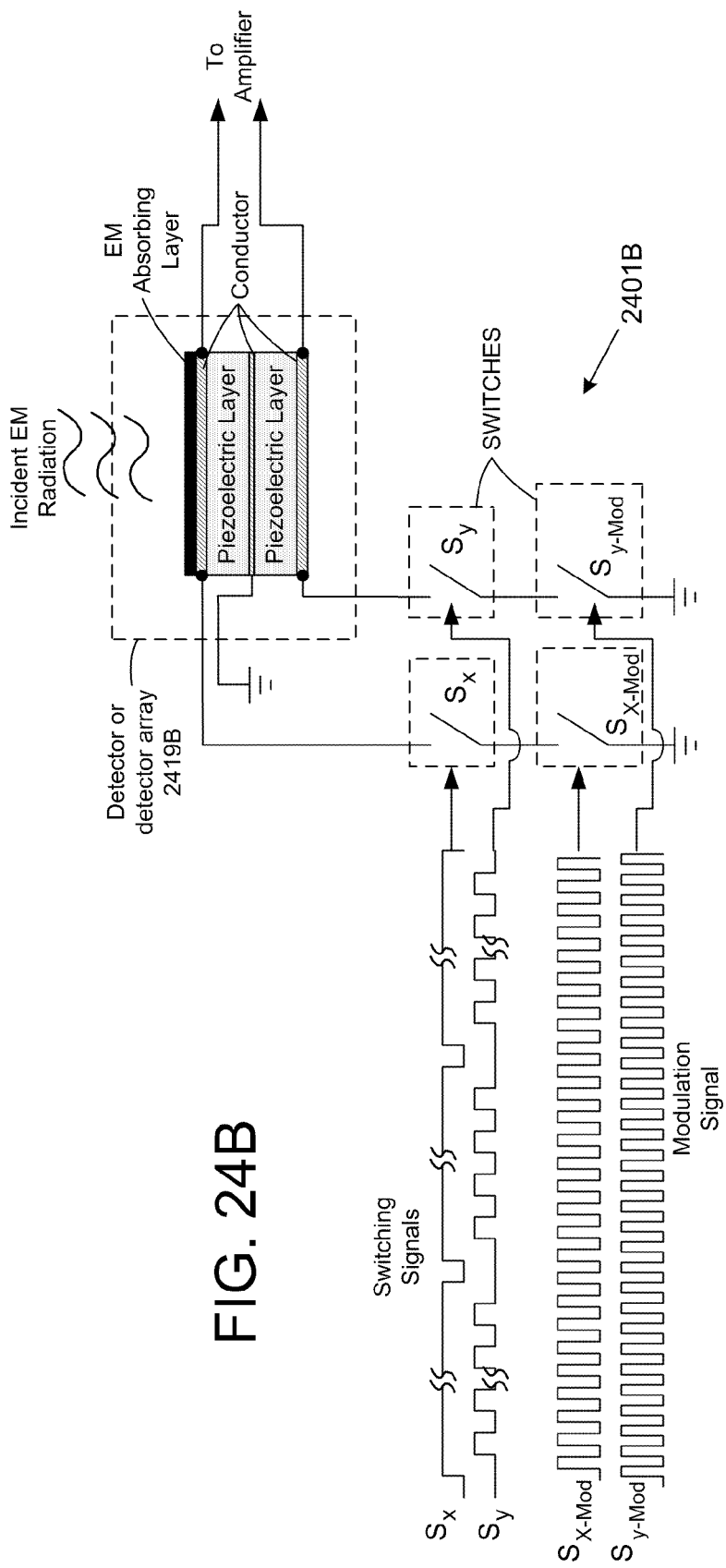

FIG. 24B depicts a double switching apparatus to be used with the broadband sensors depicted throughout. One of the switches is used for modulating the signal to reduce the background noise and, and the other switch (such as Sx or Sy) are used to scan the sensor for imaging as depicted in FIG. 23.

In other embodiments similar to FIG. 24B, the modulating signals $S_{x-mod}$ and $S_{y-mod}$ can have the same frequency.

In other embodiments similar to FIG. 24B, the modulating signals $S_{x-mod}$ and $S_{y-mod}$ can have different same frequencies.

In other embodiments, either one, -two, -three, or all the switching and modulating signals can be digital signals.

In other embodiments, either one, -two, -three, or all the switching and modulating signals can be analog signals.

In other embodiments, either one, -two, -three, or all the switching and modulating signals can be digital signals, analog signals, a combination of digital and analog signals, or any arbitrary shaped signal.

FIG. 25 depicts application of broadband sensor for communication. Various tunable filters and source wavelength tuning can be used to optimize transmission in the propagation medium.

In another embodiment similar to FIG. 25, the propagation medium is a fiber-optic cable, either a single mode or a multi-mode fiber.

Yet in a particular embodiment similar to FIG. 25, the propagation medium is free-space, such as the atmosphere, or various atmospheric conditions, or vacuum for space communication.

In other embodiments similar to FIGS. 15 to 25, and other embodiments depicted throughout the disclosure, either the source or the sensor or both include optics for shaping and collecting source and/or detector EM radiation.

Yet other embodiments similar to FIGS. 15 to 25, and other embodiments depicted throughout the disclosure, either the source or the sensor or both include lenses, mirrors, diffractive, refractive or scattering optics, or any combination thereof for shaping and collecting source and/or detector EM radiation.

Figure 26:
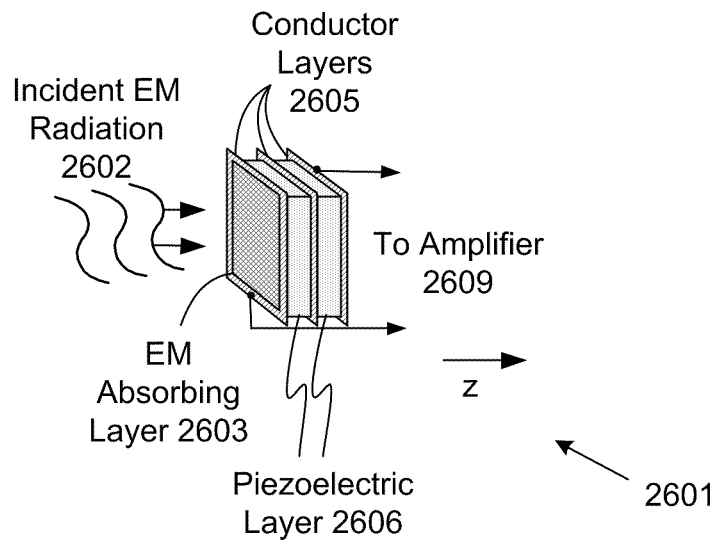
FIGS. 26, 27, 28, and 29 are perspective pictorial and block diagrams illustrating embodiments of sensors configured for detection or imaging of broadband electromagnetic radiation.

Referring to FIG. 26, a perspective pictorial and block diagram illustrates an embodiment of a sensor 2601 configured for detection or imaging of broadband electromagnetic radiation with increased sensitivity compare to a single layer. Two piezoelectric layers 2606 are sandwiched between conductive layers 2605. One of the outer conductive layers facing the EM radiation 2602 is coated with a wide-band EM absorbing layer 2603, such as a carbon coating or a black paint. Presence of the EM radiation produces a signal that is then sent to the amplifier 2609.

In another embodiment, the two piezoelectric layers 2606 have polarization orientation in opposite directions from each other. For example, each piezoelectric layer may have polarization normal to the electrode plane, however one oriented in +z direction, and the other –z direction.

Yet in another embodiment, the two piezoelectric layers 2606 have polarization orientations in the same direction.

Referring to FIG. 27, a perspective pictorial and block diagram illustrates an embodiment of a sensor 2701 configured for detection or imaging of broadband electromagnetic radiation. Two piezoelectric layers 2706 are sandwiched between conductive layers 2705. One side of the device is coated with a wide-band EM absorbing layer 2703, such as a carbon coating or a black paint. Presence of the EM radiation produces a signal that is then sent to the amplifier 2709.

In another embodiment, an intermediate layer, such as another material, e.g. a metal layer, may be added to the edge of the sensor, and coat a wide-band EM absorbing layer 2703 on top of this layer.

In another embodiment, the two piezoelectric layers 2706 have polarization orientation in opposite directions from each other. For example, each piezoelectric layer may have polarization normal to the electrode plane, however one oriented in +z direction, and the other −z direction.

Yet in another embodiment, the two piezoelectric layers 2706 have polarization orientations in the same direction.

Referring to FIG. 28, a perspective pictorial and block diagram illustrates an embodiment of a sensor 2801 configured for detection or imaging of broadband electromagnetic radiation with increased sensitivity compare to a single layer. Multiple piezoelectric layers 2806 are sandwiched between conductive layers 2805. One of the outer conductive facing the EM radiation 2802 is coated with a wide-band EM absorbing layer 2803, such as a carbon coating or a black paint. In the embodiment depicted in FIG. 28, the multiple piezoelectric layers 2806 have polarization direction at alternating orientation. The conductive layers are also connected to each other at alternating scheme. Presence of the EM radiation produces a signal that is then sent to the amplifier 2809.

In another embodiment similar to FIG. 28, the multiple piezoelectric layers 2806 have polarization direction in the same direction. In this case, only the first and the last layer conductors are connected to the amplifier.

Yet in another embodiment similar to FIG. 28, the EM absorbing material can be coated on the side of the device in the y-z plane instead of the x-y plane, and the incident radiation is incident on this absorbing layer.

Referring to FIG. 29, a perspective pictorial and block diagram illustrates an embodiment of a sensor 2901 configured for detection or imaging of broadband electromagnetic radiation. Two piezoelectric layers 2906 are sandwiched between conductive layers 2905. All or portion of one of the outer conductive layers facing the EM radiation 2902 is coated with a wide-band EM absorbing layer 2903, such as a carbon coating or a black paint. This embodiment is a bending structure. One side of the piezoelectric/conductor layer stack is attached to a base. Presence of the EM radiation produces a signal that is then sent to the amplifier 2909.

In another embodiment similar to FIG. 29, the two piezoelectric layers 2906 have polarization orientation in opposite directions from each other. For example, each piezoelectric layer may have polarization normal to the electrode plane, however one oriented in +z direction, and the other −z direction.

Yet in another embodiment similar to FIG. 29, the two piezoelectric layers 2906 have polarization orientations in the same direction.

Yet in another embodiment similar to FIG. 29, the double layer structure comprising two piezoelectric layers 2906 and four conductive layers 2905 can be replaced with a multi-layer structure similar to FIG. 28, with piezoelectric layers have polarization direction at alternating orientation, and electrodes connected in alternating fashion similar to FIG. 28.

Yet in another embodiment similar to FIG. 29, the double layer structure consisting of two piezoelectric layers 2906 and four conductive layers 2905 can be replaced with a multi-layer structure similar to FIG. 28, with piezoelectric layers have polarization at the same direction. In this case, only the first and the last layer conductors are connected to the amplifier.

Figure 30:
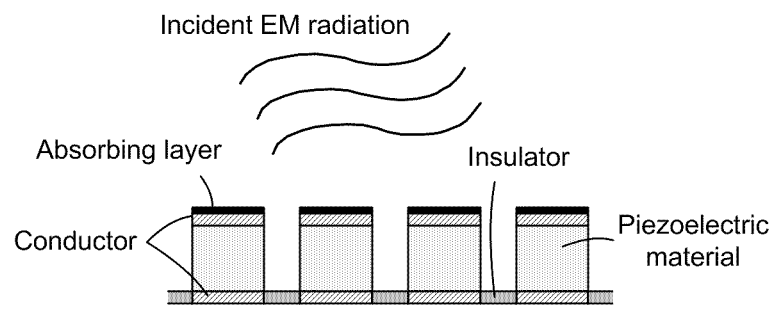
FIGS. 30 through 33 are cross-sectional cut-away pictorial views showing embodiments of structures for spatial sampling of a broadband EM image.
Figure 31:
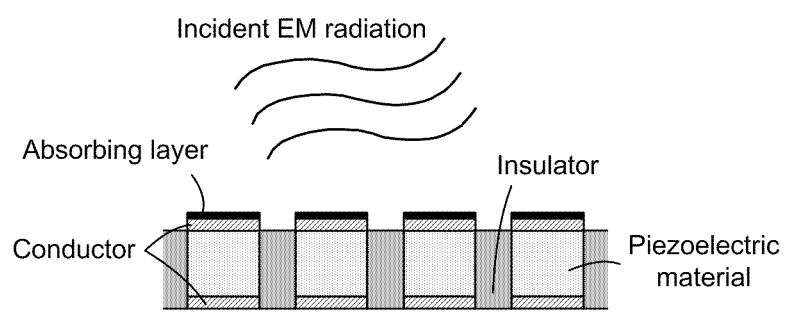
Figure 32:
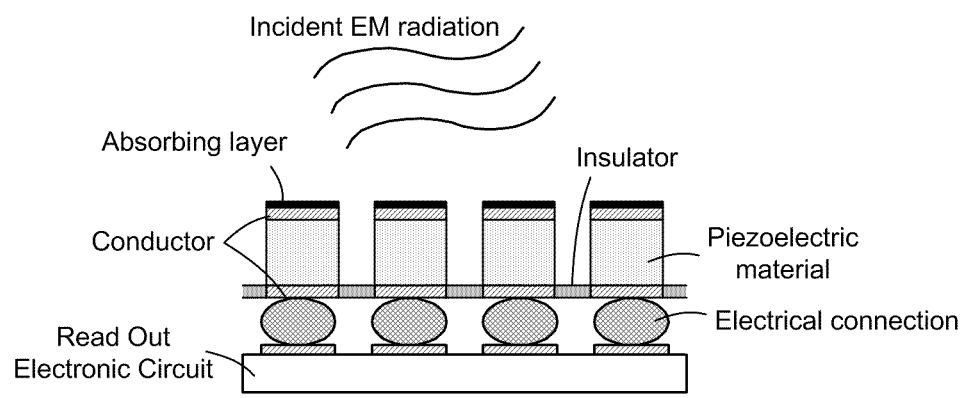

Referring to FIGS. 30 to 32, several cross-sectional cutaway pictorial views show embodiments of structures for spatial sampling of a broadband EM image. Spatial sampling can be achieved by various techniques including usage of a pixelated or multi-element sensor. The cross-sections of the different pixelation scheme embodiments are shown in FIGS. 30 and 31. The insulating layer can be an electrical insulator, an acoustic insulator, or a combination of both materials.

Thermal conductivity and acoustic coupling between pixels can result in reduced image resolution than could be achieved with the pixel size. To overcome this limitation and to increase resolution, an air gap is utilized between pixels as depicted in FIG. 30, or acoustical or thermal insulator is utilized between pixels as depicted in FIG. 31.

Figure 33:
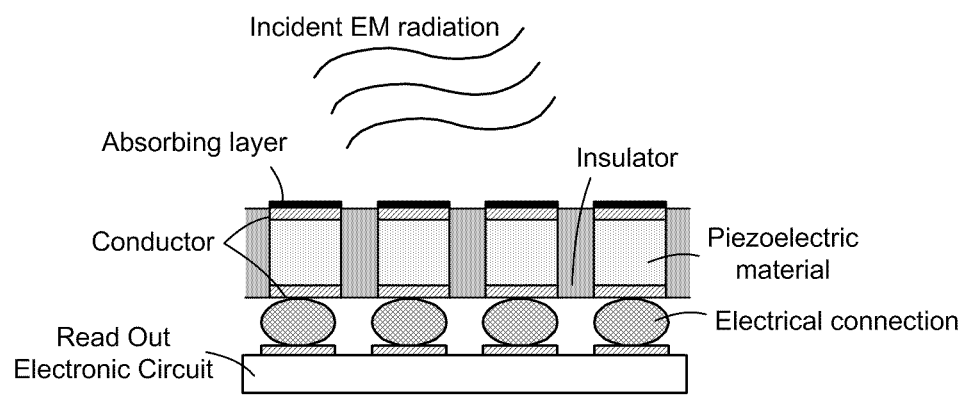

The devices shown in FIGS. 30 and 31 can be connected to an electronic circuit using any appropriate technique, such as using wire bonding, bump bonding as depicted in FIGS. 32 and 33 and any other technique.

A pixelation scheme for a photo-acoustic sensor is shown in FIGS. 30 and 31. The device consists of a piezoelectric layer, two conductive layers and an EM absorbing layer.

Various methods can be used to pattern devices in FIGS. 30 and 31. The patterning method of choice depends on the dimensions of the device. For example, if the pixels dimensions are in the micrometer range, than patterning using standard electronics is applicable, which involves creating pattern masks, lithographically patterning the device, and etching the materials chemically, or dry etching, and when appropriate, use various planarization techniques, such as chemical-mechanical polishing.

In other embodiments similar to FIG. 23 and other embodiments described herein, an imaging device can utilize the thermal and acoustical insulation techniques depicted in FIG. 30 or 31, where an air gap or an insulating material is used between each pixel.

Various other embodiments can be implemented. For example, in other embodiments similar to FIGS. 1 to 13 the EM source that illuminates the objects can be composed of multiple sources and is turned on and off sequentially such that the spectrum is scanned between these regions. Therefore the detector detects EM radiated at various source spectra, and thus yielding images at various spectra of the object. An example of such embodiment is to use a combination of UV, visible, IR and thermal sources, or Terahertz source. The sources can be any source available, including coherent and incoherent sources, light emitting diodes, lasers, thermal sources, incandescent sources, X-ray tubes, and any EM source available.

In other embodiments similar to FIGS. 1 to 13, the absorptive layer 503 can also be placed either on the electrode side or the back side, coated on the ground plane 507.

In other embodiments similar to FIGS. 5B, 6B, 7B, 8B, 9C, 9D, 10C and 10D, the EM source can be configured using external optics to illuminate portion of the object. The EM source and illumination optics can be placed between the source and the object determines the illumination size and shape and location and spatial distribution. In a particular embodiment, if a spherical lens is used after a point source or a circular source, a circular spot can be formed illuminates the object. In a particular embodiment, if a cylindrical lens is used after a point source or a circular source, a line spot can be formed to illuminates the object.

The amplifiers, filters and other associated electronics are often connected to ground, such as the ground plane of the device shown in various embodiments. In certain occasions ground plane is a floating ground plane, such as when using specific differential amplifiers.

In the embodiments depicted in these figures where illumination source is used, the EM source and illumination and detection optics can be configured such that either transmission or reflection, or scattering images can be obtained. For example, in a particular embodiment, if the object is placed between the source and the sensor, transmission image is obtained.

In FIGS. 1 to 13 the absorbing layer is shown on the top side, where the electrode is located. In other embodiments the absorbing layer facing the EM radiation is coated in the back side, over the ground plane.

In other embodiments similar to FIGS. 1 to 13, the piezoelectric material can be replaced with capacitive material such as a dielectric, air or vacuum. The electrical signal is therefore generated by capacitive effect.

In other embodiments similar to FIGS. 1B, and 2 through 13, the sensor can be implemented using a capacitive approach; where instead of piezoelectric material can be replaced with an insulator. Suitable insulators may be a vacuum, air, or other insulators.

When electromagnetic radiation is incident on the absorbing layer, the absorbed electromagnetic energy is converted to a mechanical energy via the photo-acoustic effect, and therefore changes the material dimensions, which then interferes with the traveling elastic wave.

Because the detection method uses photo-acoustic effect, the technique can therefore be used to image broadband electromagnetic radiation. In specific embodiments, the broadband spectrum may include, visible, infrared (IR), ultraviolet (UV) band, X-ray, microwave, millimeter waves, Terahertz frequency waves radiation from other parts of the electromagnetic spectrum.

In other embodiments similar to FIGS. 1 to 13, the electromagnetic radiation may be emitted by the objects itself.

In other embodiments similar to FIGS. 1 to 13, the electromagnetic radiation may be a narrowband or a wide band. Control of the spectral band is achieved using transmission filters, reflection filters or diffractive filters combined with the EM source, or placed in front of the sensor. Narrowband radiation is achieved using narrow spectral band sources.

In other embodiments similar to FIGS. 1 to 13 spectral scanning is achieved by using variable filters either in front of the source or in front of the sensor to scan the spectral band of interest. Example of variable filters are diffractive filters that can be rotated to diffract a particular wavelength or variable transmission filters such as thin film coated filters or color glass filters of different spatial distribution which are scanned spatially to transmit a particular wavelength range.

In other embodiments similar to FIGS. 1 to 13 spectral scanning is achieved by using either multiple sensors with filters in front of it, namely spatial separation of each wavelength band detecting elements. Proper optics, such as lenses, mirrors, beam splitters, or guided wave optics such as fiberoptics are often used to split the EM radiation from the object and distribute the split radiation to the multiple sensors.

In other embodiments similar to FIGS. 1 to 13 spectral scanning is achieved by using either a single sensors with filters in front of it, but modulating multiple sources sequentially and to detect signal or image from the sensor at particular time that corresponds to image at a particular wavelength or wavelength band. For example, if UV, blue, green, red, infrared and thermal images are to be obtained, then UV, blue, green, red, infrared and thermal are modulated sequentially and signals or images are detected at each modulation instant. The data set then represents spectral signal or image set.

In other embodiments the EM sources can be broad band, narrowband sources, incoherent sources, and coherent or partially coherent sources.

In other embodiments the EM sources can be light emitting diodes, laser diodes, lasers, gas lasers, die lasers, semiconductor lasers, lamps, incandescent sources and lamps, fluorescent sources and lamps, thermal sources, radiation sources such as radioactive elements, natural or man-made EM sources.

In other embodiments similar to FIGS. 1 to 13 one or more of the excitation and detection electrodes are either single element electrodes or inter-digitated electrodes or comb electrodes with either fixed pitch or variable pitch. Inter-digitated electrode width and pitch should be designed such to match the excitation signal frequency or frequency range to achieve optimum signal excitation and detection efficiency.

In other embodiments the band-pass filters are replaced with a frequency detecting electronic circuit and the signal yields change in modulation frequency due to presence of incident radiation, and yields the spatial and amplitude distribution of the incident EM radiation.

In other embodiments the band-pass filters are replaced with a phase detecting electronic circuit and the signal yields change in phase of the modulation signal due to presence of incident radiation, and yields the spatial and amplitude distribution of the incident EM radiation.

Yet in another embodiment the electrodes the overlaying absorptive coating, the piezoelectric layer and the ground plane can be of any arbitrary shape that will span any range of frequencies to yield spatial distribution of the incident radiation. Specific shape parameters are application-specific, and are chosen considering image size, resolution.

In another embodiment imaging achieved using pixels. To achieve pixel scan, each sensor pixel is attached to a transistor, such as a field effect transistor or JFET. By turning on each transistor using a clock signal, data from each pixel is collected. This method allows scanning each pixel without the need of having massively parallel number of wires, using only smaller channels.

In other embodiments similar to FIGS. 1 to 13 one- or two-dimensional imaging of the EM radiation is achieved by frequency modulation of either the source, or signal applied to the excitation electrodes, or to both.

In other embodiments similar to FIGS. 1 to 13, to detect low-level signals, a lock-in amplification method is utilized. Signal lock-in is achieved by locking-in the electrode modulation and detected signals, or by locking-in the EM source modulation and detected signals. If a combination of electrode modulations and source modulation are used, the detected signal is locked-in with one or both of the modulation signals.

In other embodiments similar to FIGS. 1 to 13, single piezoelectric layer architectures can be replaced by two or more layers as depicted in FIG. 9A.

In other embodiments similar to FIGS. 1 to 13, single piezoelectric layer architectures can be replaced by two or more layers and a differential amplifier as depicted in FIG. 9A.

In other embodiments depicted herein, two-dimensional imaging can be achieved using one-dimensional sensor by using multiple-parallel one-dimensional sensor elements, similar to the architecture depicted in FIG. 6A.

In other embodiments depicted herein, one-dimensional imaging can be achieved using single element sensor by using multiple-parallel single sensor elements, similar to the architecture depicted in FIG. 6A.

In other embodiments similar to FIGS. 1 to 12, the architecture of FIG. 13 using identical or similar sensors placed at close proximity or on the same substrate can be implemented to reduce noise.

In other embodiments similar to FIGS. 9B to 9D, 10B, 10C, 10D, and 13 and all other corresponding figures herein, the differential amplifier can be replaced with a dual amplifier. The dual amplifier inputs can be configured such that the inputs are reversed in polarity, have the same polarity, or have any arbitrary phase shift or bias shift. The bias and polarity of each amplifier input can be controlled using the appropriate amplifier inputs, feedback and biasing components, such as resistors and biasing voltages.

In other embodiments similar to FIGS. 9B to 9D, 10B, 10C, 10D, and 13 the functions of the differential can be performed using digital electronics. Either signal directly from the sensor electrodes, or from a single amplifier is fed to digital electronics via analog-to-digital converter, and all the functions of biasing signals, changing polarities, reversing polarities, filtering and other functions are performed in the digital domain.

In other embodiments similar to FIGS. 1 to 13 the functions of the amplifiers and filters can be performed using digital electronics. Either signal directly from the sensor electrodes, or from a single amplifier is fed to digital electronics via analog-to-digital converter, and all the functions of biasing signals, changing polarities, reversing polarities, filtering and other functions are performed in the digital domain.

In other embodiments similar to FIGS. 9B to 9D, and all other corresponding figures herein, the multi-layer architecture can have piezoelectric material either poled in the same direction or in the opposite direction.

In other embodiments similar to FIGS. 1 to 13 the image display can be achieved by storing the x, y or x and y scan data in digital form and display it after the data collection is complete. The analog data is first converted to digital data using analog-to-digital conversion circuit, sometimes also referred to data acquisition.

In other embodiments similar to FIGS. 11, 12 and 14, the sensor can be moved to achieve y-scan with respect to the imaging optics and the object.

In other embodiments similar to FIGS. 11, 12 and 14, both the sensor and the imaging optics can be moved together with respect to the object to achieve y-scan.

In other embodiments similar to FIGS. 18A, 19, 20, 21 and other embodiments depicted throughout the disclosure, source modulation and detection modulation are combined to further reduce detection noise and increase detection sensitivity.

In other embodiments similar to FIG. 19 and other embodiments depicted throughout the disclosure, modulated detection scheme enables detection of static (non modulated signals) because it converts the detector from AC response to DC, because the sensor is reset periodically by the switch, which grounds the sensor, and the signal jumps to a higher level when the switch is open.

In various embodiments where switch is demonstrated, the switch can be mechanical switch, electrical switch, electronic switch, opto-electronic switch, hardware switch, software based switch, or any other switch or a combination of various switching mechanism mentioned that can make the electrical connection depicted in the corresponding figures.

In various embodiments depicted throughout the disclosure, the shape of the sensor can be circular, elliptical, square, rectangular, or any arbitrary shape.

In various embodiments depicted throughout the disclosure, the sensors can be used to for acoustic detection, for EM detection, or a combination thereof.

In other embodiments similar to FIGS. 11A, 11B, 12A, 12B, 14A, 14B, 14C, and other embodiments depicted throughout the disclosure, instead of the object being scanned, the sensor head is scanned to yield 1-dimensional or 2-dimensional image.

In other embodiments similar to FIGS. 11A, 11B, 12A, 12B, 14A, 14B, 14C, and other embodiments depicted throughout the disclosure, either the sensor head, or the object, or both are scanned with respect to each other such to yield 1-dimensional or 2-dimensional image.

In other embodiments similar to embodiments depicted throughout the disclosure, switching and modulation signals are digital signals (on-off) or sinusoidal varying signals, or any arbitrary waveforms.

In other embodiments similar to embodiments illustrated throughout the disclosure depicting 1-dimensional or 2-dimensional imaging, either the x-scanning signal, the y-scanning signal or both can be either digital signals (on-off) or sinusoidal varying signals, or any arbitrary waveforms.

In other embodiments similar to all the figures that contain an EM absorbing layer, the absorbing layer can be any material that can absorb the portion of the EM radiation. The choice of material is dependent on which band of the EM radiation is desired to detect. For example, if only a narrow-band of the radiation is to be detected, the material of choice will absorb the desired band.

Yet in another embodiment similar to all the figures that contain an EM absorbing layer, a wide-band EM absorbing material can be used, and a narrow-band spectral filter can be added between the absorbing layer and the incident EM radiation to allow detection of narrow-band EM radiation.

Yet in another embodiment similar to all the figures that contain an EM absorbing layer, various portions of the sensor can be coated with different band EM absorbing layers to allow multi-band EM signal detection, analogous to a color detector or color camera.

Yet in another embodiment similar to all the figures that contain an EM absorbing layer, a wide-band EM absorbing material can be used and different narrow-band spectral filter can be added between the absorbing layer and the incident EM radiation, and the filters are spatially distributed such that each pixel yields a different band signal, thus yielding a multi-band EM signal or image, analogous to a color detector or color camera.

In other embodiments depicted throughout the disclosure, the apparatus can be used in various combinations to yield 1-dimensional, 2-dimensional or 3-dimensional image data.

In other embodiments depicted throughout the disclosure, the apparatus can be used in various combinations to result in increased sensitivity detection.

In other embodiments depicted throughout the disclosure, the apparatus can be used in various combinations to result in reduction in signal to noise ratio.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, functionality, values, process variations, sizes, operating speeds, and the like. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims.

What is claimed is:

1. An apparatus comprising:
    a broad spectral band sensor that detects electromagnetic and acoustic signals comprising:
        a photoacoustic detector comprising:
            a photoacoustically sensitive substrate;
            at least one excitation electrode coupled to the photoacoustically sensitive substrate; and
            at least one detection electrode coupled to the photoacoustically sensitive substrate; and
        an elastic wave modulator coupled to the photoacoustic detector.

2. The apparatus according to claim 1 further comprising:
    the broad spectral band sensor configured for traveling elastic wave detection wherein a modulation signal or pulse is applied to the at least one excitation electrode, generating elastic waves due to piezoelectric effect which travel along the photoacoustically sensitive substrate to the at least one detection electrode.

3. The apparatus according to claim 1 further comprising:
    the broad spectral band sensor configured for detecting and imaging incident electromagnetic radiation wherein a modulation signal is applied to the at least one excitation electrode, indicating changed dimensions of the photoacoustically sensitive substrate due to thermal expansion.

4. The apparatus according to claim 1 further comprising:
    the broad spectral band sensor configured for detecting and imaging incident electromagnetic radiation wherein size and shape of the at least one excitation electrode, the at least one detection electrode, and the photoacoustically sensitive substrate are selected to have spatially variable resonance frequency and frequency modulation enables detection of spatial distribution of electromagnetic radiation.

5. The apparatus according to claim 4 wherein:
    frequency modulation is selected among a group consisting of:
        a modulated signal applied to the at least one excitation electrode;
        a modulated signal applied to an electromagnetic (EM) radiation source; and
        a modulated signal applied to the at least one excitation electrode and a modulated signal applied to the electromagnetic (EM) radiation source.

6. The apparatus according to claim 1 further comprising:
    the broad spectral band sensor configured for two-dimensional broad spectral band imaging comprising:
        a one-dimensional sensor;
        imaging optics optically coupled to the one-dimensional sensor; and
        a scanner coupled to the one-dimensional sensor and/or the imaging optics that scans at least one of an object for imaging, the one-dimensional sensor, and the imaging optics to form a two-dimensional image.

7. The apparatus according to claim 1 further comprising:
    the broad spectral band sensor configured for two-dimensional broad spectral band imaging comprising:
        a single-element sensor;
        imaging optics optically coupled to the single-element sensor; and
        a scanner coupled to the single-element sensor and/or the imaging optics that scans at least one of an object for imaging, the single-element sensor, and the imaging optics to form a two-dimensional image.

8. The apparatus according to claim 1 further comprising:
    the broad spectral band sensor comprising an arbitrary shape that spans a plurality of frequencies to yield a spatial distribution of incident electromagnetic (EM) radiation.

9. The apparatus according to claim 1 further comprising:
    a scanner coupled to the broad spectral band sensor that scans at least one of an object for imaging and the broad spectral band sensor for imaging.

10. The apparatus according to claim 1 further comprising:
    a processor coupled to the broad spectral band sensor that executes software for processing signals from the broad spectral band sensor wherein signal processing comprises filtering and noise reduction.

11. The apparatus according to claim 1 further comprising:
    the broad spectral band sensor comprising a plurality of pixel structures comprising acoustic and thermal insulation materials.

12. The apparatus according to claim 1 further comprising:
    a multiple layer broad spectral band sensor comprising a plurality of piezoelectric layers alternating with a plurality of conductive layers wherein sensitivity is increased and noise reduced.

13. The apparatus according to claim 1 further comprising:
    a multiple element broad spectral band sensor wherein sensitivity is increased and noise reduced.

14. The apparatus according to claim 1 further comprising:
    the broad spectral band sensor comprising a plurality of sensor elements positioned in close proximity or on a single substrate wherein differences in signals among the plurality of sensor elements are detected for increased sensitivity and noise reduction.

15. The apparatus according to claim 1 further comprising:
    a communication channel comprising:
        signal generation electronics;
        a source wavelength controller;
        an electromagnetic source coupled to the signal generation electronics and the source wavelength controller;
        the broad spectral band sensor communicatively coupled to the electromagnetic source along the communication channel;
        beam shaping and detector optics between the electromagnetic source and the broad spectral band sensor; and
    detection and signal demodulation electronics coupled to the broad spectral band sensor.

16. The apparatus according to claim 1 further comprising:
the photoacoustic detector and the elastic wave modulator formed in a combined arrangement using a plurality of sensor elements arranged in a plurality of spatial distances from a reflecting source or object that reflects, transmits, or scatters acoustic and/or electromagnetic radiation, the combined arrangement distinguishing between optical and acoustic signals.

17. An apparatus comprising:
a broad spectral band sensor that detects electromagnetic and acoustic signals comprising:
   a photoacoustic detector; and
   an elastic wave modulator coupled to the photoacoustic detector that modulates the broad spectral band sensor.

18. The apparatus according to claim 17 wherein:
the elastic wave modulator modulates the broad spectral band sensor for noise reduction.

19. The apparatus according to claim 17 wherein:
the elastic wave modulator modulates the broad spectral band sensor for converting an alternating current (AC) sensor to a direct current (DC) sensor.

20. The apparatus according to claim 17 wherein:
the elastic wave modulator modulates the broad spectral band sensor for dividing the broad spectral band sensor into multiple pixels.

21. The apparatus according to claim 17 wherein:
the elastic wave modulator modulates the broad spectral band sensor for scanning.

22. An apparatus comprising:
a broad spectral band sensor that detects electromagnetic and acoustic signals comprising:
   a photoacoustic detector;
   an elastic wave modulator coupled to the photoacoustic detector; and
   at least one wavelength filter coupled to the photoacoustic detector.

23. The apparatus according to claim 22 wherein:
the at least one wavelength filter comprises transmission filters.

24. The apparatus according to claim 22 wherein:
the at least one wavelength filter performs wavelength band selection.

25. The apparatus according to claim 22 further comprising:
the at least one wavelength filter that selects wavelength band selected from a group consisting of:
   absorbing material;
   multiple-layer film; and
   periodic structure and etched grating filter.

26. The apparatus according to claim 22 wherein:
the at least one wavelength filter comprises at least one tunable filter that performs wavelength band selection.

* * * * *